US006569433B1

(12) United States Patent
Reed et al.

(10) Patent No.: US 6,569,433 B1
(45) Date of Patent: May 27, 2003

(54) **COMPOUNDS AND METHODS FOR THE DIAGNOSIS AND TREATMENT OF *B. MICROTI* INFECTION**

(75) Inventors: Steven G. Reed, Bellevue, WA (US); Michael J. Lodes, Seattle, WA (US); Raymond L. Houghton, Bothell, WA (US); Paul R. Sleath, Seattle, WA (US); Patricia D. McNeill, Des Moines, WA (US); Mary J. Homer, Seattle, WA (US); Heather Secrist, Seattle, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/569,098

(22) Filed: May 10, 2000

Related U.S. Application Data

(63) Continuation-in-part of application No. 09/528,784, filed on Mar. 17, 2000, now Pat. No. 6,451,315, which is a continuation-in-part of application No. 09/286,488, filed on Apr. 5, 1999, which is a continuation-in-part of application No. 08/990,571, filed on Dec. 11, 1997, now Pat. No. 6,214,971, which is a continuation-in-part of application No. 08/845,258, filed on Apr. 24, 1997, now Pat. No. 6,183,976, which is a continuation-in-part of application No. 08/723,142, filed on Oct. 1, 1996, now Pat. No. 6,306,396.

(51) Int. Cl.[7] .................... A61K 39/002; A61K 39/015; C07K 14/44; C07K 1/00; G01N 33/569

(52) U.S. Cl. ................................ 424/191.1; 424/184.1; 424/185.1; 424/192.1; 424/265.1; 424/270.1; 530/350; 530/822; 514/44; 435/7.1; 435/7.22; 435/69.3; 435/69.7; 435/71.1; 536/23.1; 536/23.7; 536/23.4; 536/23.5

(58) Field of Search ........................... 424/136.1, 184.1, 424/185.1, 191.1, 192.1, 265.1, 270.1, 278.1; 435/7.1, 7.22, 69.3, 69.7, 69.1, 71.1; 530/350, 820, 822; 536/23.1, 23.4, 23.7, 23.5

(56) References Cited

U.S. PATENT DOCUMENTS

| | | | |
|---|---|---|---|
| 4,879,213 | A | 11/1989 | Fox et al. |
| 5,171,685 | A | 12/1992 | McElwain et al. |
| 5,837,545 | A | 11/1998 | Guy et al. |

FOREIGN PATENT DOCUMENTS

| | | | |
|---|---|---|---|
| EP | 018 579 | A | 11/1990 |
| EP | 0834 567 | A | 4/1998 |
| WO | WO 90/11776 | | 10/1990 |
| WO | WO 00/60090 | | 10/2000 |

OTHER PUBLICATIONS

Bowie et al. Science, 1990, vol. 247: p. 1306–1308.*
Houghten et al. Vaccines, 1986, Edited by Fred Brown: Cold Spring Harbor Laboratory.*
Pei et al 1991 J.B.C. 266, 16363–16369.*
Burgess et al., "Possible Dissociation of the Heparin–Binding and Mitogenic Activities of Heparin–Binding (Acidic Fibroblast) Growth Factor–1 from its Receptor–Binding Activities by Site–Directed Mutagenesis of a Single Lysine Residue," *The Journal of Cell Biology 111*:2129–2138, 1990.
Cox et al., "Antibody Levels in Mice Infected with *Babesia microti," Ann. Trop. Med. Parasitol 64*(2):167–173, 1970.
Foglino et al., "Nucleotide Sequence of the pepN Gene Encoding Aminopeptidase N of *Escherichia coli," Gene 49*:303–309, 1986.
Herwaldt et al., "A Fatal Case of Babesiosis in Missouri: Identification of Another Piroplasm that Infects Humans," *Ann International Med. 124*(7):643–650, 1996.
Krause et al., "Comparison on PCR with Blood Smear and Inoculatio of Small Animals for Diagnosis of *Babesia microti* Parasitemia," *J. Clinical Microbiology 34*(11):2791–2794, 1996.
Lazar et al., "Transforming Growth Factor α: Mutation of Aspartic Acid 47 Leucine 48 Results in Different Biological Activities," *Molecular and Cellular Biology 8*(3):1247–1252, 1988.
Levinson et al. (ed.), *Medical Microbiology & Immunology*, 3rd ed., Prentice Halll, Englewood Cliffs, NJ, 1998, pp. 292–293.
McCaman and Gabe, "The Nucleotide Sequence of the pepN Gene and it Over–Expression in *Escherichia Coli," Gene 48*:145–153, 1986.
Plotkin et al., *Vaccines*, W.B. Saunders Company, Philadelphia, 1988, Chapter 29, p. 571 (2nd full paragraph).
Rudinger et al., *Peptide Hormones*, University Park Press, Baltimore, MD, 1976, Ch. I, "Characteristics of the Amino Acids as Components of a Peptide Hormone Sequence," pp. 1–7.
Tetzlaff et al., "Isolation and Characterization of a Gene Associated with a Virulent Strain o *Babesia microti," Molecular and Biochemical Parasitology 40*:183–192, 1990.

* cited by examiner

*Primary Examiner*—Lynette F. Smith
*Assistant Examiner*—Padma Baskar
(74) *Attorney, Agent, or Firm*—Seed Intellectual Property Law Group PLLC

(57) ABSTRACT

Compounds and methods for the diagnosis and treatment of *B. microti* infection are disclosed. The compounds provided include polypeptides that contain at least one antigenic portion of a *B. microti* antigen and DNA sequences encoding such polypeptides. Antigenic epitopes of such antigens are also provided, together with pharmaceutical compositions and vaccines comprising such polypeptides, DNA sequences or antigenic epitopes. Diagnostic kits containing such polypeptides, DNA sequences or antigenic epitopes and a suitable detection reagent may be used for the detection of *B. microti* infection in patients and biological samples. Antibodies directed against such polypeptides and antigenic epitopes are also provided.

7 Claims, 9 Drawing Sheets

AACTAGATGCAGCACCACAATCACTACCACGTACCAATCATATACCAATAATGTACTAATAATGTACCAATAACTATGGTTTATAAAGATGGTGTCATTTAAATCAATATTAGTTCCTTATATTA 125

M V S F K S I L V P Y I

CACTCTTTTTAATGAGCGGTGCTGTCTTTGCAAGTGATACCGATCCCGAAGCTGGTGGGCCTAGTGAAGCTGGTGGGCCTAGTGGAACTGTTGGGCCCAGTGAAGCTGGTGGGCCTAGTGAAGCT 250

Repeat Sequences

T L F L M S G A V F A S D T D P E A G G P S E A G G P S G T V G P S E A G G P S E A

GGTGGGCCTAGTGGAACTGGTTGGCCTAGTGAAGCTGGTGGGCCTAGTGAAGCTGGTGGGCCTAGTGAAGCTGGTGGGCCTAGTGAAGCTGGTGGGCCTAGTGGAACTGGTTGGCCTAGTGGAAC 375

Repeat Sequences

G G P S G T G W P S E A G G P S E A G G P S E A G G P S E A G G P S G T G W P S G T

TGGTTGGCCTAGTGAAGCTGGTTGGTCTAGTGAACGATTTGGATATCAGCTTCTTCCGTATTCTAGAAGAATAGTTATATTTAATGAAGTTTGTTTATCTTATATATACAAACATAGTGTTATGA 500

Repeat Sequences

G W P S E A G W S S E R F G Y Q L L P Y S R R I V I F N E V C L S Y I Y K H S V M

TATTGGAACGAGATAGGGTGAACGATGGTCATAAAGACTACATTGAAGAAAAAACCAAGGAGAAGAATAAATTGAAAAAAGAATTGGAAAAATGTTTTCCTGAACAATATTCCCTTATGAAGAAA 625

I L E R D R V N D G H K D Y I E E K T K E K N K L K K E L E K C F P E Q Y S L M K K

GAAGAATTGGCTAGAATATTTGATAATGCATCCACTATCTCTTCAAAATATAAGTTATTGGTTGATGAAATATCAAACAAGGCCTATGGTACATTGGAAGGTCCAGCTGCTGATAATTTTGACCA 750

E E L A R I F D N A S T I S S K Y K L L V D E I S N K A Y G T L E G P A A D N F D H

TTTCCGTAATATATGGAAGTCTATTGTACTTAAAGATATGTTTATATATTGTGACTTATTATTACAACATTTAATCTATAAATTCTATTATGACAATACCGTTAATGATATCAAGAAAAATTTTG 875

F R N I W K S I V L K D M F I Y C D L L L Q H L I Y K F Y Y D N T V N D I K K N F

ACGAATCCAAATCTAAAGCTTTAGTTTTGAGGGATAAGATCACTAAAAAGGATGGAGATTATAACACTCATTTTGAGGACATGATTAAGGAGTTGAATAGTGCAGCAGAAGAATTTAATAAAATT 1000

D E S K S K A L V L R D K I T K K D G D Y N T H F E D M I K E L N S A A E E F N K I

GTTGACATCATGATTTCCAACATTGGGGATTATGATGAGTATGACAGTATTGCAAGTTTCAAACCATTTCTTTCAATGATCACCGAAATCACTAAAATCACCAAAGTTTCTAATGTAATAATTCC 1125

V D I M I S N I G D Y D E Y D S I A S F K P F L S M I T E I T K I T K V S N V I I P

TGGAATTAAGGCACTAACTTTAACCGTTTTTTTAATATTTATTACAAAATAGATGTAATACCAGATGTATACATTATTATATATTACAAAATTTACACATTATTTATGTATGAACGAACGAACAT 1250

CTCAGTCTTAAATGAAGAAATTGGGATAAATATGGAAATAGATTAAAGTAACATGAGAAAGATGAATATAATATTAGAATATGAAATTTAACAGAAATAAAATGAAGTAAAAGAGTGTATTTTGT 1375

AATAATTTATAATAAATTAGTATACAATGATTATATTACAGATGACTATTGATTATTGTATCAATTAAATATTGATTATTAATGATATCATATATGTATATGTTAATGATTGATTTGTTATACGT 1500

TGTGAATATGTTATATAATGACATACTATAATAATTAATATAATGTAGAGGATATTTTTTTTAATAGTATTTAATGAATATTATAGTTATAATTATAATAATGTAGATAAAAATGACATTAATTT 1625

GAATGTTTAAATTGAAATGTATGTAAAAATATGTATTTATAATCTGAATTGATTAATAATATAATATTCTACAATTAATTATTTTTGTAATTATAATAATTGATTATATTAATCTTTGAATTATT 1750

ATAAATAATATTATACTTCATTAAATTATTTCACATAAATTTCCAAATTATTATCCTTTATCTTAATGTTATCCAATTTTACACATCTTTCTTCATTACAATATTTTTTTACTAATCCTGTATGC 1875

TCATATTCATATTCTTTAGAAATATAACGAAAATTAGATGTAACTTCGCCACTTACAAGTAAACTACCATCAATATAATAATAATGAATACCATTCATGTCCGTATATTCTTTATATTTTTTATC 2000

ATATTTTATTTTGTGATTATTCCATTCATTTGTATCATTATTCAATGAGAGAAATAATAGCAGAAAGATCCTTCTATAGAAACATAAAATTCAATTAATACTGGATTATTATGTTTGCAAGTATA 2125

GATGTTTAAATCAATAACACTACCAGTTGGTAATTTAGCATTGTCATCAAATTCAATTATATAATCAGAAATTTTGATTTTATCAATTTTATTCGGATGTGATAATTTATTTTGTTCTGATTCAT 2250

CGATCATGTATACAAATACTATTGTTAAAGGTTCCCTATCCTTATAATTAAAGTGGCCAATAAGATTGGCATTAATTACATTAGTAGTGTGTGTATTTGTAATAGTATCATTAGTGGTACTGACA 2375

GTTGTTATAGGTTTTGATTTCCATAATGAAACATCATTTTTATCTACACAATACA 2430

*Fig. 1B*

```
 BI254   .......... ..AGDTDREA GGPSGTVGP. .......... ..........
BI1053   .......... ...GDTDREA GGPSGTVGP. .......... ..........
BI2227   .......... ..AGDTDREA GGPSGTVGP. .......... .SEAGGPSEA
BI2259   .......... ..AGDTDREA GGPSGTVGP. .......... .SEAGGPSEA
BI2253   .......... ........EA GGPSGTVGP. .......... .SEAGGPSEA
GRAC,S   .......... ...GDTDREA GGPSGTVGP. .....SEAGG PSEAGGPSEA
FISH,S   .......... ..AGDTDREA GGPSGTVGPS SAGGPSEAGG PSEAGGPSEA
MN1HAM   .......... ..AGDTDREA GGPSGTVGP. .......... .......SEA
MN2      .......... ..AGDTDREA GGPSGTVGP. .......... ..........
MN1PAT   .......... ..AGDTDREA GGPSGTVGP. .......... .......SEA
Bmni-6   YITLFLMSGA VFAGDTDREA GGPSGTVGP. .......... .......SEA
MN3      .......... ..AGDTDREA GGPSGTVGP. .......... .SEAGGPSEA
MR.T     .......... ..AGDTDREA GGPSGTVGP. .......... .SEAGGPSEA
         51                                                100
 BI254   ...SEAGGPS EAGGPSGTVG PSEAGGPSEA GGPSGTGWPS EAGGPSGTVG
BI1053   ...SEAGGPS EAGGPSGTVG PSEAGGPSEA GGPSGTGWPS EAGGPSGTVG
BI2227   GGPSEAGGPS EAGGPSEAGG PSEAGGPSEA GGPSEAGGPS EAGGPSEAGW
BI2259   GGPSEAGGPS EAGGPSEAGG PSEAGGPSEA GGPSEAGGPS EAGGPSEAGW
BI2253   GGPSEAGGPS EAGGPSEAGG PSEAGGPSEA GGPSEAGGPS EAGGPSEAGW
GRAC,S   GGPSEAGGPS EAGGPSEAGG PSEAGGPSEA GGPSEAGGPS EAGGPSEAGW
FISH,S   GGPSEAGGPS EAGGPSEAGG PSEAGGPSEA GGPSEAGGPS EAGGPSEAGW
MN1HAM   GGPSEAGGPS EAGGPSEAGG PSEAGGPSEA GGPSEAGGPS EAGGPSGTGW
MN2      ...SEAGGPS EAGGPSEAGG PSEAGGPSEA GGPSEAGGPS EAGGPSGTGW
MN1PAT   GGPSEAGGPS EAGGPSEAGG PSEAGGPSEA GGPSEAGGPS EAGGPSGTGW
Bmni-6   GGPSEAGGPS EAGGPSEAGG PSEAGGPSEA GGPSHAGGPS EAGGPSGTGW
MN3      GGPSEAGGPS EAGGPSEAGG PSEAGGPSEA GGPSEAGGPS EAGGPSGTGW
MR.T     GGPSEAGGPS EAGGPSEAGG PSEAGGPSEA GGPSEAGGPS EAGGPSGTGW
         101                                               150
 BI254   PSEAGGP... .........S EAGGPSGTGW PSGTGWPSEV GWPSERFGYQ
BI1053   PSEAGGP... .........S EAGGPSGTGW PSGTGWPSEV GWPSERFGYQ
BI2227   PSEAGWPSEA GGPSGTGWPS EAGWPSEAGW PSEAGWPSEA GW........
BI2259   PSEAGWPSEA GGPSGTGWPS EAGWPSEAGW PSEAGWPSEA GWPSERFGYQ
BI2253   PSEAGWPSEA GGPSGTGWPS EAGWPSEAGW PSEAGWPSEA GWPSER....
GRAC,S   PSEAGWPSEA GGPSGTGWPS EAGWPSEAGW PSEAGWPSEA GWPSERFGYQ
FISH,S   PSEAGWPSEA GGPSGTGWPS EAGWPSEAGW PSEAGWPSEA GWPSERFGYQ
MN1HAM   PSEAGWP... .........S EAGWPSEAGW PSEAGWPSEA GWPSERFGYQ
MN2      PSEAGWP... .........S EAGWPSEAGW PSEAGWPSEA GW........
MN1PAT   PSEAGWP... .........S EAGWPSEAGW PSEAGWPSEA GWPSERFGYQ
Bmni-6   PSEAGWP... .........S EAGWPSEAGW PSEAGWPSEA GWPSERFGYQ
MN3      PSEAGWP... .........S EAGWPSEAGW PSEAGWPSEA GWPSERFGYQ
MR.T     PSEAGWP... .........S EAGWPSEAGW PSEAGWPSEA GWPSERFGYQ
```

*Fig. 6A*

| | 151 | | 177 |
|---|---|---|---|
| BI254 | LLWYSRRIVI | .......... | ....... |
| BI1053 | LLWYSRRIVI | .......... | ....... |
| BI2227 | .......... | .......... | ....... |
| BI2259 | LLWYSRRIVI | .......... | ....... |
| BI2253 | .......... | .......... | ....... |
| GRAC,S | LLWYS..... | .......... | ....... |
| FISH,S | .......... | .......... | ....... |
| MN1HAM | LLWYSRRIVI | .......... | ....... |
| MN2 | .......... | .......... | ....... |
| MN1PAT | LLWYS..... | .......... | ....... |
| Bmni-6 | LLWYSRRIVI | FNEIYLSHIY | EHSVMIL |
| MN3 | LLWYSR.... | .......... | ....... |
| MR.T | LLWYSR.... | .......... | ....... |

*Fig. 6B*

COMPOUNDS AND METHODS FOR THE DIAGNOSIS AND TREATMENT OF *B. MICROTI* INFECTION

CROSS-REFERENCE TO RELATED APPLICATIONS

This application is a continuation-in-part of U.S. application Ser. No. 09/528,784, filed March 17, 2000, now U.S. Pat. No. 6,451,315, which is a continuation-in-part of U.S. application Ser. No. 09/286,488, filed Apr. 5. 1999, which is a continuation-in-part of U.S. application Ser. No. 08/990,571, filed Dec. 11, 1997, now U.S. Pat. No. 6,214,971, which is a continuation-in-part of U.S. appliction Ser. No. 08/845,258, filed Apr. 24, 1997, now U.S. Pat. No. 6,183,976, which is a continuation-in-part of U.S. application Ser. No. 08/723,142, filed Oct. 1, 1996, now U.S. Pat. No. 6,306,396.

TECHNICAL FIELD

The present invention relates generally to the detection of *Babesia microti* infection. In particular, the invention is related to polypeptides comprising a *B. microti* antigen, to antigenic epitopes of such an antigen and the use of such polypeptides and antigenic epitopes for the serodiagnosis and treatment of *B. microti* infection.

BACKGROUND OF THE INVENTION

Babesiosis is a malaria-like illness caused by the rodent parasite *Babesia microti* (*B. microti*) which is generally transmitted to humans by the same tick that is responsible for the transmission of Lyme disease and ehrlichiosis, thereby leading to the possibility of co-infection with babesiosis, Lyme disease and ehrlichiosis from a single tick bite. While the number of reported cases of *B. microti* infection in the United States is increasing rapidly, infection with *B. microti*, including co-infection with Lyme disease, often remains undetected for extended periods of time. Babesiosis is potentially fatal, particularly in the elderly and in patients with suppressed immune systems. Patients infected with both Lyme disease and babesiosis have more severe symptoms and prolonged illness compared to those with either infection alone.

The preferred treatments for Lyme disease, ehrlichiosis and babesiosis are different, with penicillins, such as doxycycline and amoxicillin, being most effective in treating Lyme disease, tetracycline being preferred for the treatment of ehrlichiosis, and anti-malarial drugs, such as quinine and clindamycin, being most effective in the treatment of babesiosis. Accurate and early diagnosis of *B. microti* infection is thus critical but methods currently employed for diagnosis are problematic.

All three tick-bome-illnesses share the same flu-like symptoms of muscle aches, fever, headaches and fatigue, thus making clinical diagnosis difficult. Microscopic analysis of blood samples may provide false-negative results when patients are first seen in the clinic. Indirect fluorescent antibody staining methods for total immunoglobulins to *B. microti* may be used to diagnose babesiosis infection, but such methods are time-consuming and expensive. There thus remains a need in the art for improved methods for the detection of *B. microti* infection.

SUMMARY OF THE INVENTION

The present invention provides compositions and methods for the diagnosis and treatment of *B. microti* infection. In one aspect, polypeptides are provided comprising an immunogenic portion of a *B. microti* antigen, or a variant of such an antigen that differs only in conservative substitutions and/or modifications. In one embodiment, the antigen comprises an amino acid sequence encoded by a DNA sequence selected from the group consisting of (a) sequences recited in SEQ ID NOs:1–17, 37, 40, 42, 45, 50, 51 and 91–110; (b) the complements of said sequences; and (c) sequences that hybridize to a sequence of (a) or (b) under moderately stringent conditions.

In another aspect, the present invention provides an antigenic epitope of a *B. microti* antigen comprising the amino acid sequence -$X_1$-$X_2$-$X_3$-$X_4$-$X_5$-Ser-(SEQ ID NO:35), wherein $X_1$ is Glu or Gly, $X_2$ is Ala or Thr, $X_3$ is Gly or Val, $X_4$ is Trp or Gly and $X_5$ is Pro or Ser. In one embodiment of this aspect, $X_1$ is Glu, $X_2$ is Ala and $X_3$ is Gly. In a second embodiment $X_1$ is Gly, $X_2$ is Thr and $X_5$ is Pro. The present invention further provides polypeptides comprising at least two of the above antigenic epitopes, the epitopes being contiguous.

In yet another aspect, the present invention provides an antigenic epitope of a *B. microti* antigen comprising an amino acid sequence selected from the group consisting of SEQ ID NOs:36 and 39, together with polypeptides comprising at least two such antigenic epitopes, the epitopes being contiguous.

In a related aspect, polynucleotides encoding the above polypeptides, recombinant expression vectors comprising these polynucleotides and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope. In specific embodiments, fusion proteins comprising an amino acid sequence of SEQ ID NO:85 or 87 are provided.

In further aspects of the subject invention, methods and diagnostic kits are provided for detecting *B. microti* infection in a patient. In one embodiment, the method comprises: (a) contacting a biological sample with at least one polypeptide comprising an immunogenic portion of a *B. microti* antigen; and (b) detecting in the sample the presence of antibodies that bind to the polypeptide, thereby detecting *B. microti* infection in the biological sample. In other embodiments, the methods comprise: (a) contacting a biological sample with at least one of the above polypeptides or antigenic epitopes; and (b) detecting in the sample the presence of antibodies that bind to the polypeptide or antigenic epitope. Suitable biological samples include whole blood, sputum, serum, plasma, saliva, cerebrospinal fluid and urine. The diagnostic kits comprise one or more of the above polypeptides or antigenic epitopes in combination with a detection reagent.

The present invention also provides methods for detecting *B. microti* infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of a DNA sequence encoding the above polypeptides.

In a further aspect, the present invention provides a method for detecting *B. microti* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment of this aspect, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of *B. microti* infection.

Within other aspects, the present invention provides pharmaceutical compositions that comprise one or more of the above polypeptides or antigenic epitopes, or a polynucleotide encoding such polypeptides, and a physiologically acceptable carrier. The invention also provides vaccines comprising one or more of the inventive polypeptides or antigenic epitopes and an immunostimulant, together with vaccines comprising one or more polynucleotides encoding such polypeptides and an immunostimulant.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 shows the genomic sequence of the *B. microti* antigen BMNI-3 (SEQ ID NO: 3) including a translation of the putative open reading frame (SEQ ID NO: 49). An internal six amino acid repeat sequence (SEQ ID NO:35) is indicated by vertical lines within the open reading frame.

FIG. 6 shows an alignment of the repeat region of different homologues of the *B. microti* antigen BMNI-6, illustrating the geographic variation in the number and location of the repeats.

DETAILED DESCRIPTION OF THE INVENTION

Figure 2A:
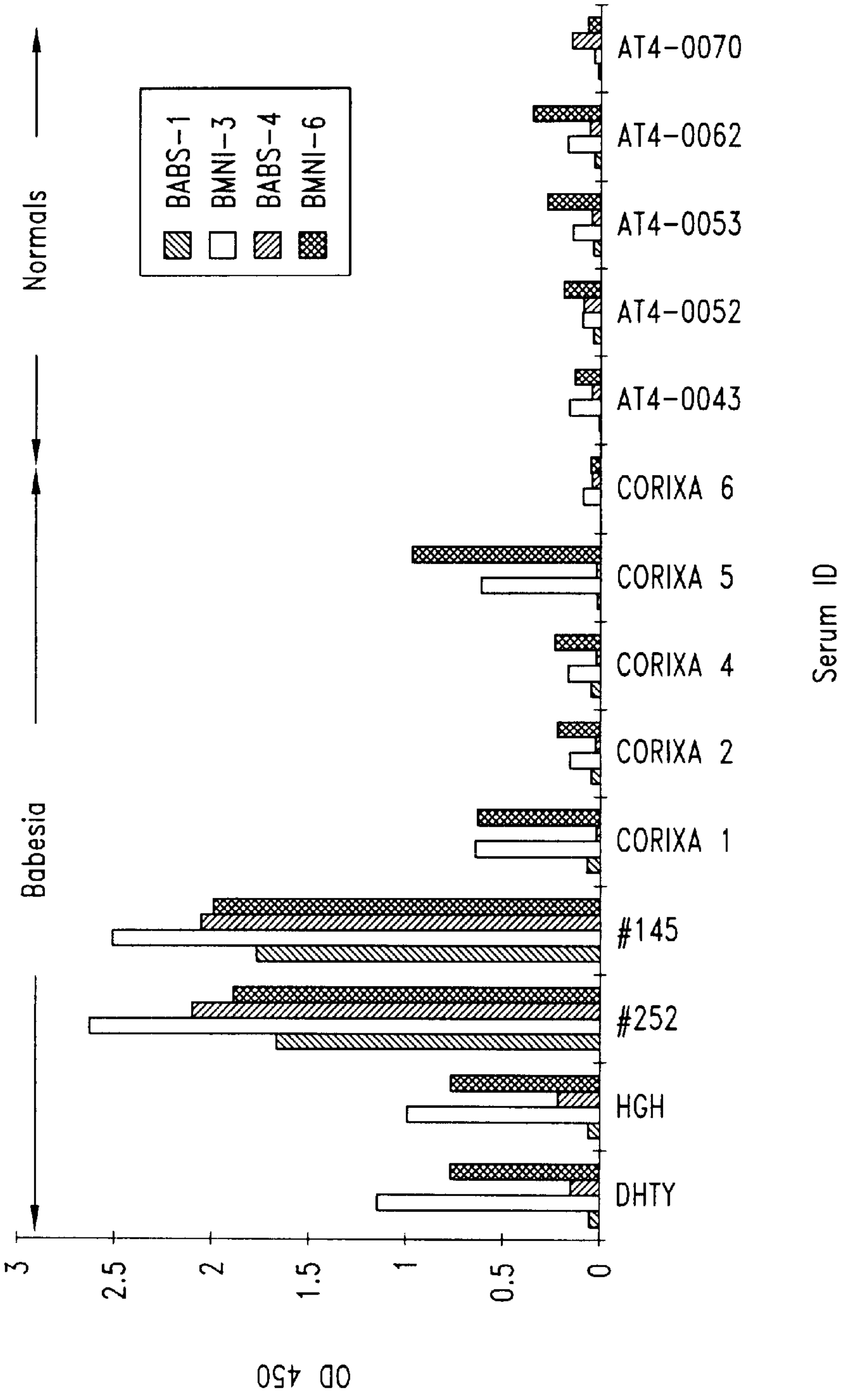
FIG. 2*a* shows the reactivity of the *B. microti* antigens BMNI-3 and BMNI-6, and the peptides BABS-1 and BABS-4 with sera from *B. microti*-infected individuals and from normal donors as determined by ELISA.

As noted above, the present invention is generally directed to compositions and methods for the diagnosis and treatment of *B. microti* infection. In one aspect, the compositions of the subject invention include polypeptides that comprise at least one immunogenic portion of a *B. microti* antigen, or a variant thereof.

As used herein, the termn "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *B. microti* antigen or may be heterologous, and such sequences may (but need not) be immunogenic.

An "immunogenic portion" of an antigen is a portion that is capable of eacting with sera obtained from a *B. microti*-infected individual (i.e., generates an absorbance reading with sera from infected individuals that is at least three standard deviations above the absorbance obtained with sera from uninfected individuals, in a representative ELISA assay described herein). Polypeptides comprising at least an immunogenic portion of one or more *B. microti* antigens as described herein may generally be used, alone or in combination, to detect *B. microti* in a patient.

Polynucleotides encoding the inventive polypeptides are also provided. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

The compositions and methods of the present invention also encompass variants of the above polypeptides and polynucleotides. Such variants include, but are not limited to, naturally occurring allelic variants of the inventive sequences.

Polynucleotides may comprise a native sequence (i.e., an endogenous sequence that encodes a protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=-4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

A polypeptide "variant," as used herein, is a polypeptide that differs from a native protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, referably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

In general, *B. microti* antigens, and polynucleotides encoding such antigens, may be prepared using any of a variety of procedures. For example, polynucleotides encoding *B. microti* antigens may be isolated from a *B. microti* genomic or cDNA expression library by screening with sera from *B. microti*-infected individuals as described below in Example 1, and sequenced using techniques well known to those of skill in the art. Polynucleotides encoding *B. microti* antigens may also be isolated by screening an appropriate *B. microti* expression library with anti-sera (e.g., rabbit) raised specifically against *B. microti* antigens.

Antigens may be induced from such clones and evaluated for a desired property, such as the ability to react with sera obtained from a *B. microti*-infected individual as described herein. Alternatively, antigens may be produced recombinantly, as described below, by inserting a polynucleotide that encodes the antigen into an expression vector and expressing the antigen in an appropriate host. Antigens may be partially sequenced using, for example, traditional Edman chemistry. See Edman and Berg, *Eur. J. Biochem.* 80:116–132, 1967.

Polynucleotides encoding antigens may also be obtained by screening an appropriate *B. microti* cDNA or genomic DNA library for polynucleotides that hybridize to degenerate oligonucleotides derived from partial amino acid sequences of isolated antigens. Degenerate oligonucleotides for use in such a screen may be designed and synthesized, and the screen may be performed, as described (for example) in Sambrook et al., *Molecular Cloning: A Laboratory Manual,* Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

Immunogenic portions of *B. microti* antigens may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a *B. microti* antigen generates at least about 20%, and preferably about 100%, of the signal induced by the full length antigen in a model ELISA as described herein.

Portions and other variants of *B. microti* antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a polynucleotide encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli,* yeast or a mammalian cell line, such as COS or CHO. The polynucleotides expressed in this manner may encode naturally occurring antigens, portions of naturally occurring antigens, or other variants thereof.

In another aspect, the present invention provides epitope repeat sequences, or antigenic epitopes, of a *B. microti* antigen, together with polypeptides comprising at least two such contiguous antigenic epitopes. As used herein an "epitope" is a portion of an antigen that reacts with sera from *B. microti*-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise the amino acid sequence -$X_1$-$X_2$-$X_3$-$X_4$-$X_5$-Ser-(SEQ ID NO:35), wherein $X_1$ is Glu or Gly, $X_2$ is Ala or Thr, $X_3$ is Gly or Val, $X_4$ is Trp or Gly, and $X_5$ is Pro or Ser. In another embodiment, the antigenic epitopes of the present invention comprise an amino acid sequence selected from the group consisting of SEQ ID NO: 36 and 39. As discussed in more detail below, antigenic epitopes provided herein may be employed in the diagnosis and treatment of *B. microti* infection, either alone or in combination with other *B. microti* antigens or antigenic epitopes. Antigenic epitopes and polypeptides comprising such epitopes may be prepared by synthetic means, as described generally above and in detail in Example 2.

In general, regardless of the method of preparation, the polypeptides, polynucleotides and antigenic epitopes disclosed herein are prepared in an isolated, substantially pure, form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope or an inventive polypeptide and an antigenic epitope of the present invention, together with variants of such fusion proteins. The fusion proteins of the present invention may also include a linker peptide between the polypeptides or antigenic epitopes.

A polynucleotide encoding a fusion protein of the present invention is constructed using known recombinant DNA techniques to assemble separate polynucleotides encoding, for example, the first and second polypeptides into an appropriate expression vector. The 3' end of a polynucleotide encoding the first polypeptide is ligated, with or without a peptide linker, to the 5' end of a polynucleotide encoding the second polypeptide so that the reading frames of the sequences are in phase to permit mRNA translation of the two polynucleotides into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. Nos. 4,935,233 and 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using polypeptides comprising an immunogenic portion of a *B. microti* antigen and/or the antigenic epitopes described above to diagnose babesiosis. In this aspect, methods are provided for detecting *B. microti* infection in a biological sample, using one or more of the above polypeptides and antigenic epitopes, alone or in combination. For clarity, the term "polypeptide" will be used when describing specific embodiments of the inventive diagnostic methods. However, it will be clear to one of skill in the art that the antigenic epitopes of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to *B. microti* antigens which may be indicative of babesiosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *B.*

*microti*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *B. microti*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be. detected by the addition of substrate (generally for a specific period of time), followed by spectroscopic or other analysis of the reaction products.

To determine the presence or absence of anti-*B. microti* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for babesiosis. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand comer (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for babesiosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*B. microti* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

In yet another aspect, the present invention provides antibodies to the polypeptides and antigenic epitopes of the present invention. Antibodies may be prepared by any of a variety of techniques known to those of ordinary skill in the art. See, e.g., Harlow and Lane, *Antibodies: A Laboratory Manual,* Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide or antigenic epitope coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of *B. microti* antigens using assays similar to those detailed above and other techniques well known to those of skill in the art, thereby providing a method for detecting *B. microti* infection in a patient.

The presence of *B. microti* infection may also, or alternatively, be detected based on the level of mRNA encoding a *B. microti*-specific protein in a biological sample. For example, at least two oligonucleotide primers may be employed in a polymerase chain reaction (PCR) based assay to amplify a portion of a *B. microti*-specific cDNA derived from a biological sample, wherein at least one of the oligonucleotide primers is specific for (i.e., hybridizes to) a polynucleotide encoding the *B. microti* protein. The amplified cDNA is then separated and detected using techniques well known in the art, such as gel electrophoresis. Similarly, oligonucleotide probes that specifically hybridize to a polynucleotide encoding a *B. microti* protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a *B. microti* protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule that is complementary to polynucleotide disclosed herein. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

Primers or probes may thus be used to detect *B. microti*-specific sequences in biological samples, preferably sputum, blood, serum, saliva, cerebrospinal fluid or urine. Oligonucleotide primers and probes may be used alone or in combination with each other.

In another aspect, the present invention provides methods for using one or more of the above polypeptides, antigenic epitopes or fusion proteins (or polynucleotides encoding such polypeptides) to induce protective immunity against *B. microti* infection in a patient. As used herein, a "patient" refers to any warm-blooded animal, preferably a human. A patient may be afflicted with a disease, or may be free of detectable disease and/or infection. In other words, protective immunity may be induced to prevent or treat babesiosis.

In this aspect, the polypeptide, antigenic epitope, fusion protein or polynucleotide is generally present within a pharmaceutical composition, or a vaccine or immunogenic composition. Pharmaceutical compositions may comprise one or more polypeptides, each of which may contain one or more of the above sequences (or variants thereof), and a physiologically acceptable carrier. Vaccines, or immunogenic compositions may comprise one or more of the above polypeptides and an immunostimulant, such as an adjuvant or a liposome (into which the polypeptide is incorporated). Such pharmaceutical compositions and vaccines may also contain other *B. microti* antigens, either incorporated into a combination polypeptide or present within a separate polypeptide.

Alternatively, a vaccine may contain a polynucleotide encoding one or more polypeptides, antigenic epitopes or fusion proteins as described above, such that the polypeptide is generated in situ. In such vaccines, the polynucleotide may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotide may be introduced using a viral expression system (e.g., vaccinia or other pox virus, retrovirus, or adenovirus), which may involve the use of a non-pathogenic (defective), replication competent virus. Techniques for incorporating polynucleotides into such expression systems are well known to those of ordinary skill in the art. The polynucleotide may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known *B. microti* antigen. For example, administration of a polynucleotide encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be Dadministered for a 1–36 week period. Preferably, 3 doses are administered, at interals of 3–4 months, and booster vaccinations may be given periodically thereafter. Alternate protocols may be appropriate for individual patients. A suitable dose is an amount of polypeptide or polynucleotide that, when administered as described above, is capable of raising an immune response in an immunized patient sufficient to protect the patieit from *B. microti* infection for at least 1–2 years. In general, the amount of polypeptide present in a dose (or produced in situ by the polynucleotide in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 mL to about 5 mL.

While any suitable carrier known to those of ordinary skill in thea rt may be employed in the pharmaceutical compositions of this invention, the type of carrer will vary depending on the mode of administration. For parenteral administration, such as subcutaneous injection, the carrier preferably comprises water, saline, alcohol, fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microsphres are disclosed, for example, in U.S. Pat. Nos. 4,897,268 and 5,075,109.

Any of a variety of adjuvants may be employed in the vaccines of this invention to enhance the immune response. Most adjuvants contain a substance designed to protect the antigen from rapid catabolism, such as aluminum hydroxide or mineral oil, and a stimulator of immune responses, such as lipid A, *Bortadella pertusis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants. Other adjuvants which may be employed in the inventive compositions include, for example, a combination of monophosphoryl lipid A, preferably t-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) may also be employed to potentiate an immune response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

The following Examples are offered by way of illustration and not by way of limitation.

EXAMPLE 1

Isolation of DNA Sequences Encoding *B. microti* Antigens

This example illustrates the preparation of DNA sequences encoding *B. microti* antigens by screening a *B. microti* expression library with sera obtained from patients infected with *B. microti.*

*B. microti* genomic DNA was isolated from infected hamsters and sheared by sonication. The resulting randomly sheared DNA was used to construct a *B. microti* genomic expression library (approximately 0.5–4.0 kbp inserts) with EcoRI adaptors and a Lambda ZAP II/EcoRI/CIAP vector (Stratagene, La Jolla, Calif.). The unamplified library ($1.2\times 10^6$/ml) was screened with an *E. coli* lysate-absorbed *B. microti* patient serum pool, as described in Sambrook et al., *Molecular Cloning: A Laboratory Manual,* Cold Spring Harbor Laboratories, Cold Spring Harbor, N.Y., 1989. Positive plaques were visualized and purified with goat-anti-human alkaline phosphatase. Phagemid from the plaques was rescued and DNA sequence for positive clones was obtained using forward, reverse, and specific internal primers on a Perkin Elmer/Applied Biosystem Inc. Automated Sequencer Model 373A (Foster City, Calif.).

Seventeen antigens (hereinafter referred to as BMNI-1–BMNI-17) were purified and three were possibly redundant. The determined DNA sequences for BMNI-1–BMNI-17 are shown in SEQ ID NOs:1–17, respectively. The deduced amino acid sequences for BMNI-1–BMNI-6, BMNI-8 and BMNI-10–BMNI-17 are shown in SEQ ID NOs:18–32, respectively, with the predicted 5' and 3' protein sequences for BMNI-9 being shown in SEQ ID NOs:33 and 34, respectively.

The isolated DNA sequences were compared to known sequence in the gene bank using the DNA STAR system. Nine of the seventeen antigens (BMNI-1, BMNI-2, BMNI-3, BMNI-5, BMNI-6, BMNI-7, BMNI-12, BMM-13 and BMNI-16) share some homology, with BMNI-1 and BMNI-16 being partial clones of BMNI-3. All of these nine antigens contain a degenerate repeat of six amino acids (SEQ ID NO:35), with between nine to twenty-two repeats occurring in each antigen. The repeat portion of the sequences was found to bear some similarity to a *Plasmodium falciparum* merozoite surface antigen (MSA-2 gene). FIG. 1 shows the genomic sequence of BMNI-3 including a translation of the putative open reading frame, with the internal six amino acid repeat sequence being indicated by vertical lines within the open reading frame.

A second group of five antigens bear some homology to each othe but do not show homology to any previously identified sequences (BMNI-4, BMNI-8, BMNI-9, BMNI-10 and BMNI-11). These antigens may belong to a family of genes or may represent parts of a repetitive sequence. BMNI-17 contains a novel degenerate repeat of 32 amino acids (SEQ ID NO:36). Similarly, the reverse complement of BMNI-17 (SEQ ID NO:37) contains an open reading frame that encodes an amino acid sequence (SEQ ID NO:38) having a degenerate 32 amino acid repeat (SEQ ID NO:39).

The reverse complement of BMNI-3 (SEQ ID NO:40) has an open reading frame which shows homology with the BMNI-4-like genes. The predicted amino acid sequence encoded by this open reading frame is shown in SEQ ID NO:41. The reverse complement of BMNI-5 (SEQ ID NO:42) contains a partial copy of a BMNI-3-like sequence and also an open reading frame with some homology to two yeast genes (*S. cerevisiae* G9365 ORF gene, and *S. cerevisiae* accession no. U18922). The predicted 5' and 3' amino acid sequences encoded by this open reading frame are shown in SEQ ID NOs:43 and 44, respectively. The reverse complement of BMNI-7 (SEQ ID NO: 45) contains an open reading frame encoding the amino acid sequence shown in SEQ ID NO:46.

A telomeric repeat sequence, which is conserved over a wide range of organisms, was found in five antigens (BMNI-2, BMNI-5, BMNI-6, BMNI-7 and BMNI-16), indicating that many of the isolated genes may have a telomere-proximal location in the genome. BMNI-10 appears to include a double insert, the 3'-most segment having some homology to *E. coli* aminopeptidase N. In addition, BMNI-7 contains apparently random insertions of hamster DNA. One such insertion has characteristics of a transposible element (i.e. poly A tail and flanked by a direct repeat).

In subsequent studies, two additional *B. microti* antigens were isolated by screening the *B. microti* genomic DNA expression library described above with a serum pool from *B. microti* infected patients that showed low reactivity with recombinant proteins generated from clones BMNI-2–BMNI-17. The determined DNA sequences for these two clones, hereinafter referred to as MN-10 and BMNI-20, are provided in SEQ ID NOs:50 and 51, respectively, with the corresponding predicted amino acid sequences being provided in SEQ ID NOs:52 and 53. MN-10 was found to extend the sequence of BMNI-4 in the 3' direction and BMNI-20 was found to extend the sequence of BMNI-17 in the 5' direction.

Additional *B. microti* sequences were identified using a technique designed to target secreted or shed antigens. Specifically, infection with *B. microti* (strain MN1) was established by intraperitoneal inoculation of 500 ul of cyropreserved hamster blood into 3 week old 50 g female Golden Syrian hamsters (SASCO; Charles River, Wilmington, Mass.). Infection was monitored by use of Giemsa-stained or acridine orange-stained blood smear over a 2 week period. Blood was harvested by cardiac puncture when the parasitemia levels reached 60–70%. Infected blood was diluted in saline to 100,000,000 infected red blood cells/mL. This blood was then used to inoculate several CB-17 SCID mice (Jackson Labs, Bar Harbor, Me.). Infection was monitored as above. At 3 weeks post-inoculation, the blood was harvested and had a parasitemia of approx. 5%. Serum was obtained by centrifuging the harvested blood at approx. 3000 rpm for 5–10 minutes and removing the serum from the top of the pelleted cells and debris. Syngeneic immunocompetent mice (BALB/c) were immunized with 200 ul total of a 1:1 (vol:vol) mixture of the SCID sera and MPL adjuvant monthly for a total of 5 injections. The BALB/c mice were bled via the tail vein 12 days post-3$^{rd}$ and 4$^{th}$ immunizations and were bled via cardiac stick post-5$^{th}$ immunization.

The serum was used to screen the *B. microti* expression library described above for secreted/shed antigens. Before screening, the serum was adsorbed with *E. coli* proteins on nitrocellulose filters. The library was plated on eleven large Petri plates at a concentration of approximately 20,000 plaques/plate. The plaques were lifted onto nitrocellulose filters and then processed using standard protocols with the adsorbed SCID sera as the primary antibody and goat anti-mouse (IgGT, IgA, IgM HPL), alkaline phosphatase conjugated, secondary antibody to visualize positive plaques.

Seventy plaques were picked upon the first screening of the library. These plaques were then processed and replated for secondary screens and, in some cases, tertiary screens. Twenty-seven clones were confirmed as positive and processed according to the protocols developed by Stratagene for their ZAP II vector for excision of the insert and subsequently cloning into the SOLR strain of *E. coli* (Stratagene, La Jolla, Calif.). The DNA from the inserts in each clone was sequenced in both directions. The 5' cDNA sequence for clone BM10 is provided in SEQ ID NO:91, the 5' and 3' cDNA sequences for clone BM12 are provided in SEQ ID NOs: 92 and 93, respectively; the 5' and 3' cDNA sequences for clone BM21 are provided in SEQ ID NOs:94 and 95, respectively; the 5' and 3' cDNA sequences for clone BM24 are provided in SEQ ID NOs:96 and 97, respectively; the 5' cDNA sequence for clone BM26 is provided in SEQ ID NOs:98; the complete cDNA sequence for the insert of clone BM31 is provided in SEQ ID NOs:99; the 5' and 3' cDNA sequences for clone BM33 are provided in SEQ ID NOs:100 and 101, respectively; the 3' cDNA sequence for clone BM37 are provided in SEQ ID NO:102; the complete cDNA sequence for a BMNI-10 clone is provided in SEQ ID NO:103; the complete cDNA sequence for the insert of clone BM61 is provided in SEQ ID NO:104; the 3' cDNA sequence for clone BM6.36 is provided in SEQ ID NO:105; the complete cDNA sequence for the insert of clone BM4 is provided in SEQ ID NO:106; the complete cDNA sequence for the insert of clone BM45 is provided in SEQ ID NO:107; complete cDNA sequence for the insert of clone BM40.42 is provided in SEQ ID NO:108; the complete cDNA sequence for a BMNI-11-like clone is provided in SEQ ID NO:109; and the complete cDNA sequence for a BMNI-15-like clone is provided in SEQ ID NO:110.

The sequences of SEQ ID NOs:96, 99, 101 and 104 were found to show some similarity to sequences previous deposited in Genbank and/or GeneSeq. The sequences of SEQ ID NOs:107 and 110 were found to have some overlap. SEQ ID NO:105 was found to show some similarity to the sequence of MN10 described above. The sequences of SEQ ID NOs:103, 109 and 110 were found to show some similarity to the sequences of BMNI-10, BMNI-11 and BMNI-15 described above. No significant similarities were found to the sequences of SEQ ID NOs:91–95, 97, 98, 100, 102, 106 and 108.

EXAMPLE 2

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

This procedure was used to synthesize two peptides (hereinafter referred to as BABS-1 and BABS-4) made to the repeat region of the isolated *B. microti* antigen BMNI-3. The sequences of BABS-1 and BABS-4 are shown in SEQ ID NO: 47 and 48, respectively.

EXAMPLE 3

Use of Representative Antigens and Peptides for Serodiagnosis of *B. microti* Infection A. Diagnostic Properties of Representative Antigens and Peptides as Determined by ELISA The diagnostic properties of recombinant BMNI-3, BMNI-4, BMNI-6, BMNI-15, MN-10 and BMNI-20, and the BABS-1 and BABS-4 peptides were determined as follows.

Assays were performed in 96 well plates coated overnight at 4° C. with 200 ng antigen/well added in 50 $\mu$l of carbonate coating buffer. The plate contents were then removed and the wells were blocked for 2 hours with 200 $\mu$l of PBS/1% BSA. After the blocking step, the wells were washed six times with PBS/0.1% Tween 20™. Fifty microliters of sera, diluted 1:100 in PBS/0.1% Tween 20™/0.1% BSA, was then added to each well and incubated for 30 minutes at room temperature. The plates were then washed six times with PBS/0.1% Tween 20™.

The enzyme conjugate (horseradish peroxidase-Protein A, Zymed, San Francisco, Calif.) was then diluted 1:20,000 in PBS/0.1% Tween 20™/0.1% BSA, and 50 μl of the diluted conjugate was added to each well and incubated for 30 minutes at room temperature. Following incubation, the wells were washed six times with PBS/0.1% Tween 20™. 100 μl of tetramethylbenzidine peroxidase substrate (Kirkegaard and Perry Laboratories, Gaithersburg, Md.) was added, undiluted, and incubated for 15 minutes. The reaction was stopped by the addition of 100 μl of 1N $H_2SO_4$ to each well and the plates were read at 450 nm.

FIG. 2a shows the reactivity of the recombinant BMNI-3 and BMNI-6 antigens and the two peptides BABS-1 and BABS-4 in the ELISA assay. The recombinant antigens and the two peptides were negative in ELISA with all seven samples from normal (B. microti negative) individuals. In contrast, both BMNI-3 and BMNI-6 detected six of the nine B. microti-infected samples, as compared to two out of the nine for the BABS-1 and BABS-4 peptides. This would suggest that BMNI-3 and BMNI-6 may contain other antigenic epitopes in addition to those present in the repeat epitopes in BABS-1 and BABS-4, or that an insufficient number of repeats are available in the peptides to fully express the antigenic epitopes present in the recombinant antigens BMNI-3 and BMNI-6.

Figure 2B:
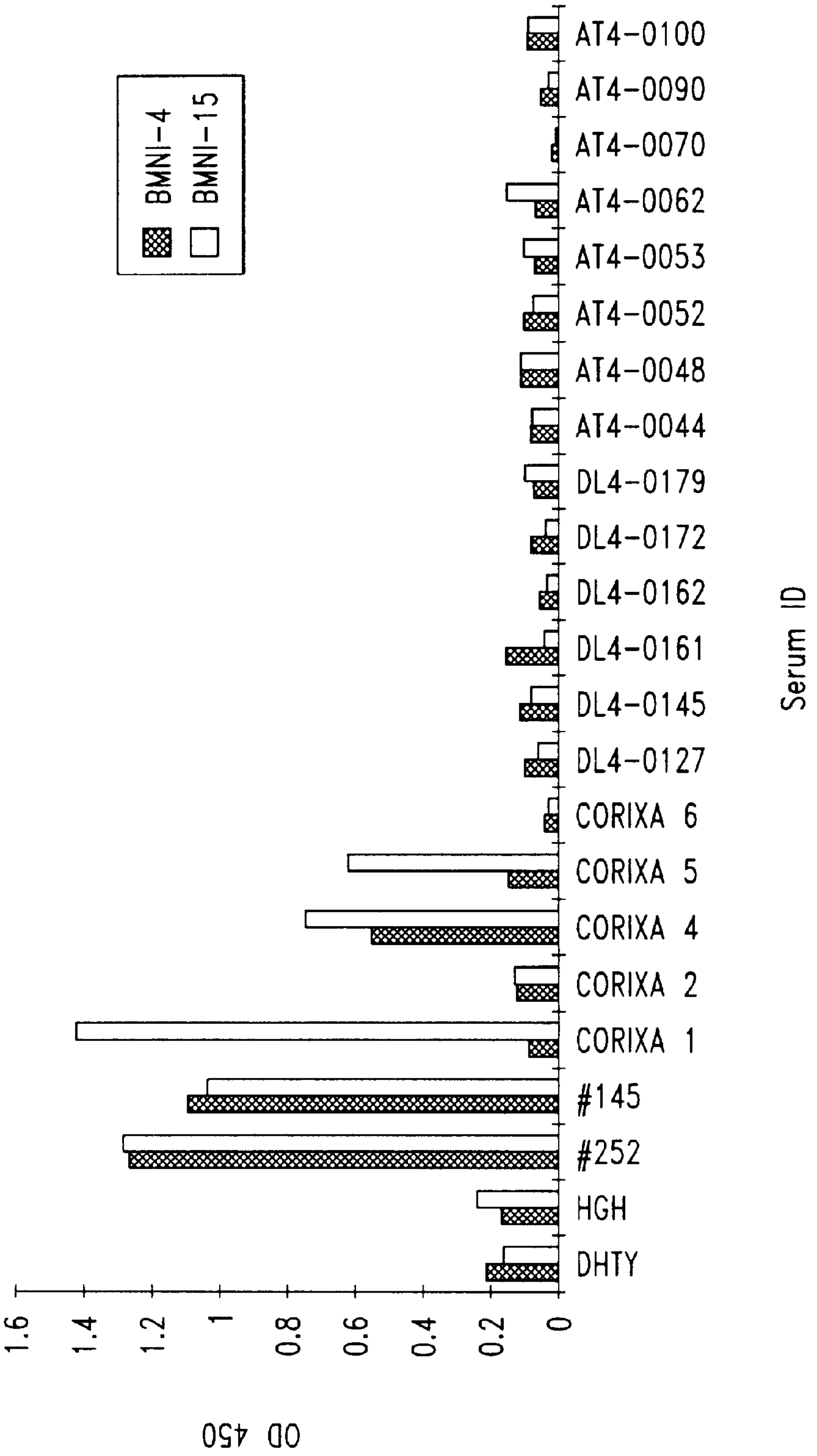
FIG. 2*b* shows the reactivity of the *B. microti* antigens BMNM-4 and BMNI-15 with sera from *B. microti*-infected individuals and from normal donors as determined by ELISA.

FIG. 2b shows the ELISA reactivity of the recombinant antigens BMNI-4 and BMNI-15. Both recombinants were negative with all fifteen samples from normal individuals. BMNI-4 detected four out of nine B. microti-infected samples and BMNI-15 detected six out of nine B. microti-infected samples. Both BMNI-4 and BMNI-15 detected a B. microti-infected sample which was not detected by BMNI-3 or BMNI-6, suggesting that BMNI-4 and BMNI-15 might be complementary to BMNI-3 and BMNI-6 in the ELISA test described herein.

Figure 3:
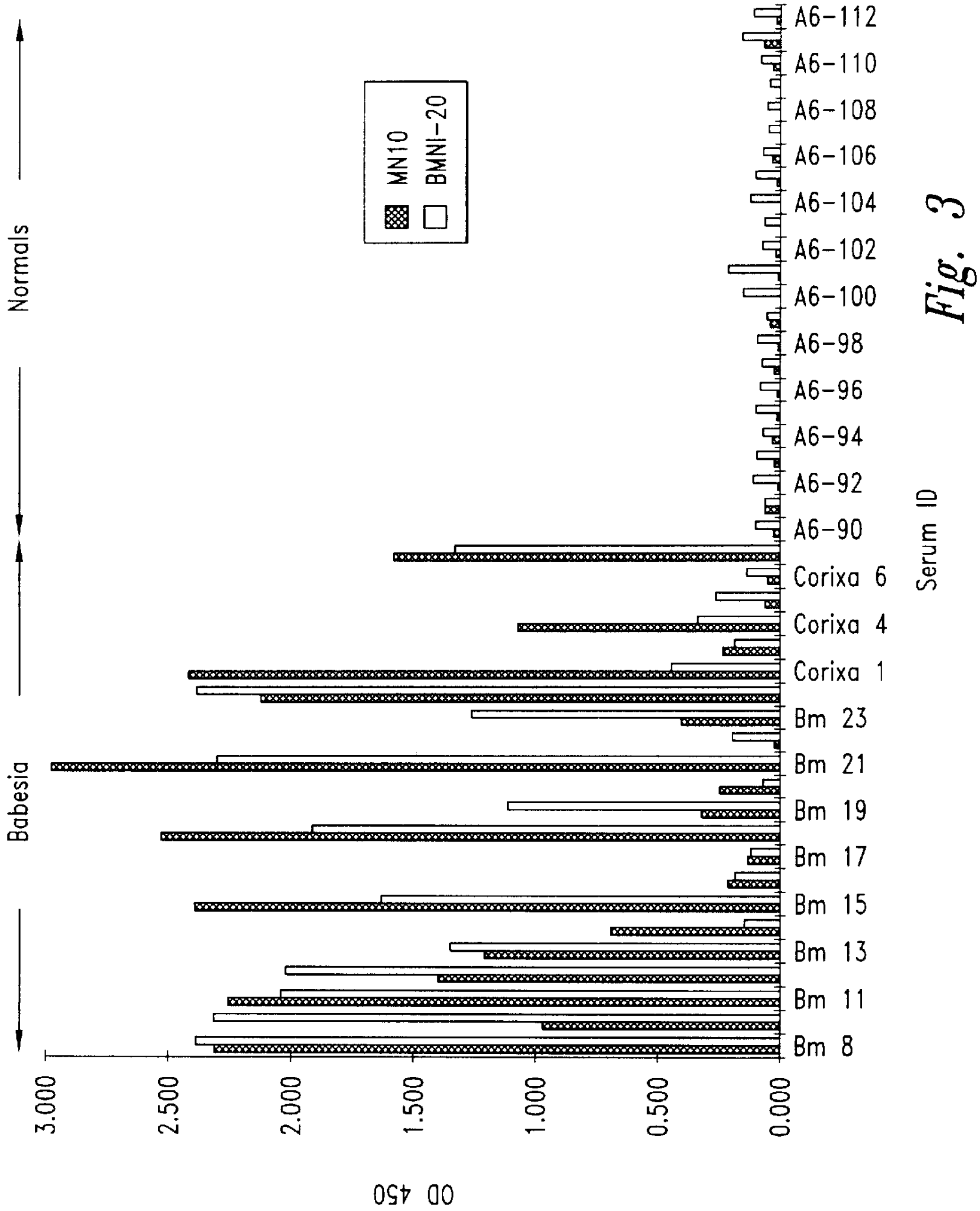
FIG. 3 shows the reactivity of the *B. microti* antigens MN-10 and BMNI-20 with sera from *B. microti*-infected patients and from normal donors as determined by ELISA.

The ELISA reactivity of recombinant MN-10 and BMNI-20 with sera from B. microti-infected patients and from normal donors is shown in FIG. 3. MN-10 and BMNI-20 were found to be reactive with B. microti-infected sera that were not reactive with recombinant BMNI-2 through BMNI-17. Therefore, MN-10 and BMNI-20 may be usefully employed in combination with other B. microti antigens of the present invention for the detection of B. microti infection.

Table 1 shows the reactivity of the recombinant B. microti antigens BMNI-2, BMNI-17, MN-10 and a combination of BMNI-17 and MN-10, as determined by ELISA, with Babesia-positive sera, sera positive for both Babesia and Ehrlichia, sera positive only for Ehrlichia, Lyme disease sera and sera from normal donors. The data indicate a sensitivity of approximately 93% and a specificity in normnal donors in excess of 98%. These results indicate that a combination of BMNI-17 and MN-10 is particularly effective in the diagnosis of B. microti infection.

TABLE 1

| Antigen | Babesia | Babesia/Ehrlichia | Ehrlichia | Lyme | Normal donors |
|---------|---------|-------------------|-----------|------|---------------|
| BMNI-2  | 27/50   | 2/3               | 1/4       | 0/10 | 1/73          |
| BMNI-17 | 35/50   | 3/3               | 0/4       | 0/10 | 0/86          |
| MN-10   | 37/49   | 3/3               | 0/4       | 1/10 | 1/98          |

TABLE 1-continued

| Antigen | Babesia | Babesia/Ehrlichia | Ehrlichia | Lyme | Normal donors |
|---------|---------|-------------------|-----------|------|---------------|
| BMNI-17/MN-10 | 46/50 | 3/3 | 0/4 | 1/10 | 1/98 |

B. Diagnostic Properties of Representative Antigens and Peptides as Determined by Western Analysis Western blot analyses were performnned on representative B. microti antigens as follows.

Antigens were induced as pBluescript SK-constructs (Stratagene) with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 0.1% Tween 20™/PBS. Blots were then washed 3 times in 0.1% Tween 20™/PBS and incubated with a B. microti patient serum pool (1:200) for a period of 2 hours. After washing blots in 0.1% Tween 20™/PBS times, immunocomplexes were detected by the addition of Protein A conjugated to $^{125}I$ (1/25000; NEN-Dupont, Billerica, Mass.) followed by exposure to X-ray film (Kodak XAR 5; Eastman Kodak Co., Rochester, N.Y.) at −70° C. for 1 day.

Figure 4:
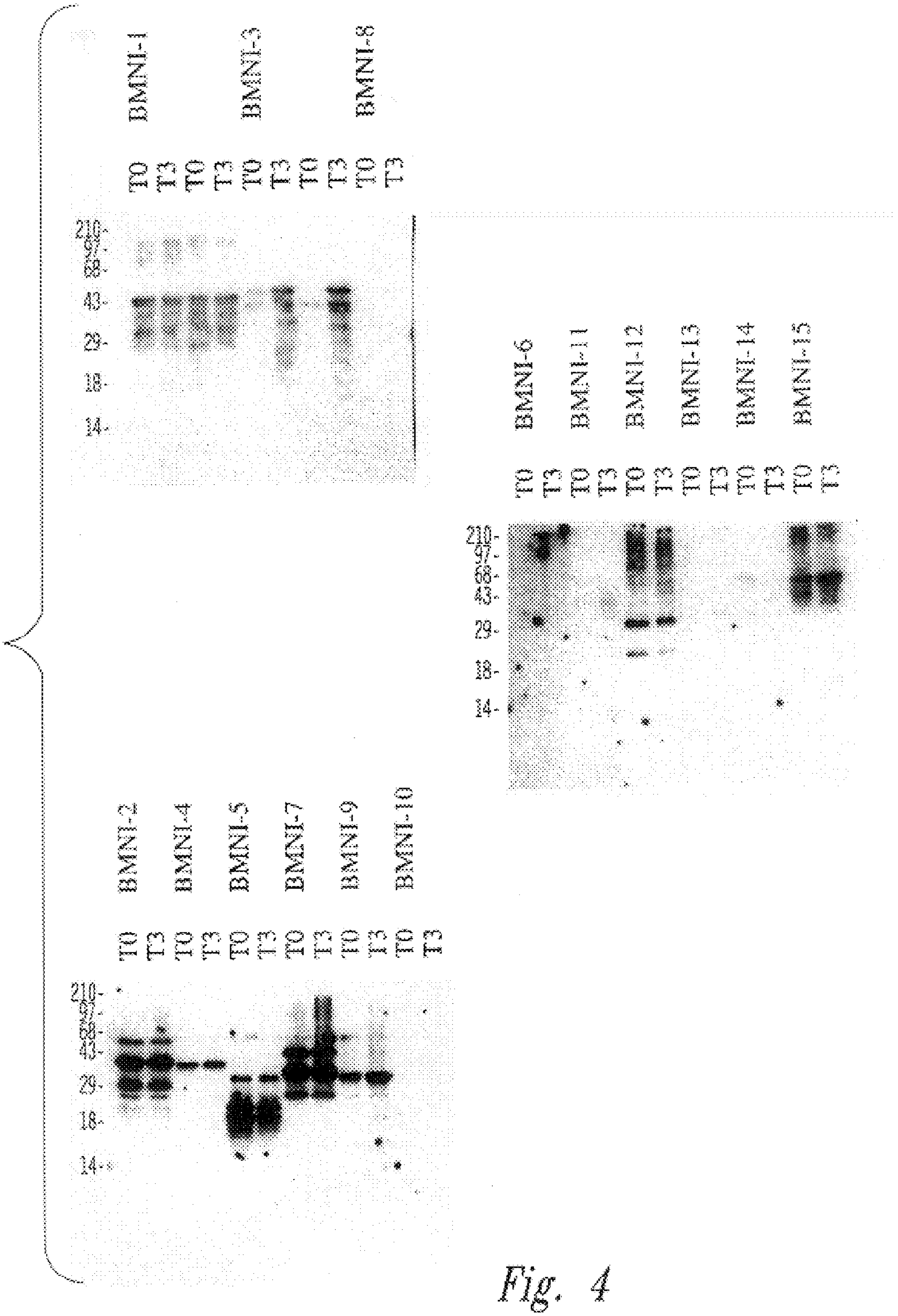
FIG. 4 shows the results of Western blot analysis of representative *B. microti* antigens of the present invention.

As shown in FIG. 4, resulting bands of reactivity with serum antibody were seen at 43 kDa for BMNI-1, 38 kDa for BMNI-2, 45 kDa for BMNI-3, 37 kDa for BMNI-4, 18 and 20 kDa for BMNI-5, 35 and 43 kDa for BMNI-7, 32 kDa for BMNI-9, 38 kDa for BMNI-11, 30 kDa for BMNI-12, 45 kDa for BMNI-15, and 43 kDa for BMNI-17 (not shown). Antigen BMNI-6, after reengineering as a pET 17b construct (Novagen, Madison, Wis.) showed a band of reactivity at 33 kDa (data not hown). Protein size standards, in kDa (Gibco BRL, Gaithersburg, M B), are shown to th left of the blots.

Western blots were performed on purified BMNI-3, BMNI-2, BMNI-15, BMNI-17 and MN-10 recombinant antigen with a series of patient sera from B. microti patients and from patients with either Lyme disease or ehrlichiosis. Specifically, purified recombinant antigen (4 μg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 5:
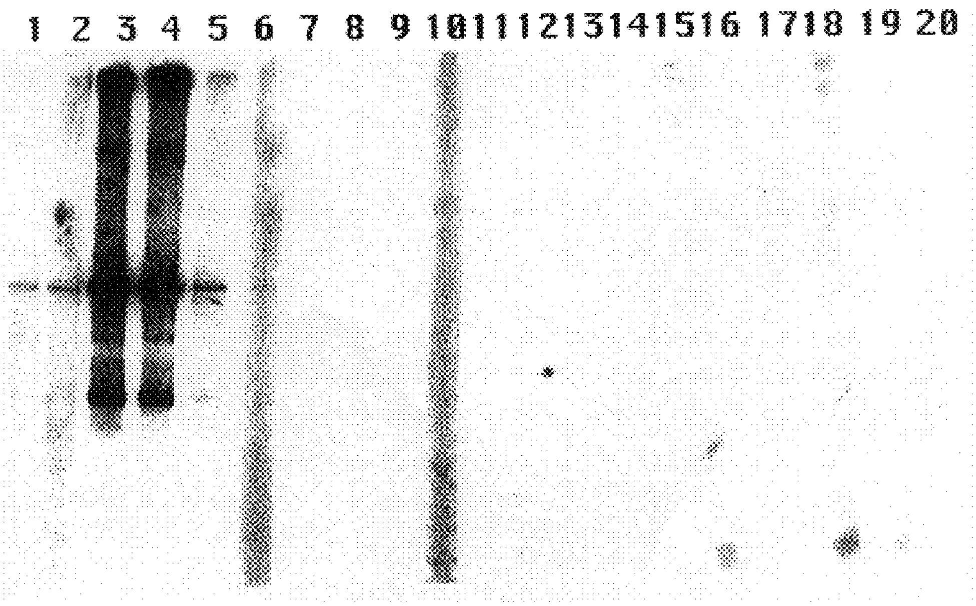
FIG. 5 shows the reactivity of purified recombinant *B. microti* antigen BMNI-3 with sera from *B. microti*-infected patients, Lyme disease-infected patients, ehrlichiosis-infected patients and normal donors as determined by Western blot analysis.

Lanes 1–9 of FIG. 5 show the reactivity of purified recombinant BMNI-3 with sera from nine B. microti-infected patients, of which five were clearly positive and a further two were low positives detectable at higher exposure to the hyperfilm ECL. This correlates with the reactivity as determined by ELISA. In contrast, no immunoreactivity was seen with sera from patients with either ehrlichiosis (lanes 10 and 11) or Lyme disease (lanes 12–14), or with sera from normal individuals (lanes 15–20). A major reactive band appeared at 45 kDa and a small break down band was seen at approximately 25 kDa.

Table 2, below, summarizes the reactivity of the recombinant antigens BMMI-2, BMNI-15, BMNI-17 and MN-10 with *B. microti* positive sera. No reactivity was seen with Lyme or Ehrlichia-infected sera, with little or no reactivity being seen with normal sera.

TABLE 2

| Sample ID | BMNI-2 | BMNI-15 | BMNI-17 | MN-10 |
|---|---|---|---|---|
| BM8 | ++ | ++ | +++++ | – |
| BM21 | ++ | – | ++++ | ++++ |
| COR4 | ± | ++++ | ++++ | + |
| COR5 | ± | +++ | + | – |
| 252 | ++++ | ++++ | ++++++ | +++ |

– indicates no reactivity

EXAMPLE 4

Analysis of Geographic Variation within Antigens

The reactivity of the inventive antigens with sera from *B. microti* patients, as determined by Western blot, was found to vary with the U.S. location of the patients. Accordingly, geographic variation within the gene encoding the exemplary antigen BMNI-6 was examined as follows.

Two PCR primers, referred to as BMNI-6/5' and BMNI-6/3' (SEQ ID NOs:54 and 55, respectively) were designed based on the region flanking the six amino acid degenerate repeat region of BMNI-6 (SEQ ID NO:6). These primers were employed to amplify genomic DNA from whole blood obtained from twelve *B. microti*-infected patients and genomic DNA from whole blood from *P. leucopus* and hamsters in a Perkin Elmer 480 thermal cycler using the manufacturer's protocol. PCR products were evaluated for size on 2% agarose gels and then Southern blotted and probed with a DIG-labeled oligonucleotide. Positive clones were sequenced using an Applied Biosystems Model 373A or 377 sequencer. RT-PCR was performed on Trizol LS extracted *B. microti*-infected hamster whole blood RNA using the primers described above, and the resulting clones were sequenced as described above.

These studies resulted in the isolation of twelve BMNI-6 homologues, referred to hereinafter as BI254, BI1053, BI2227, BI2259, BI2253, BI2018, RIFS, MN1HAM, MN2, MN1PAT, MN3 and MRT with MN1HAM being obtained from hamster and the other eleven from patients. The determined DNA sequences of these clones are provided in SEQ ID NO:56–67, respectively, with the corresponding predicted amino acid sequences being provided in SEQ ID NO:68–79, respectively. Isolates from hamsters had the same sequences as found in the corresponding human blood, suggesting that genetic variation of BMNI-6 does not occur during passage. However, clones from different patients often showed variation in the number and location of the degenerate repeat found within BMNI-6. An alignment of the repeat regions from each of the twelve clones is provided in FIG. 6. Furthermore, strains that were closely related geographically were also closely related at the sequence level. For example, three patients from Nantucket Island, Mass., harbored clones (BI2253, BI2259 and BI2227) that were indistinguishable from each other but distinct from those found in other northeastern or upper midwestern strains. These results suggest that considerable antigenic diversity exists among isolates of *B. microti* from the U.S. and that geographic clustering of subtypes exists.

EXAMPLE 5

Preparation and Characterization of *B. microti* Fusion Proteins

A. Preparation of a Fusion Protein Containing MN-10 and BMNI-17

A fusion protein containing the *B. microti* antigens MN-10 and BMNI-17, referred to as BaF-3, was prepared as follows.

MN-10 and BMNI-17 DNA was used to perform PCR using the primers PDM-285 and PDM-286 (SEQ ID NOs:80 and 81); and PDM-283 and PDM-284 (SEQ ID NOs:82 and 83), respectively. In both cases, the DNA amplification was performed using 10 μl of 10×Pfu buffer (Stratagene), 1 μl of 10 mM dNTPs, 2 μl each of the PCR primers at 10 μM concentration, 83 μl water, 1.5 μl Pfu DNA polymerase (Stratagene, La Jolla, Calif.) and 1 μl DNA at 50 ng/μl. Denaturation at 96° C. was performed for 2 min, followed by 40 cycles of 96° C. for 20 sec, 59° C. for 15 sec and 72° C. for 3 min, and lastly by 72° C. for 4 min. The MN-10 and BMNI-17 PCR products were digested with SspI and then ligated using a ligation kit from Panvera (Madison, Wis.). The resulting BaF-3 fusion was PCR amplified using primers PDM 285 and PDM-284 and the same conditions as listed above. This PCR product was then digested with ScaI and EcoRI, and cloned into a modified pET28 vector. The fusion construct was confirmed by sequencing. The expression construct was transformed into BL21 (DE3) CodonPlus cells (Novagen, Madison, Wis.) for induction and expression. The protein came out in the inclusion body pellet. This pellet was washed three times with a 0.5% CHAPS wash in 20 mM Tris (8.0) and 300 mM NaCl. The pellet was then solubilized in 8 M urea, 20 mM Tris (8.0), 300 mM NaCl and batch bound to Nickel NTA resin (Qiagen). The nickel resin was washed with 100 ml 8 M urea, 20 mM Tris (9.0), 300 mM NaCl, 1% DOC. A second wash was performed as described for the first wash, but with the omission of DOC. The protein was first eluted with 8 M urea, 20 mM Tris (9.0), 100 mM NaCl and 500 mM imidazole. In a second elution, the imidazole was increased to 1 M. The elutions were run on a 4–20 SDS-PAGE gel and the fractions containing the protein of interest were pooled and dialyzed against 1 mM Tris (8.).

The determined cDNA sequence of coding region for the BaF-3 fusion protein is provided in SEQ ID NO: 84, with the corresponding amino acid sequence being provided in SEQ ID NO: 85.

B. Preparation of a Fusion Protein Containing BMNI-15, MN-10 and BMNI-17

A fusion protein containing the *B. microti* antigens BMNI-15, MN-10 and BMNI-17, referred to as BaF-4, was prepared as follows.

BMNI-15 DNA was used to perform PCR using the primers PDM-349 and PDM-363 (SEQ ID NO: 88 and 89). DNA amplification was performed using 10 μl of 10×Pfu buffer (Stratagene), 1 μl of 10 mM dNTPs, 2 μl each of the PCR primers at 10 μM concentration, 83 μl water, 1.5 μl Pfu DNA polymerase (Stratagene, La Jolla, Calif.) and 1 μl DNA at 50 ng/μl. Denaturation at 96° C. was performed for 2 min, followed by 40 cycles of 96° C. for 20 sec, 61° C. for 15 sec and 72° C. for 3 min, and lastly by one cycle of 72° C. for 4 min. The PCR product was digested with PvuII and EcoRI, and cloned into a modified pET28 vector, which had been cut with Eco72I and EcoRI. The construct was confirmed to be correct by sequencing. MN-10/BMNI-17 DNA from BaF-3, described above, was used to perform PCR using the primers PDM-364 and PDM-284 (SEQ ID NO: 90 and 83, respectively). DNA amplification was performed using 10 μl of 10×Pfu buffer (Stratagene), 1 μl of 10 mM dNTPs, 2 μl each of the PCR primers at 10 μM concentration, 83 μl water, 1.5 μl Pfu DNA polymerase (Stratagene, La Jolla, Calif.) and 1 μl DNA at 50 ng/μl. Denaturation at 96° C. was performed for 2 min, followed by 40 cycles of 96° C. for 20 sec, 60° C. for 15 sec and 72° C. for 6 min, and lastly by 72° C. for 4 min. The PCR product was cut with BamHI and EcoRI, and cloned into the pPDM BMNI-15 construct at the BamHI and EcoRI sites. The resulting construct was found by sequence analysis to have a single base pair deletion 419 bp in from the stop codon. This base pair deletion was corrected by digesting the pPDM BaF4B-6 clone with KpnI and SphI, and purifying the 2.6 kb insert plus 5' vector. This band was then cloned into pPDM Trx2H BaF3–10 that was digested with the same enzymes and contained the 3' end of BMNI-17 plus most of the pPDM vector. The correct sequence was confirmed by sequence analysis and then transformed into the BL21 CodonPlus expression host (Novagen).

The determined cDNA sequence of the coding region of the BaF-4 fusion protein is provided in SEQ ID NO: 86, with the corresponding amino acid sequence being provided in SEQ ID NO: 87.

One of skill in the art will appreciate that the order of the individual antigens within the fusion protein may be changed and that comparable or enhanced activity could be expected provided each of the epitopes is still functionally available. In addition, truncated forms of the proteins containing active epitopes may be used in the construction of fusion proteins.

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising the amino acid sequence of SEQ ID NO:23.

2. An isolated polypeptide comprising an immunogenic portion of the amino acid sequence of SEQ ID NO:23, wherein said immunogenic portion selectively binds to an anti-*B.microti* antibody.

3. An isolated polypeptide comprising an amino acid sequence having at least 95% identity to the amino acid sequence of SEQ ID NO:23, wherein the isolated polypeptide selectively binds to an anti-*B. microti* antibody.

4. A fusion protein comprising the polypeptide according to claim 2.

5. A fusion protein comprising the polypeptide according to claim 3.

6. An isolated polypeptide comprising the amino acid sequence encoded by a DNA sequence of SEQ ID NO:6.

7. A fusion protein comprising the polypeptide according to claim 6.

* * * * *

UNITED STATES PATENT AND TRADEMARK OFFICE

CERTIFICATE OF CORRECTION

PATENT NO. : 6,569,433 B1
DATED : May 27, 2003
INVENTOR(S) : Steven G. Reed et al.

It is certified that error appears in the above-identified patent and that said Letters Patent is hereby corrected as shown below:

Title page,
Item [56], References Cited, FOREIGN PATENT DOCUMENTS, please add:
-- WO 99/29869…….06/1999 --

Signed and Sealed this

Seventeenth Day of February, 2004

JON W. DUDAS
*Acting Director of the United States Patent and Trademark Office*

SEQUENCE LISTING

<160> NUMBER OF SEQ ID NOS: 110

<210> SEQ ID NO 1
<211> LENGTH: 792
<212> TYPE: DNA
<213> ORGANISM: Babesia microti

<400> SEQUENCE: 1

```
cactcttttt aatgagcggt gctgtctttg caagtgatac cgatcccgaa gctggtgggc      60

ctagtgaagc tggtgggcct agtggaactg ttgggcccag tgaagctggt gggcctagtg     120

aagctggtgg gcctagtgga actggttggc ctagtgaagc tggtgggcct agtgaagctg     180

gtgggcctag tgaagctggt gggcctagtg aagctggtgg gcctagtgga actggttggc     240

ctagtggaac tggttggcct agtgaagctg gttggtctag tgaacgattt ggatatcagc     300

ttcttccgta ttctagaaga atagttatat ttaatgaagt ttgtttatct tatatataca     360

aacatagtgt tatgatattg gaacgagata gggtgaacga tggtcataaa gactacattg     420

aagaaaaaac caaggagaag aataaattga aaaaagaatt ggaaaaatgt tttcctgaac     480

aatattccct tatgaagaaa gaagaattgg ctagaatatt tgataatgca tccactatct     540

cttcaaaata taagttattg gttgatgaaa tatcaaacaa ggcctatggt acattggaag     600

gtccagctgc tgataatttt gaccatttcc gtaatatatg gaagtctatt gtacttaaag     660

atatgtttat atattgtgac ttattattac aacatttaat ctataaattc tattatgaca     720

ataccgttaa tgatatcaag aaaaattttg acgaatccaa atctaaagct ttagttttga     780

gggataagat ca                                                         792
```

<210> SEQ ID NO 2
<211> LENGTH: 2732
<212> TYPE: DNA
<213> ORGANISM: Babesia microti

<400> SEQUENCE: 2

```
aaaccctaaa ccctaaaccc taaaccctaa accctaaacc cctaaaccct aaaccctaaa      60

ccctaaaccc taaaccctaa aaccctaaac cctaaaccct aaaccctaaa ccctaaaccc     120

taaaccctaa accctaaacc ctaaacccta aaccctaaac cctaaaccct aaaccctaaa     180

ccctaaaccc taaaccctaa accctaaacc ctaaacccct aaaccctaaa ccctaaaccc     240

taaaccctaa accctaaacc ctaaacccta aaccctaaac cctaaaccct aaaccctaaa     300
```

-continued

```
ccctaaaccc taaaccctaa accctaaacc ctaaaaccct aaaccctaaa ccctaaaccc    360
taaaccctaa accctaaacc cctaaaccct aaaccctaaa ccctaaaccc taaaccctaa    420
acccctaaac cctaaacccc taaaccctaa accctaaacc ctaaacccta aaccctaaac    480
cctaaaccct aaaccctaaa ccctaaaccc taaaccccta aaccctaaac cctaaaccct    540
aaaccctaaa ccctaaaccc taaaccctaa accctaaccc taaccctaac cctaacccta    600
acctagcctt cattgacgtc tatccccaat cttagaaaaa tcttcaaatc gattctagaa    660
taactggaaa caattatcag aaattgtata actgcttatt agcttattag cttattagtt    720
aggatgtatg cacattgatg acaactagat gcagcaccac aatcactacc acgtaccaat    780
catataccaa taatgtacta ataatgtacc aataactatg gtttataaag atggtgtcat    840
ttaaatcaat attagttcct tatattacac tctttttaat gagcggtgct gtctttgcaa    900
gtgataccga tcccgaagct ggtgggccta gtgaagctgg tgggcctagt ggaactgttg    960
ggcccagtga agctggtggg cctagtgaag ctggtgggcc tagtggaact gttgggccca   1020
gtgaagctgg tgggcctagt gaagctggtg ggcctagtgg aactggttgg cctagtgaag   1080
ctggtgggcc tagtgaagct ggtgggccta gtggaactgt tgggcccagt gaagctggtg   1140
ggcctagtga agctggtggg cctagtggaa ctggttggcc tagtgaagct ggtgggccta   1200
gtgaagctgg tgggcctagt gaagctggtg ggcctagtga agctggtggg cctagtggaa   1260
ctggttggcc tagtggaact ggttggccta gtgaagctgg ttggtctagt gaacgatttg   1320
gatatcagct tcttccgtat tctagaagaa tagttatatt taatgaagtt tgtttatctt   1380
atatatacaa acatagtgtt atgatattgg aacgagatag ggtgaacgat ggtcataaag   1440
actacattga agaaaaaacc aaggagaaga ataaattgaa aaaagaattg gaaaaatgtt   1500
ttcctgaaca atattccctt atgaagaaag aagaattggc tagaatattt gataatgcat   1560
ccactatctc ttcaaaatat aagttattgg ttgatgaaat atcaaacaag gcctatggta   1620
cattggaagg tccagctgct gataattttg accatttccg taatatatgg aagtctattg   1680
tacttaaaga tatgtttata tattgtgact tattattaca acatttaatc tataaattct   1740
attatgacaa taccgttaat gatatcaaga aaaattttga cgaatcctgg acacagacat   1800
taaaagaata agcctgcttg gggtttctg ggcatctctt catgagtgcc agtcacacaa   1860
ctcttctgtg agccttctac aataaggact ttgtgtgctt cgatattttt ttagactaaa   1920
gtgaactctc tcctccacct ttggcttcag ttagttattt caaatggcaa aagttattaa   1980
aaattccagt gtggaaactg gcttaaccaa caggaaaggg gttttgaggt cgcatcacta   2040
agcatcaagt ttaacaccaa catgcctgga ggattggctt agccggttgc tagggcaggc   2100
ctgtggcagg gttcttatcc cagctattaa cgctcccttc ccactcctcc aagtcctgca   2160
agtcctggat acagtgaaat gtaattgcat atcccatatc ctttgctagt atcaaatgga   2220
taaaacccaa aatggagtca taccaaatga tctcatgtat acaatacctg aatagtcttg   2280
aactgatgca ctgttagata gtatgcactt actcttcagc tattcatagt gtgcctctgc   2340
acagtgatgg aaaagaggag cactggggga gctcggtttt caagggacaa aggagaataa   2400
gacacacaaa gaaatccaag gtagagcaga gaaaggatgg agacacagaa ggtttgcagg   2460
aacaggaagc gaaggatgct ccagtctgag ggggagggga aagagagcct cttgagtagc   2520
cagcacctga acttggcctg gaagcttggt ggataaggca ggataaagga ggtgtggcct   2580
ctttggtatc ctcccattga taaaggagct ccctgaccct tcactagacc atcatcagtc   2640
ctatggttct tagaccaata gaacacaatg gaattgattt gttccacttt ccaggttaag   2700
```

-continued acttacagtc agggaagttt gtttttcttg cc 2732

<210> SEQ ID NO 3
<211> LENGTH: 2430
<212> TYPE: DNA
<213> ORGANISM: Babesia microti

<400> SEQUENCE: 3

```
aactagatgc agcaccacaa tcactaccac gtaccaatca tataccaata atgtactaat     60

aatgtaccaa taactatggt ttataaagat ggtgtcattt aaatcaatat tagttcctta    120

tattacactc tttttaatga gcggtgctgt ctttgcaagt gataccgatc ccgaagctgg    180

tgggcctagt gaagctggtg ggcctagtgg aactgttggg cccagtgaag ctggtgggcc    240

tagtgaagct ggtgggccta gtggaactgg ttggcctagt gaagctggtg ggcctagtga    300

agctggtggg cctagtgaag ctggtgggcc tagtgaagct ggtgggccta gtggaactgg    360

ttggcctagt ggaactggtt ggcctagtga agctggttgg tctagtgaac gatttggata    420

tcagcttctt ccgtattcta gaagaatagt tatatttaat gaagtttgtt tatcttatat    480

atacaaacat agtgttatga tattggaacg agatagggtg aacgatggtc ataaagacta    540

cattgaagaa aaaaccaagg agaagaataa attgaaaaaa gaattggaaa aatgttttcc    600

tgaacaatat tcccttatga agaaagaaga attggctaga atatttgata atgcatccac    660

tatctcttca aaatataagt tattggttga tgaaatatca aacaaggcct atggtacatt    720

ggaaggtcca gctgctgata attttgacca tttccgtaat atatggaagt ctattgtact    780

taaagatatg tttatatatt gtgacttatt attacaacat ttaatctata aattctatta    840

tgacaatacc gttaatgata tcaagaaaaa ttttgacgaa tccaaatcta aagctttagt    900

tttgagggat aagatcacta aaaaggatgg agattataac actcattttg aggacatgat    960

taaggagttg aatagtgcag cagaagaatt taataaaatt gttgacatca tgatttccaa   1020

cattggggat tatgatgagt atgacagtat tgcaagtttc aaaccatttc tttcaatgat   1080

caccgaaatc actaaaatca ccaaagtttc taatgtaata attcctggaa ttaaggcact   1140

aactttaacc gttttttttaa tatttattac aaaatagatg taataccaga tgtatacatt   1200

attatatatt acaaaattta cacattattt atgtatgaac gaacgaacat ctcagtctta   1260

aatgaagaaa ttgggataaa tatggaaata gattaaagta acatgagaaa gatgaatata   1320

atattagaat atgaaattta acagaaataa aatgaagtaa aagagtgtat tttgtaataa   1380

tttataataa attagtatac aatgattata ttacagatga ctattgatta ttgtatcaat   1440

taaatattga ttattaatga tatcatatat gtatatgtta atgattgatt tgttatacgt   1500

tgtgaatatg ttatataatg acatactata ataattaata taatgtagag gatatttttt   1560

ttaatagtat ttaatgaata ttatagttat aattataata atgtagataa aaatgacatt   1620

aatttgaatg tttaaattga aatgtatgta aaaatatgta tttataatct gaattgatta   1680

ataaatataat attctacaat taattatttt tgtaattata ataattgatt atattaatct   1740

ttgaattatt ataaataata ttatacttca ttaaattatt tcacataaat ttccaaatta   1800

ttatccttta tcttaatgtt atccaatttt acacatcttt cttcattaca atattttttt   1860

actaatcctg tatgctcata ttcatattct ttagaaatat aacgaaaatt agatgtaact   1920

tcgccactta caagtaaact accatcaata taataataat gaataccatt catgtccgta   1980

tattctttat attttttatc atattttatt ttgtgattat tccattcatt tgtatcatta   2040
```

-continued

```
ttcaatgaga gaaataatag cagaaagatc cttctataga aacataaaat tcaattaata   2100

ctggattatt atgtttgcaa gtatagatgt ttaaatcaat aacactacca gttggtaatt   2160

tagcattgtc atcaaattca attatataat cagaaatttt gattttatca attttattcg   2220

gatgtgataa tttattttgt tctgattcat cgatcatgta tacaaatact attgttaaag   2280

gttccctatc cttataatta aagtggccaa taagattggc attaattaca ttagtagtgt   2340

gtgtatttgt aatagtatca ttagtggtac tgacagttgt tataggtttt gatttccata   2400

atgaaacatc atttttatct acacaataca                                    2430
```

<210> SEQ ID NO 4
<211> LENGTH: 1991
<212> TYPE: DNA
<213> ORGANISM: Babesia microti

<400> SEQUENCE: 4

```
aatgtacaag atcaaaattt ctgattatat aattgaattt gatgacaatg ctaaattacc     60

aactgataat gttattggta tatccatcta tacttgtgaa cacaataatc cagtattaat    120

tgaattttat gtttctaaaa aaggatcaat ctgctattat ttctactcaa tgaataatga    180

tacaaataaa tggaataatc acaaaataaa atatgacaaa agatttaatg aacatactga    240

catgaatggt attcattatt attatattga tggtagttta cttgcgagtg gcgaagttac    300

atctaatttt cgttatattt ctaaagaata tgaatatgag catacagaat tagcaaaaga    360

gcattgcaag aaagaaaaat gtgtaaatgt ggataacatt gaggataata atttgaaaat    420

atatgcgaaa cagtttaaat ctgtagttac tactccagct gatgtagcgg gtgtgtcaga    480

tggatttttt atacgtggcc aaaatcttgg tgctgtgggc agtgtaaatg aacaacctaa    540

tactgttggt atgagtttag aacaattcat caagaacgag ctttattctt ttagtaatga    600

aatttatcat acaatatcta gtcaaatcag taattctttc ttaataatga tgtctgatgc    660

aattgttaaa catgataact atattttaaa aaaagaaggt gaaggctgtg aacaaatcta    720

caattatgag gaatttatag aaaagttgag gggtgctaga agtgagggga ataatatgtt    780

tcaggaagct ctgataaggt ttaggaatgc tagtagtgaa gaaatggtta atgctgcaag    840

ttatctatcc gccgcccttt tcagatataa ggaatttgat gatgaattat tcaaaaaggc    900

caacgataat tttggacgcg atgatggata tgattttgat tatataaata caaagaaaga    960

gttagttata cttgccagtg tgttggatgg tttggattta ataatggaac gtttgatcga   1020

aaatttcagt gatgtcaata atacagatga tattaagaag gcatttgacg aatgcaaatc   1080

taatgctatt atattgaaga aaaagatact tgacaatgat gaagattata agattaattt   1140

tagggaaatg gtgaatgaag taacatgtgc aaacacaaaa tttgaagccc taaatgattt   1200

gataatttcc gactgtgaga aaaaaggtat taagataaac agagatgtga tttcaagcta   1260

caaattgctt ctttccacaa tcacctatat tgttggagct ggagttgaag ctgtaactgt   1320

tagtgtgtct gctacatcta atggaactga atctggtgga gctggtagtg gaactggaac   1380

tagtgtgtct gctacatcta ctttaactgg taatggtgga actgaatctg gtggaacagc   1440

tggaactact acgtctagtg gaacttggtt tggaaaatga aaaattagct ctagaaacac   1500

tttattgtta atttttaaaa acctattgaa aaatcagatt gtaaaacata attccacttc   1560

taaccatgct atgatttaac taatcaggac aaaaagaaag cataatcaac attattcatt   1620

cagtgatggt gacataattc agagaatgtg gcaattgcct cttgaagacc agagttccat   1680

ccacaggacc cacatggtta aaggagagag ctaactcctg aaagttgtcc tctgactaac   1740
```

-continued

```
acattcaact tttgagtgtc tcatttatgt gttggcttct gtctaatgtg ggaaaatcat   1800

taagggctct taaatcagat cctcattctc tctattaata aactatgtga taacatcctt   1860

cagctatgaa aatgtcagga gagagtcagg aaaatggaag atattgttca ggacttaact   1920

aggtggtggc acacagttcc tttacacaga ttcctcagga caagttttag gtgaggtttt   1980

gatctatcct g                                                        1991


<210> SEQ ID NO 5
<211> LENGTH: 1271
<212> TYPE: DNA
<213> ORGANISM: Babesia microti

<400> SEQUENCE: 5

ttcactaggc caaccagctt cactaggcca accagcttca ctaggccaac cagcttcact     60

aggccaacca gcttcactag gccaaccagc ttcactaggc caaccagttc cactaggccc    120

accagcttca ctaggcccac cagcttcact aggcccacca gcttcactag gccaaccagt    180

tccactaggc ccaccagctt cactaggccc accagcttca ctaggcccac cagcttcact    240

aggcccacca gcttcactag gcccaccagc ttcactaggc ccaccagctt cactaggccc    300

accagcttca ctaggcccac cagcttcact aggcccaaca gttccactag gcccaccagc    360

ttcgcgatcg gtatcacctg caaagacagc accgctcatt aaaaagagtg taatataagg    420

aactaatatt gatttaaatg acaccatctt tataaaccat agttattggt acattattag    480

tacattattg gtatatgatt ggtacgtggt agtgattgtg gtgctgcatc tagttgtcat    540

caatgtgcat acatcctaac taataagcta ataagctaat aagcagttat acaatttctg    600

ataattgctt ccagttattc tagaatcgat ttgaagattt ttctaagatt ggggatagac    660

gtcaatgaag gctaggttag ggttagggtt agggttaggg ttagggttta gggtttaggg    720

tttagggttt agggtttagg gttagggttt agggtttagg gtttagggtt taggctccca    780

agttgtcccg tgaaagggcc gtgtctttga taaattttgc cgtcctgtac gtttcctttc    840

tagaatgcac aaaaacaaga atttggcagc tagaaacatc gttaatcacc tcttggtaga    900

gaatttcgtt gattgcgttg aaacgtttga tagccttctt ctccttcacg ccataataca    960

cctgctccaa gggcacaggc ctaaagtggc tgccaaagta gaaaagccct cggtctagat   1020

taacagtgag aaatctagcc acgtcttcgt agtttggaag cgtggccgat agaccaacta   1080

gccttacgcg ttcgggcctc tgactcaggc gggccacaat agcctccagc actggacccc   1140

tagtgtcatg gagtaggtgt atttcatcaa ttataaccaa tctaagccgc tcaagcaggg   1200

gctcattgcc tgttttacgt gtaactacgt caaacttctc tggcgtagtt acaattatat   1260

gcgttttctc a                                                        1271


<210> SEQ ID NO 6
<211> LENGTH: 1821
<212> TYPE: DNA
<213> ORGANISM: Babesia microti

<400> SEQUENCE: 6

taaaccctaa acccctaaac cctaaaccct aaaccctaaa ccctaaaccc taaaccccta     60

aaccctaaac cctaaaccct aaaccctaaa ccctaaccct aaaccctaaa ccctaaaccc    120

taaaccctaa accctaaccc taaccctaac cctaacccta acctagcctt cattgacgtc    180

tatccccaat cttagaaaaa tcttcaaatc gattctagaa taactggaag caattatcag    240
```

-continued

```
aaattgtata actgcttatt agcttattag cttattagtt aggatgtatg cacattgatg    300

acaactagat gcagcaccac aatcactacc acgtaccaat catataccaa taatgtacta    360

ataatgtacc aataactatg gtttataaag atggtgtcat ttaaatcaat attagttcct    420

tatattacac tctttttaat gagcggtgct gtctttgcag gtgataccga tcgcgaagct    480

ggtgggccta gtggaactgt tgggcctagt gaagctggtg ggcctagtga agctggtggg    540

cctagtgaag ctggtgggcc tagtgaagct ggtgggccta gtgaagctgg tgggcctagt    600

gaagctggtg ggcctagtga agctggtggg cctagtgaag ctggtgggcc tagtggaact    660

ggttggccta gtgaagctgg ttggcctagt gaagctggtt ggcctagtga agctggttgg    720

cctagtgaag ctggttggcc tagtgaagct ggttggccta gtgaacgatt tggatatcag    780

cttctttggt attctagaag aatagttata tttaatgaaa tttatttatc tcatatatac    840

gaacatagtg ttatgatatt ggaacgagat agggtgaacg atggtcataa agactacatt    900

gaagaaaaaa ccaaggagaa gaataaattg aaaaaagaat tggaaaaatg ttttcctgaa    960

caatattccc ttatgaagaa agaagaattg gctagaataa ttgataatgc atccactatc   1020

tcttcaaaat ataagttatt ggttgatgaa atatccaaca aagcctatgg tacattggaa   1080

ggtccagctg ctgatgattt tgaccatttc cgtaatatat ggaagtctat tgtacctaaa   1140

aatatgtttc tatattgtga cttattatta aaacatttaa tccgtaaatt ctattgtgac   1200

aataccatta atgatatcaa gaaaaatttt gacgacatag agaaattggg ctgttttcaa   1260

gctagaagct tcctccctgt taactaatgt attcatggtg ccagaaggtg ctatgcaggt   1320

tgctagggaa tcaaattcat caatagtcct gcccaagagt agtgtgttaa ctggcggtgc   1380

aagatgtgcc ctttgatgca gtagtggcat gcttgtttgt ggggtaaccc agtgctttct   1440

gattgaggtc tactccacag gaggaataga tacctgcttc tgtaaacttg gtcaaaactt   1500

atgactgcac atgaagacag agtggaaaag acctgaaaac acacacgggg tcaggactga   1560

ggaagacagg gttagtatta gagagatttg gggaaaaaaa gagttagcaa atatagagtg   1620

tgatagtcta atggggggat gaatggtatc aaaatgaatt atttatatgt ataaaactga   1680

caatttttta attgtgaaaa ggaatgcaat ccgacccatc tgggggaatt ctagctagca   1740

tcagtgagag aagaggcaag gtgttaggaa atcgtgcaga acatgctcat ccaggcttta   1800

tttctccatt tacatctaga g                                             1821
```

<210> SEQ ID NO 7
<211> LENGTH: 4223
<212> TYPE: DNA
<213> ORGANISM: Babesia microti

<400> SEQUENCE: 7

```
catcacaatt attggctgtt acatcactat agtgctgtat gtaaaaaatt ataaagtgtg     60

acatcattat aatgcaatat gacatcacaa ttatatactg tgacttcact atcttgcact    120

ttaacatcac aattatacat tgtgacatca atatactgca ctatgacatc acgattattg    180

actgtgacat caatacattc tctatgaaca cagttataca ctctgacatc actagcttgc    240

actgtgacat gacaattaaa aactgtgaca tcaatataat ggactgtgac ctacaattat    300

tcactgtgaa accacaacac tgcaattgtg tataattggg atgggtactg atctgctgcc    360

cgaggctcaa tagattacct aggcctcctc actgacaccc acattcaggg ggtcttgatc    420

agtcccatga tggattccca ggctgatgcc tgggattcaa gagttaacct ttgtctggtc    480

agctctttct gggggttaaa cggattaaat gttttaataa taagtcacaa tatagaaaca    540
```

-continued

```
tatttttagg tacaatagac ttccatatat tacggaaatg gtcaaaatca tcagcagctg    600
gaccttccaa tgtaccatag gctttgttgg atatttcatc aaccaataac ttatattttg    660
aagagatagt ggatgcatta tcaattattc tagccaattc ttctttcttc ataagggaat    720
attgttcagg aaaacatttt tccaattctt ttttcaattt attcttctcc ttggtttttt    780
cttcaatgta gtctttatga ccatcgttca ccctatctcg ttccaatatc ataacactat    840
gttcgtatat atgagataaa taaatttcat taaatataac tattcttcta gaataccaaa    900
gaagctgata tccaaatcgt tcactaggcc aaccagcttc actaggccaa ccagcttcac    960
taggccaacc agcttcacta ggccaaccag cttcactagg ccaaccagct tcactaggcc   1020
aaccagcttc actaggccca ccagcttcac taggcccacc agcttcacta ggcccaccag   1080
cttcactagg cccaacagtt ccactaggcc caccagcttc actaggccca ccagcttcac   1140
taggcccacc agcttcacta ggcccaccag cttcactagg cccaccagct tcactaggcc   1200
caccagcttc actaggccca ccagcttcac taggcccaac agttccacta ggcccaccag   1260
cttcgcgatc ggtatcacct gcaaagacag caccgctcat taaaaagagt gtaatataag   1320
gaactaatat tgatttaaat gacaccatct ttataaacca tagttattgg tacattatta   1380
gtacattatt ggtatatgat tggtacgtgg tagtgattgt ggtgctgcat ctagttgtca   1440
tcaatgtgca tacatcctaa ctaataagct aataagctaa taagcagtta tacaatttct   1500
gataattgct tccagttatt ctagaatcga tttgaagatt tttctaagat tggggataga   1560
cgtcaatgaa ggctaggtta gggttagggt tagggttagg gttagggttt agggtttagg   1620
gtttagggtt tagggtttag ggttagggtt tagggtttag ggtttagggt ttagggttta   1680
ggggtttagg gtttagggtt tagggtttag ggtttagggt ttagggttta gggaaggctg   1740
agaaccactg acttagactt tccaagactt tgtcatctta tgacttgccg gttgcctcgt   1800
ttctccacac agcaacctat gttctctctt attacagttt ctgtgggaca tgtcatgctt   1860
ccagcttcga gaatggaagc ctattgtctt aatgggtgag caaagtgggc ccattcatta   1920
atcacagact aatccaaaag gaaatgtgac acctgaccta agtccgacca ataggagcca   1980
ggaaagctca cttctggaat tgtgacttag atatcacgga tgcatacaga ctctttttcc   2040
tgctgaaaca aatggtgagg acctgtccac ccttgtggga agcttgcagt gtaagattct   2100
aatccatatt ggggaaataa ggctgagaag agagagttcc aggccttgtg acagaatcta   2160
atccctggat aaagtctctc tttttacaaa gaacatcagt gttgcaagct ccaaattcct   2220
gttcttactt tcttgagtct gttttcttta tgtataaccc aaagcacttt aactgacaca   2280
gctgtgaagt gagaatattt catagaaatc ctattgtttt gatgtcttct aaaaaagaaa   2340
aaaagcaatg atctgtaaca tttttaact taaataatta gattgattta agtgacatca    2400
aaacatctgg aaaatggtgt ggacacaaat tcactagaga gccatatttt ttgctaacta   2460
attgagaaat taatcactgg caagtctttg gtaaaagtat cacctcagtc atgatctctc   2520
ctgccttcat gacattttcc tcattggtgt gaggatgcta ttctgctttc tatgtgacca   2580
ggaaatagtg ctgtcttctg tctagttatg atttaggttg tacaccaggt tttcacatat   2640
gttccctaac gtctgtagta ggaccaggga ctggttggct tcaagttgtt ggatatggtt   2700
accttaagtc attcatgtac aggaactcat ttgagatgat aggaaatgaa gtgaaagatt   2760
ttcttgcccc tgttaagtaa gataaaaagg attgttatga tggggcagga gcagatctat   2820
ttccaataaa cagaatttga agtgtttgtg tgatattcag atacctcatt gtcatttgaa   2880
```

-continued

```
tgaattactc ctgctctcag tgaagatgtc taagctgcaa ataagaaatg gagagcgctg   2940

tcagaagtca gatggaattg agaatagggg cctggctgca atctgtggag actgcctaaa   3000

gcagctagat aagaaactag cagctgggga gagaaagatc gaatttagtc ggcctgtttt   3060

atattttctt ataaaaaata actgcttcga aatgtttgag aagatagagg caatgagcag   3120

aaagttgttc cttaaatcag ttatagaatg aacacataca cgggcactca gatcaagcca   3180

tgctgagctt gagacaccgg gtgacgcgtg acttgtttat tcccaggctg caaaggagag   3240

taaatgaagt aacgggaagg cccggtgtgg taggcacact cctgcctggc accatctgct   3300

gcttttgtcc ctgttactcc ttgttccttt ccctcctttt ctccctccct tcctccctcc   3360

ctctctccct ccttcacact tctgtcttta tttcctcctg ggagttaatt ggtggtagcc   3420

cctctgtgct gttctttcgg gggtgccttt aatttcgaca atacaatgcc atccatgggg   3480

gcattttata tacagtaata attgtcattg atgtggccat aaggtacttt tttgtggtac   3540

ccttcttgaa cagaacagac acagaagggc gtgcgtgcgt gcgtgcgtgc gtgcgtgcgt   3600

gcgtgtgtgc gtgtgtgcgt gcgtgtgtgc gtgtgtgcgt gcgtgcgtgt gtgcgtgcgt   3660

gcgtgtgtgc gtgtgtgtgt gtgtgtgtgt gtgtgtgtgt gtgtgtgtgt gtgtgttggg   3720

atggggtggg gagcgctagc ttcctacttg ttgtagggtg atgaggtttt atatagtctg   3780

tttctgagac agttaccaaa tccagctggg ttactttttt tttggttttt tatgagacag   3840

ggtttctctg tattgttttg gaggctgtcg gtccagcctg gtctcgaact cacagagatc   3900

cgcctgcctc tgcctcccga gtgctgggat taaaggtgtg cgccaccacc gcccggcccc   3960

agctgggtta cttatcactc agtggatctt tctcttttct ttgtaagaag aactttgcat   4020

tgtgggtcgt catggaagaa cacttggaaa ggtacccttt ctgccccacc cgtttattga   4080

atgagtcttt ttttttttta attaaatagc agaactttgg ggaaagattt agaaaaggcc   4140

cttttcatat tataatacga ggtataggat ggtttaagat aagagacttt ttgttagctg   4200

ttatcagttg agaaaggcac gag                                           4223
```

<210> SEQ ID NO 8
<211> LENGTH: 2287
<212> TYPE: DNA
<213> ORGANISM: Babesia microti

<400> SEQUENCE: 8

```
ttataaacat atctaaatat tttaataata atgatgaaat ttaacataga taagataata     60

ttaatcaatt taatagtatt attgaatcga aatgtagtgt attgtgtgga tacaaataat    120

agttcattaa ttgaatcaca accagtaaca actaacattg acactgataa tacaattaca    180

acaaataaat acactggtac tataattaat gccaatattg ttgagtaccg tgaatttgag    240

gatgaacctt taacaatagg gtttagatac actatagata aatcacaaca aaataaatta    300

tcacatccaa ataaaattga taaaatcaaa ttttctgatt atataattga atttgatgac    360

aatgctaaat taccaactga taatgttatt tgtatatcca tctatacttg caagcataat    420

aatccagtat taattagatt ctcatgttct atagaaaaat attactacca ttacttctac    480

tcaatgaata atgatacaaa taaatggaat aatcacaaat taaaatatga taaaacatac    540

aatgaatata ctgacaataa tggtgttaat tattataaaa tctattatag tgataaacag    600

aattccccta ctaatggaaa tgaatatgag gatgtagcat tagcaagaat acattgtaat    660

gaagaaagat gtgcaaatgt aaaggtagat aaaattaaat ataagaattt ggaaatttat    720

gtgaaacagt taggtactat aattaatgcc aatattgttg agtaccttgt atttgaggat    780
```

-continued

```
gaacctttaa caatagggtt tagatacact atagataaat cacaacaaaa tgaattatca     840
catccaaata aaatttataa aatcaaattt tctgattata taattgaatt tgatgatgat     900
gctaaattaa caacaattgg tactgttgaa gatataacca tctatacttg caagcataat     960
aatccagtat taattagatt ctcatgttct atagaaaaat attactacta ttacttctac    1020
tcaatgaata ataatacaaa taaatggaat aatcacaact taaaatatga taatagattc    1080
aaagaacata gtgacaagaa tggtattaat tattatgaaa tctcagcttt caaatggagt    1140
ttctcttgtt ttttcgttaa taaatatgag cataaagaat tagcaagaat acattgtaat    1200
gaagaaagat gtgcaaatgt aaaggtagat aaaattaaat ataagaattt ggaaatttat    1260
gtgaaacagt taggtactat aattaatgcc aatattgttg agtaccttgt atttgaggat    1320
gaacctttaa caatagggtt tagatacact atagataaat cacaacaaaa tgaattatca    1380
catccaaata aaatttataa aatcaaattt tctgattata taattgaatt tgatgatgat    1440
gctaaattaa caacaattgg tactgttgaa gatataacca tctatacttg caagcataat    1500
aatccagtat taattagatt ctcatgttct atagaaaaat attactacta ttacttctac    1560
tcaatgaata ataatacaaa taaatggaat aatcacaact taaaatatga taatagattc    1620
aaagaacata gtgacaagaa tggtattaat tattatgaaa tctcagcttt caaatggagt    1680
ttctcttgtt ttttcgttaa taaatatgag cataaagaat tagcaagaat acattgtaat    1740
gaagaaaaat gtgtaaatgt aaaggtagat aacattggga ataaaaattt ggaaatttat    1800
gtgaaataat ttaatgaagt ataatattat ttataataat tcaaagatta atataattaa    1860
ttattataat tacaaaaata attaattgta gaatattata ttattaatca attcagatta    1920
taaatacata tttttacata catttcaatt taaacattca aattaatgtc atttttatct    1980
acattattat aattataact ataatattca ttaaatacta tttaaaaaaa tatcctctac    2040
attatatcaa tcaatataat atacaattat ataatatatt cacaatgtat aacaatcaac    2100
cctaacatgt acatacataa tatcattact aatcaatatt taattaataa aatatttaat    2160
agtcatctgt aatataatca ttgtatacta atttattata aattattaca aaatacactc    2220
ttttacttca ttttatttct gttaaatttc atattctaat attatattca tctttctcat    2280
gttactt                                                              2287
```

<210> SEQ ID NO 9
<211> LENGTH: 2784
<212> TYPE: DNA
<213> ORGANISM: Babesia microti

<400> SEQUENCE: 9

```
cactgctttc gcagcgtttc ttgcttttgg gaatatctca cctgtacttt ctgctggtgg      60
tagtggtggt aatggtggta atggtggtgg tcatcaagag caaaataatg ctaatgatag     120
tagtaatccc accggagccg gtggacaacc caataacgaa agtaagaaaa aggcagtaaa     180
acttgacttg gacctcatga aagaaacaaa gaatgtttgc accactgtta atactaaact     240
agtcggaaaa gcaaagagca aattaaacaa attagaaggt gaatcccata aggagtatgt     300
agctgagaaa acgaaggaga tagatgagaa aaataagaaa tttaacgaga atcttgttaa     360
aatagagaaa aagaagaaaa ttaaggttcc tgccgatact ggtgctgaag tggatgctgt     420
tgatgatggt gttgcgggtg cactatccga tttatcctcc gatatctccg ctattaagac     480
tctcaccgac gatgtatccg agaaggtttc tgaaaacttg aaagatgatg aggccagtgc     540
```

-continued

```
aacagaacac actgatataa aagaaaaagc caccctgctt caagagtctt gcaacggaat    600

tggcactatc ctagataagt tggccgaata tttaaataat gatacaactc aaaatatcaa    660

gaaagaattt gatgaacgca agaagaatct cacctctttg aagacaaagg tagaaaataa    720

ggatgaagat tatgttgatg ttaccatgac atcaaaaaca gatctgataa tacactgttt    780

aacttgcaca aacgatgcac acggactgtt tgatttcgaa tcgaagagct tgataaaaca    840

aacctttaaa ttgaggtcca aagatgaagg tgaactctgc taatttagat tttagatggg    900

ccatgtatat gttaaacagc aagattcatc ttatagaaag cagtttgatc gataacttca    960

ccttggataa tccatccgca tacgaaattt tacgcgtttc ttataactca aatgaatttc   1020

aagtacaatc accgcagaac attaacaatg aaatggaatc ttcaacgccc gaatccaata   1080

tcatttgggt tgtacatagt gatgttataa tgaaaaggtt caactgtaaa aatcgcaaat   1140

ctctcagtac tcattcactc actgaaaatg atattctcaa gtttggccgt atagaactct   1200

ctgttaaatg tataattatg ggcgcaggta tcactgcatc tgatcttaat ctaaagggat   1260

tggggtttat tagtccagat aaacaatcaa ctaatgtatg taactatttt gaagatatgc   1320

atgaatctta tcatattctt gatacacaaa gggcctcgga ttgtgtatca gatgatggcg   1380

ctgatattga tatatccaac ttcgacatgg tccaagacgg taacataaat tctgttgacg   1440

ctgattctga aacatgtatg gcaaactctg gcgtaacggt caataatact gaaaatgtta   1500

gtaatagtga gaattttgga aaattaaaat cattggtaag caccaccact cctttgtgcc   1560

gtatttgcct gtgtggtgaa tcagaccctg ggccactagt aaccccttgc aattgcaagg   1620

ggtccctaaa ttatgtccat cttgaatgcc taaggacttg gattaaaggg cggttgtcaa   1680

ttgtgaagga tgatgatgct tcctttttct ggaaagagct atcatgtgag ctatgcggga   1740

agccgtatcc atcggtccta caagtagatg atacagagac taatttgatg gatataaaaa   1800

aaccggatgc accatatgtg gtattggaaa tgagatcaaa ttctggtgat gggtgtttcg   1860

ttgtttctgt agctaaaaat aaggcgatta ttggacgggg gcatgaaagt gacgttaggt   1920

tgagtgatat ttcagtgtca cgaatgcatg cttctttgga attggatggt ggaaaagtag   1980

tgatacatga ccagcaatct aagtttggta cactcgttag ggccaaagcg cctttttcaa   2040

tgcctataaa gggtcccatc tgtctacagg taagcatttt ctttttgaac ttgaaaatat   2100

ctactcatag tctaaccatg gagaggggca tggaacatgt ccttctctaa tatttccaaa   2160

aaggatctat gcctgataac cttggtattg aaggtggctt tctcaaagtg agacattcca   2220

tttctgttgt tggagctatc ctatctgagg ttagtgttct ggtaaacatt cctagaaaac   2280

tcataaagca gaaatctgtg tgtatactaa attgcacaga gaactccacg tgtgtgctag   2340

acttcacaga gaactctgtg tgtgtgctaa actgcataga gaagaacatg ttgagtgcat   2400

catggttgag ggaaattgct ttatataaaa gatttatttt cctaaggtaa cttaggatta   2460

atttttctga aagcttagtt ttggtgagca caattgtgat ctttgtttct cagatggtcg   2520

ggaaggcact cccagaaagc aggtggatac acactacact gcatgctaca ctctgtagac   2580

taggagtatc gttttcacac ttatgaaata gtcaccatgc tgggcacaaa tatcttttta   2640

tacaccatat attgttcatg ttcaggtcca catttcaatt tgtatgtgaa aagcatccgg   2700

ggctgtctga taaacacata gaaatgaagg aaacagtgta tgtaactgaa gccttcagtc   2760

ctttgcaatt tctttgattc ttag                                          2784
```

<210> SEQ ID NO 10
<211> LENGTH: 3701

-continued

<212> TYPE: DNA
<213> ORGANISM: Babesia microti

<400> SEQUENCE: 10

```
acctatttat aatatagtat attactggtt tgttttaaat cgaaaaaatg tattgtattt     60

aagaatgaaa ttatttattt atcatgatta tcatatttct aaatattaaa atctagtaac    120

ggttgcttga atatttattt aaattatatg tagtagtatt aaaatgtgtt atatataagt    180

agtgttctaa atcatcatta gtaatattgt ataaattaat tgtaaaaatt gcgatactac    240

aattaatcaa caattaaaat atatcagtat agataattta aataaataat tagataagat    300

cttaaggatt aaatgacgaa tttagaatga taaataatca tcataggcat ttgttataat    360

atcattaatt atattcatgt ggttataatt ataaaagtat atatagtttt gtaattgtaa    420

tgatataaaa ttagaacaga tataattaat aattcaaata ttatattaat tttattatat    480

atgattatta ttgatattta tataattaca tattgttatt gtatcattta atgattatat    540

atcaatatcc atatatatat ataataattg aattataatt aaattaattg gcatattaca    600

tttataataa tatattatta gtcaatatga catcatatta tattatccat catgattgtg    660

aatgtaacta gaacattgat tattatatta aatcacatat taatactgat tataataata    720

tcattgataa tctaataata tagtattatc tctaataata ttgtattatc tctaatatta    780

tggtataata gatactgtga aaataaattc aactggagat aaggaaacca ttttgtatag    840

atattttata caaattatta tgaaataatc taaataaatg acaaaaaatc gattatacaa    900

atcacattaa tgacaaacaa acttgtatac atatattgat taacattaca aaactaaatt    960

ataatattta gattgataat tgttataata cttaacaata ttctactttt taatataatt   1020

ttttattcaa taatatactc tttcatattt tgtactattt tatataatca tatatattat   1080

ataattatat atatttgata attgaatata tcaataatga tgatatacat gaatatgcat   1140

atatacccca tataatgtta ttatatttag tgcttacatt attaattata aatatattta   1200

aataattaaa taataatgaa aattaacata gacaatataa tattaatcaa tttgataata   1260

ttattgaatc gtaatgtagt atattgtgtg gataaaaatg atgtttcatt atggaaatca   1320

aaacctataa caactgtcag taccactaat gatactatta caaataaata cactagtact   1380

gtaattaatg ccaattttgc tagctaccgt gaatttgagg atagggaacc tttaacaata   1440

ggatttgaat acatgatcga taaatcacaa caagataaat tatcacatcc aaataaaatt   1500

gataaaatca aaatttctga ttatataatt gaatttgatg acaatgctaa attaccaact   1560

ggtagtgtta atgatatatc catcattact tgcaagcata ataatccagt attaattaga   1620

ttctcatgtt taatagaagg atctatctgc tattatttct acttattgaa taatgataca   1680

aataaatgga ataatcacaa attaaaatat gataaaacat acaatgaaca tactgacaat   1740

aatggtatta attattataa aatcgattat agtgaatcta cagaacctac taccgaatct   1800

actacctgtt tttgttttcg caaaaaaaat cataaatctg agcgtaaaga attagaaaat   1860

tataaatatg agggtacaga attagcaaga atacattgta ataaagggaa atgtgtaaaa   1920

ttgggtgaca ttaagataaa ggataagaat ttggaaattt atgtgaaaca gttaatgtct   1980

gtaaatactc cagtaaattt tgacaaccct acatcgatta atctaccaac tgtcagtact   2040

accaatgata ctattacaaa taaatacact ggtactataa ttaatgccaa tattgttgag   2100

tactgtgaat ttgaggatga acctttaaca atagggttta gatacactat agataaatca   2160

caacaaaata aattatcaca tccaaataaa attgataaaa tcaaattttt tgattatata   2220
```

-continued

```
attgaatttg atgatgatgt taaattacca acaattggta ctgtcaatat tatatatatc   2280

tatacttgcg agcataataa tccagtatta gttgaattta tagtttctat agaagaatct   2340

tactactttt acttctactc aatgaataat aatacaaata aatggaataa tcacaaatta   2400

aaatatgata aaagattcaa aaaatatact aagaatggta ttaattgtta tgaatatgta   2460

cttcgtaaat gcagttctta tactcgtaaa aatgaatatg agcataaaga attagcaaga   2520

atacattgta atgaagaaaa atgtgtaaat gtaaaggtag ataacattga gaaaaagaat   2580

ttggaaattt atgtaaaata atttaacgaa gtgtaatatg taaaatagtt taatgaagta   2640

taatattatt taaaataatt caaaatttca gaaattaata taattaatta ttataaatac   2700

aaaataatta attacaaatg tgtattgtta gttatttcag attgtaaata catattttac   2760

atacattttt attaaaactt tcaaattaat attttcattt ttataagcat tattataatt   2820

atatactata attatcagtc atcaaataat atccaaagtt atcctctaca ttatatcaat   2880

catacagtat acaattatat aaaatattaa caacatataa caaccaacat taatatatac   2940

ataatatctt tattaatcaa tatttaatca atacaataat taatagttaa ctaactatac   3000

acatagtgta tactaaatta ttataaatta tatgttataa ttacaaaaac gtcatttact   3060

tattttattt cagttatgtt tcatagtcta atttagattt ggtgaaacgc atctggctga   3120

tgtgctggtg agcaagcagt tccacgaagc aaacaatatg actgatgcgc tggcggcgct   3180

ttctgcggcg gttgccgcac agctgccttg ccgtgacgcg ctgatgcagg agtacgacga   3240

caagtggcat cagaacggtc tggtgatgga taaatggttt atcctgcaag ccaccagccc   3300

ggcggcgaat gtgctggaga cggtgcgcgg cctgttgcag catcgctcat ttaccatgag   3360

caaccccgaa ccgtattcgt tcgttgattg gcgcgtttgc gggcagcaat ccggcagcgt   3420

tccatgccga agatggcagc ggttacctgt tcctggtgga aatgcttacc gacctcaaca   3480

gccgtaaccc gcaggtggct tcacgtctga ttgaaccgct gattcgcctg aaacgttacg   3540

atgccaaacg tcaggagaaa atgcgcgcgg cgctggaaca gttgaaaggg ctggaaaatc   3600

tctctggcga tctgtacgag aagataacta aagcactggc ttgataaata accgaatggc   3660

ggcaatagcg ccgccattcg ggaatttac ccctgttttc t                         3701
```

<210> SEQ ID NO 11
<211> LENGTH: 1287
<212> TYPE: DNA
<213> ORGANISM: Babesia microti

<400> SEQUENCE: 11

```
ctcgtgccgc tcgtgccgat tattataaat atttagttga tgaatatagt tctcccaggg     60

aggaaagaga attagcaaga gtacattgta atgaagaaaa atgtgtaaaa ttggatggca    120

ttaagtttaa ggataagaat ttggaaattt atgtgaaaca gttaatgtct gtaaatactc    180

cagttgtatt tgacaacaat acattgatta atccaactag cagcagtggt gccactgatg    240

acataacata tgaattatcg gtggaatcac aacctgtacc aactaacatt gacacaggta    300

ataatattac aacaaataca tcaaataata atctaattaa agctaaattt ctttataatt    360

ttaatcttcc tggtaaacct tcaacaggac tatttgaata cactatagat aaatcagaac    420

aaaataaatt atcacatcca aataaaattg ataaaatcaa attttctgat tatataattg    480

aatttgatga tgatgctaaa ttaccaacaa ttggtactgt caatattata tccatcatta    540

cttgcaagca taataatcca gtattagttg aatttatagt ttctacagaa atatattgct    600

actacaatta cttctactca atgaataata atacaaataa atggaataat cacaaattaa    660
```

-continued aatatgataa aagatataaa gaagaatata cagatgataa tggtattaat tattataaat 720
taaatgatag tgaacctact gaatctacag aatctactac ctgtttttgt tttcgcaaaa 780
aaaatcataa atatgaaaat gagcgtacag cattagcaaa agaacattgc aatgaagaaa 840
gatgtgtaaa ggtagataac attaaggata ataatttgga aatttatcta aaataattta 900
acgaagtata atattattta taataattca aaatttcaga aattaatata attaattatt 960
ataaatacaa aataattaat tacaaatgtg tattgttagt tatttcagat tgtaaataca 1020
tattttacat acatttttat taaaactttc aaattaatat tttcattttt ataagcatta 1080
ttataattat atactataat tatcagtcat caaataatat ccaaagttat cctctacatt 1140
atatcaatca tacagtatac aattatataa aatattaaca acatataaca accaacatta 1200
atatatacat aatatcttta ttaatcaata tttaatcaat acaataatta atagttaact 1260
aactatacac atagtgtata ctaaatt 1287

<210> SEQ ID NO 12
<211> LENGTH: 572
<212> TYPE: DNA
<213> ORGANISM: Babesia microti

<400> SEQUENCE: 12
cttcattgac gtctatcccc aatcttagaa aaatcttcaa atcgattcta gaataactgg 60
aaacaattat cagaaattgt ataactgctt attagcttat tagcttatta gttaggatgt 120
atgcacattg atgacaacta gatgcagcac cacaatcact accacgtacc aatcatatac 180
caataatgta ctaataatgt accaataact atggtttata aagatggtgt catttaaatc 240
aatattagtt ccttatatta cactcttttt aatgagcggt gctgtctttg caagtgatac 300
cgatcccgaa gctggtgggc ctagtgaagc tggtgggcct agtgaagctg gtgggcctag 360
tggaactgtt gggcccagtg aagctggtgg gcctagtgaa gctggtgggc ctagtggaac 420
tggttggcct agtgaagctg gtgggcctag tgaagctggt gggcctagtg gaactggttg 480
gcctagtgaa gctggttggt ctagtgaacg atttggatat cagcttcttc cgtattctag 540
aagaatagtt acatttaatg aagtttgttt at 572

<210> SEQ ID NO 13
<211> LENGTH: 2338
<212> TYPE: DNA
<213> ORGANISM: Babesia microti

<400> SEQUENCE: 13
ctcgtgccga atcttagaaa aatcttcaaa tcgattctag aataactgga aacaattatc 60
agaaattgta taactgctta ttagcttatt agcttattag ttaggatgta tgcacattga 120
tgacaactag atgcagcacc acaatcacta ccacgtacca atcatatacc aataatgtac 180
taataatgta ccaataacta tggtttataa agatggtgtc atttaaatca atattagttc 240
cttatattac actcttttta atgagcggtg ctgtctttgc aagtgatacc gatcccgaag 300
ctggtgggcc tagtggaact gttgggccca gtgaagctgg tgggcctagt gaagctggtg 360
ggcctagtgg aactggttgg cctagtgaag ctggtgggcc tagtgaagct ggtgggccta 420
gtggaactgg ttggcctagt gaagctggtt ggtctagtga acgatttgga tatcagcttc 480
ttccgtattc tagaagaata gttacattta atgaagtttg tttatcttat atatacaaac 540
atagtgttat gatattggaa cgagataggg tgaacgatgg tcataaagac tacattgaag 600

-continued

```
aaaaaaccaa ggagaagaat aaattgaaaa aagaattgga aaaatgtttt cctgaacaat    660

attcccttat gaagaaagaa gaattggcta gaatatttga taatgcatcc actatctctt    720

caaaatataa gttattggtt gatgaaatat caaacaaggc ctatggtaca ttggaaggtc    780

cagctgctga taattttgac catttccgta atatatggaa gtctattgta cttaaagata    840

tgtttatata ttgtgactta ttattacaac atttaatcta taaattctat tatgacaata    900

ccattaatga tatcaagaaa aattttgacg aatccaaatc taaagcttta gttttgaggg    960

ataagatcac taaaaaggac gtgtatgtaa atgatcacta aacgggctcc acatatctat   1020

tactggggta gatattataa gttatggata agtaaattta tggcgataga ttccaacaaa   1080

tttgtggtta gtagcgacaa tgattatggc tagtgtgtgg agtacttatg agtgaatgat   1140

tgtagtggtg gctagcagtg agtatagtta ggtaatccct acacacccat ttaaataaga   1200

tgcaaatagc atttaaattg acatatattg tgtgtatgtc cacgtttatt gcgtttccat   1260

gacgtatctg ctgaggtgtg tcttgtgtat ctaagtacca gacacagcac ttaaattgtt   1320

atgggcatga cgatggatgt taaaggttta tacactccaa aggcacgttc ttctgctagg   1380

gaaacgaggg acaagttcga ttttgctata caaagcaagt ttcactccct ggactttaca   1440

ctggatgact ttgatatagg tgcattcgtg gtaaacctca aaatttactc agggcgatgg   1500

tgcccatggg caggtttttt tggcaaggga acgacgtacc ggttttattt gcgtgttaaa   1560

atgcattttt aaatcacaac ttgtgaagta attgcctaat aatcacacag aaatggacag   1620

gaagctattt tcaagcggga aatcgaattg cacgggcatc tgagacatcc aaacatagca   1680

tggtatgtac atatttatcc agcttgtata cctggttcac tagccctact atgatattca   1740

tagtgatgga atattgttac aatggcgatc tatttaatta tatgtcaaaa catggccaac   1800

tgagtgaaga aagggtatca gagtatacag atatttacat agaattttgt tcgaagtcat   1860

ttgggccatt agaagctgcc acgacaaacg catagcgcac ttggatatta aaccagtaag   1920

gttctatgtt acagaggaga atatattatt ggaccatgaa aacaggtgta aattggcgga   1980

ctttggattc tctgcacaca tagggcattt gtaccgctca aacggagtgc tcatcatcgt   2040

ggcacgcatg gtaacacgca attwatggca gattattggt ctccggagca gtgtgccaaa   2100

catttgggtc tggggttgaa gtatggggag tatgatgaac aaagcgacat atgggcgttg   2160

ggcatattgg cagttgaatt gtttattgga taccctccat ttggatctac tactgaagag   2220

cccaacaatg tgattatgaa cagaatccac acttaccact ggaccaaaca tgtactttta   2280

tctattacgc agatttttga aatgaagagg gaaaaacatc tactctcgtc gacgcctg     2338
```

<210> SEQ ID NO 14
<211> LENGTH: 729
<212> TYPE: DNA
<213> ORGANISM: Babesia microti

<400> SEQUENCE: 14

```
ttgcctggac cttctctgtc ctagaattac aggaattctc ttatactgtt taatacaaaa     60

cacttggaag aatttcacca attgcatatg aaacatggaa tccaagagac caaaatttaa    120

aaccttgaaa tagaagcact tatgccaata ttggaaatta cttagtgaag tgatccaaag    180

tactgatttg gtcagaagac atcaccaggg cactagctgg cctagtgacc tgagtatttg    240

tgaaagctga ttttaatgtt gagaacatga aggaagcagt attgaggtaa tggaatcttg    300

tagattatag tagaagccaa ctgagaccaa gaaatgtacg gtaggaatga aataaggtct    360

tgggtggtca ttgcatggag ctgtgaaagt gaagcgttgt tggggtatag attcgcaagt    420
```

-continued

```
cttggggcat gactatgtgg ggttaccaag gttaggttaa ctgaggtgga aagatccact    480

ctaaatgggg gagttaccat ttcatgtgct gggatcccag agatgtcaaa ggagaaaata    540

agctattgaa taagagcatc tatatccctt gcttcttggc tatggatgtt atgtgactag    600

tcatctctta gtcttacctt caccattata acaagatttt ctagaacttt gggttaaatt    660

aaatccttta ttcctcacgt tgctgtctta gttactttcc tgttgctttg ataaagcatt    720

ctggccaag                                                            729


<210> SEQ ID NO 15
<211> LENGTH: 1448
<212> TYPE: DNA
<213> ORGANISM: Babesia microti

<400> SEQUENCE: 15

acatgttgac ttttggaaat atacgttttc ataatataaa tctcccacca ttttcattgg     60

gcataattca ctcgattacg gtagaaaagg cgattaactc tgaagatttt gacggaatac    120

aaacactttt acaagtgtct atcattgcta gttacggtcc atctggcgat tacagtagtt    180

ttgtgttcac tccagttgta acagcagaca ccaacgtttt ttacaaatta gagacggatt    240

tcaaacttga tgttgatgtt attactaaga catcactaga attgcccaca agtgttcctg    300

gctttcacta caccgaaact atttaccaag gcacagaatt gtcaaaattt agcaagcctc    360

agtgcaaact taacgatcct cctattacaa caggatcggg gttgcaaata atacatgatg    420

gtttgaataa ttcgacaatt ataaccaaca aagaagttaa tgtggatgga acagatttag    480

tttttttga attgctccct ccatcggatg gcattcccac cttgcgatca aaattatttc    540

ccgtcctgaa atcaattcca atgatatcta ccggggttaa tgaattactg ttggaagtac    600

tcgagaaccc ctctttccct agtgcaatta gcaattacac cggactgaca ggccgactta    660

acaaattact tacagtttta gacggtattg ttgatagcgc cattagtgtc aagactacag    720

aaactgtccc tgacgacgca gaaacttcta tttcttcatt gaaatcattg ataaaggcaa    780

tacgagataa tattactacc actcgaaacg aagttaccaa agatgatgtt tatgcattga    840

agaaggccct cacttgtcta acgacacacc taatatatca ttcaaaagta gatggtatat    900

cattcgacat gctgggaaca caaaaaaata aatctagccc actaggcaag atcggaacgt    960

ctatggacga tattatagcc atgttttcga atcccaatat gtatcttgtg aaggtggcgt   1020

acttgcaagc cattgaacac atttttctca tatcaaccaa atacaatgat atatttgatt   1080

acaccattga ttttagtaag cgtgaagcta ctgattctgg atcatttacc gatatattgc   1140

tcggaaacaa ggtgaaggaa tctttgtcat ttattgaggg tttgatttct gacataaaat   1200

ctcactcatt gaaagctggg gttacaggag gtatatcaag ttcatcatta tttgatgaaa   1260

tcttcgacga gttaaatttg gatcaagcaa caattagaac ccttgttgca ccattagatt   1320

ggccacttat ctcagacaaa agcctccacc cttcactgaa gatggttgtg gtcctgccag   1380

gatttttcat agttccttaa taacatgaca tttcatagtc ccttcagtcc tgatgacaag   1440

acggtgaa                                                            1448


<210> SEQ ID NO 16
<211> LENGTH: 1350
<212> TYPE: DNA
<213> ORGANISM: Babesia microti

<400> SEQUENCE: 16
```

-continued gcctaagccc aaatgggatt taagcaggag gggataaaac agatgacctc caccatgccc 60
tactaactct aagctaagga aatccagcct gctggctatt tacctgcttt cctcgaagtg 120
aaaggccaga gtcaccccca atctttccca aaagattgaa gtcactctct ccatgccggc 180
aaaggtagat ggtgcgaggc tggacatgga tattcataag gtagtagaca attttactct 240
ggatgtagtc ctggactctg ttgaccagaa atctctggcc tacattaatc accttgatga 300
agacagatcc ctaggacaga gtagaaagag caattttatg gtcagaaaat ctgaaactag 360
gagtgtggca agcaaggggg caaggctatc agcacctagt gacaatccca gcacttagaa 420
ggcttagctg gaaggggctt aggtttgacc ctgactcaag acaaatgaac atatgaaaag 480
tatggggaga atgatctgtg tattgactgg tagggcctca tcagctattc cttctctccc 540
tgtcactgcc atctcgtgcc gaattcggca cgagctcgtg ccgaaaccct aaaccctaaa 600
cccctaaacc ctaaacccta aaccctaaac cctaaaccct aaaccctaaa ccctaaaccc 660 taaacccta aacccctaaa ccctaaaccc taaaccctaa accctaaacc ctaaacccta 720
aaccctaacc ctaaccctaa ccctaaccct aacctagcct tcattgacgt ctatccccaa 780
tcttagaaga atcttcaaat cgattctaga ataactggaa acaattatca gaaattgtat 840
aactgcttat tagcttatta gcttattagt taggatgtat gcacattgat gacaactaga 900
tgcagcacca caatcactac cacgtaccaa tcatatacca ataatgtact aataatgtac 960
caataactat ggtttataaa gatggtgtca tttaaatcaa tattagttcc ttatattaca 1020
ctctttttaa tgagcggtgc tgtctttgca agtgataccg atcccgaagc tggtgggcct 1080
agtgaagctg gtgggcctag tggaactgtt gggcccagtg aagctggtgg gcctagtgaa 1140
gctggtgggc ctagtggaac tggttggcct agtgaagctg gtgggcctag tgaagctggt 1200
gggcctagtg aagctggtgg gcctagtgaa gctggtgggc ctagtggaac tggttggcct 1260
agtggaactg gttggcctag tgaagctggt tggtctagtg aacgatttgg atatcagctt 1320
cttccgtatt ctagaagaat agttatattt 1350

<210> SEQ ID NO 17
<211> LENGTH: 1820
<212> TYPE: DNA
<213> ORGANISM: Babesia microti

<400> SEQUENCE: 17
ggaaagcctt aaacatgcat gggaataatg aaatagtaaa aattgcagcc atggcaatgt 60
aataatgagt ggatgtttca gtcttgaggc tctttaacaa gagtgttgtc ttgtagtcaa 120
agacaaagtg attcgtcatg ccgcattcgc agccaccatc atcatcaggc gacgacgggt 180
ctctttcatt atcctcgggc ttattattgc aaccatgaca cccttcttta caaaagtctt 240
tttttttcag cggtgtctga gtattatgcg attttattcc agccttccca cttttattct 300
tattgagatt gccatgctct tcttcatgag cgtcacttgt ttcctgcggt gtctgagtat 360
catacgattt tattccagca tttccacttt tattcttatt gattttgtca tgcccttctt 420
cacactcttc acatatttct tgcgttgtct gagtatcatg cgattttctt tcagccttct 480
cacttttatt cgtattgatt ttgtcatgcc cttcttcatg agcgtcactt gtttcctgcg 540
gtgtctgagt atcatacgat tttattccag catttccact tttattctta ttgattttgt 600
catgcccttc ttcacactct tcacatattt cttgcgttgt ctgagtatca tacgatttta 660
ttccagcatt tccactttta ttcttattga ttttgtcatg cccttcttca cactcttcac 720
atatttcttg cgttgtctga gtatcatgcg attttctttc agccttctca cttttattcg 780

-continued

```
tattgggttt gccatgccct tctttacgct cttcatatat ttcttgtgcc gttagtctca    840

gtaagttgtc aagctcttca tatatttctt gcggtgtctg agtatcatgc gattttcttt    900

cagtcttctc acttttattc gtattgagtt tgccattccc ttcttcatga tcgtcacttg    960

tttcttgcgc cgttagtctc attaagttgt caagctcttc atcatctatt gaatggtatg   1020

gagctgtatc ttcccagggt ggttgaatta tgtcattctc gccgatttta aatgatggtt   1080

cttcatcatt tatatcagat gccatgtctg agtggtgccc taatctagag aattggtgtg   1140

gtaccccctc atccaaactt tcgggcaaca ccctggtatc agaatccatt tgttcgagcg   1200

gctcactatc gcaagcgtct tgtggattga tgttatcatg ttcctggatt tcaacatgta   1260

cagattctga atccgcattg ggttctggaa tatagttggt aactacattt gtttctagag   1320

aagtatcatt cttatattaa ttcatctaag atctgtgctt ctttgtttct acacatacag   1380

ggtgtctctt ttcccaacat aatatctgta aattcttccc agaagcagaa ccttgttggt   1440

accagacagc atcgggtctc tgtgagtttc tattcaggca acaggtgtat tctgtttgcc   1500

agtccaagtg catcctgtat tctagtactg gcttactacc ccaagcaaat cactggcatc   1560

aacatctagc actgagtgaa gcatgatctc ttctacaagg tgtttttcca ttgtgttgta   1620

agcccgtata caaggctgtt cccactcaac aatgaagaga cctcttagca tgaatggcca   1680

gatgtctgtt ctttaaatta aatcaatatg ttttgctcaa tatgtcagac ttgtttgtgg   1740

tggagccaaa attggaggtc ccatcgagat ttggagaaac ttgaaatgaa tgcaaaagat   1800

ggtgggggct actcgtgccg                                               1820
```

<210> SEQ ID NO 18
<211> LENGTH: 263
<212> TYPE: PRT
<213> ORGANISM: Babesia microti

<400> SEQUENCE: 18

```
Leu Phe Leu Met Ser Gly Ala Val Phe Ala Ser Asp Thr Asp Pro Glu
 1               5                  10                  15

Ala Gly Gly Pro Ser Glu Ala Gly Gly Pro Ser Gly Thr Val Gly Pro
            20                  25                  30

Ser Glu Ala Gly Gly Pro Ser Glu Ala Gly Gly Pro Ser Gly Thr Gly
        35                  40                  45

Trp Pro Ser Glu Ala Gly Gly Pro Ser Glu Ala Gly Gly Pro Ser Glu
    50                  55                  60

Ala Gly Gly Pro Ser Glu Ala Gly Gly Pro Ser Gly Thr Gly Trp Pro
65                  70                  75                  80

Ser Gly Thr Gly Trp Pro Ser Glu Ala Gly Trp Ser Ser Glu Arg Phe
                85                  90                  95

Gly Tyr Gln Leu Leu Pro Tyr Ser Arg Arg Ile Val Ile Phe Asn Glu
            100                 105                 110

Val Cys Leu Ser Tyr Ile Tyr Lys His Ser Val Met Ile Leu Glu Arg
        115                 120                 125

Asp Arg Val Asn Asp Gly His Lys Asp Tyr Ile Glu Glu Lys Thr Lys
    130                 135                 140

Glu Lys Asn Lys Leu Lys Lys Glu Leu Glu Lys Cys Phe Pro Glu Gln
145                 150                 155                 160

Tyr Ser Leu Met Lys Lys Glu Glu Leu Ala Arg Ile Phe Asp Asn Ala
                165                 170                 175

Ser Thr Ile Ser Ser Lys Tyr Lys Leu Leu Val Asp Glu Ile Ser Asn
```

-continued

```
            180                 185                 190

Lys Ala Tyr Gly Thr Leu Glu Gly Pro Ala Ala Asp Asn Phe Asp His
        195                 200                 205

Phe Arg Asn Ile Trp Lys Ser Ile Val Leu Lys Asp Met Phe Ile Tyr
    210                 215                 220

Cys Asp Leu Leu Leu Gln His Leu Ile Tyr Lys Phe Tyr Tyr Asp Asn
225                 230                 235                 240

Thr Val Asn Asp Ile Lys Lys Asn Phe Asp Glu Ser Lys Ser Lys Ala
                245                 250                 255

Leu Val Leu Arg Asp Lys Ile
            260


<210> SEQ ID NO 19
<211> LENGTH: 310
<212> TYPE: PRT
<213> ORGANISM: Babesia microti

<400> SEQUENCE: 19

Met Ser Gly Ala Val Phe Ala Ser Asp Thr Asp Pro Glu Ala Gly Gly
 1               5                  10                  15

Pro Ser Glu Ala Gly Gly Pro Ser Gly Thr Val Gly Pro Ser Glu Ala
            20                  25                  30

Gly Gly Pro Ser Glu Ala Gly Gly Pro Ser Gly Thr Val Gly Pro Ser
        35                  40                  45

Glu Ala Gly Gly Pro Ser Glu Ala Gly Gly Pro Ser Gly Thr Gly Trp
    50                  55                  60

Pro Ser Glu Ala Gly Gly Pro Ser Glu Ala Gly Gly Pro Ser Gly Thr
65                  70                  75                  80

Val Gly Pro Ser Glu Ala Gly Gly Pro Ser Glu Ala Gly Gly Pro Ser
                85                  90                  95

Gly Thr Gly Trp Pro Ser Glu Ala Gly Gly Pro Ser Glu Ala Gly Gly
            100                 105                 110

Pro Ser Glu Ala Gly Gly Pro Ser Glu Ala Gly Gly Pro Ser Gly Thr
        115                 120                 125

Gly Trp Pro Ser Gly Thr Gly Trp Pro Ser Glu Ala Gly Trp Ser Ser
    130                 135                 140

Glu Arg Phe Gly Tyr Gln Leu Leu Pro Tyr Ser Arg Arg Ile Val Ile
145                 150                 155                 160

Phe Asn Glu Val Cys Leu Ser Tyr Ile Tyr Lys His Ser Val Met Ile
                165                 170                 175

Leu Glu Arg Asp Arg Val Asn Asp Gly His Lys Asp Tyr Ile Glu Glu
            180                 185                 190

Lys Thr Lys Glu Lys Asn Lys Leu Lys Lys Glu Leu Glu Lys Cys Phe
        195                 200                 205

Pro Glu Gln Tyr Ser Leu Met Lys Lys Glu Glu Leu Ala Arg Ile Phe
    210                 215                 220

Asp Asn Ala Ser Thr Ile Ser Ser Lys Tyr Lys Leu Leu Val Asp Glu
225                 230                 235                 240

Ile Ser Asn Lys Ala Tyr Gly Thr Leu Glu Gly Pro Ala Ala Asp Asn
                245                 250                 255

Phe Asp His Phe Arg Asn Ile Trp Lys Ser Ile Val Leu Lys Asp Met
            260                 265                 270

Phe Ile Tyr Cys Asp Leu Leu Leu Gln His Leu Ile Tyr Lys Phe Tyr
        275                 280                 285
```

-continued

```
Tyr Asp Asn Thr Val Asn Asp Ile Lys Lys Asn Phe Asp Glu Ser Trp
    290                 295                 300

Thr Gln Thr Leu Lys Glu
305                 310


<210> SEQ ID NO 20
<211> LENGTH: 367
<212> TYPE: PRT
<213> ORGANISM: Babesia microti

<400> SEQUENCE: 20

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Ser Asp Thr Asp
            20                  25                  30

Pro Glu Ala Gly Gly Pro Ser Glu Ala Gly Gly Pro Ser Gly Thr Val
        35                  40                  45

Gly Pro Ser Glu Ala Gly Gly Pro Ser Glu Ala Gly Gly Pro Ser Gly
    50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Gly Thr Gly Trp Pro Ser Glu Ala Gly Trp Ser Ser Glu
            100                 105                 110

Arg Phe Gly Tyr Gln Leu Leu Pro Tyr Ser Arg Arg Ile Val Ile Phe
        115                 120                 125

Asn Glu Val Cys Leu Ser Tyr Ile Tyr Lys His Ser Val Met Ile Leu
    130                 135                 140

Glu Arg Asp Arg Val Asn Asp Gly His Lys Asp Tyr Ile Glu Glu Lys
145                 150                 155                 160

Thr Lys Glu Lys Asn Lys Leu Lys Lys Glu Leu Glu Lys Cys Phe Pro
                165                 170                 175

Glu Gln Tyr Ser Leu Met Lys Lys Glu Glu Leu Ala Arg Ile Phe Asp
            180                 185                 190

Asn Ala Ser Thr Ile Ser Ser Lys Tyr Lys Leu Leu Val Asp Glu Ile
        195                 200                 205

Ser Asn Lys Ala Tyr Gly Thr Leu Glu Gly Pro Ala Ala Asp Asn Phe
    210                 215                 220

Asp His Phe Arg Asn Ile Trp Lys Ser Ile Val Leu Lys Asp Met Phe
225                 230                 235                 240

Ile Tyr Cys Asp Leu Leu Leu Gln His Leu Ile Tyr Lys Phe Tyr Tyr
                245                 250                 255

Asp Asn Thr Val Asn Asp Ile Lys Lys Asn Phe Asp Glu Ser Lys Ser
            260                 265                 270

Lys Ala Leu Val Leu Arg Asp Lys Ile Thr Lys Lys Asp Gly Asp Tyr
        275                 280                 285

Asn Thr His Phe Glu Asp Met Ile Lys Glu Leu Asn Ser Ala Ala Glu
    290                 295                 300

Glu Phe Asn Lys Ile Val Asp Ile Met Ile Ser Asn Ile Gly Asp Tyr
305                 310                 315                 320

Asp Glu Tyr Asp Ser Ile Ala Ser Phe Lys Pro Phe Leu Ser Met Ile
                325                 330                 335

Thr Glu Ile Thr Lys Ile Thr Lys Val Ser Asn Val Ile Ile Pro Gly
            340                 345                 350
```

-continued

```
Ile Lys Ala Leu Thr Leu Thr Val Phe Leu Ile Phe Ile Thr Lys
        355                 360                 365


<210> SEQ ID NO 21
<211> LENGTH: 492
<212> TYPE: PRT
<213> ORGANISM: Babesia microti

<400> SEQUENCE: 21

Met Tyr Lys Ile Lys Ile Ser Asp Tyr Ile Ile Glu Phe Asp Asp Asn
 1               5                  10                  15

Ala Lys Leu Pro Thr Asp Asn Val Ile Gly Ile Ser Ile Tyr Thr Cys
            20                  25                  30

Glu His Asn Asn Pro Val Leu Ile Glu Phe Tyr Val Ser Lys Lys Gly
        35                  40                  45

Ser Ile Cys Tyr Tyr Phe Tyr Ser Met Asn Asn Asp Thr Asn Lys Trp
    50                  55                  60

Asn Asn His Lys Ile Lys Tyr Asp Lys Arg Phe Asn Glu His Thr Asp
65                  70                  75                  80

Met Asn Gly Ile His Tyr Tyr Tyr Ile Asp Gly Ser Leu Leu Ala Ser
                85                  90                  95

Gly Glu Val Thr Ser Asn Phe Arg Tyr Ile Ser Lys Glu Tyr Glu Tyr
            100                 105                 110

Glu His Thr Glu Leu Ala Lys Glu His Cys Lys Lys Glu Lys Cys Val
        115                 120                 125

Asn Val Asp Asn Ile Glu Asp Asn Asn Leu Lys Ile Tyr Ala Lys Gln
    130                 135                 140

Phe Lys Ser Val Val Thr Thr Pro Ala Asp Val Ala Gly Val Ser Asp
145                 150                 155                 160

Gly Phe Phe Ile Arg Gly Gln Asn Leu Gly Ala Val Gly Ser Val Asn
                165                 170                 175

Glu Gln Pro Asn Thr Val Gly Met Ser Leu Glu Gln Phe Ile Lys Asn
            180                 185                 190

Glu Leu Tyr Ser Phe Ser Asn Glu Ile Tyr His Thr Ile Ser Ser Gln
        195                 200                 205

Ile Ser Asn Ser Phe Leu Ile Met Met Ser Asp Ala Ile Val Lys His
    210                 215                 220

Asp Asn Tyr Ile Leu Lys Lys Glu Gly Glu Gly Cys Glu Gln Ile Tyr
225                 230                 235                 240

Asn Tyr Glu Glu Phe Ile Glu Lys Leu Arg Gly Ala Arg Ser Glu Gly
                245                 250                 255

Asn Asn Met Phe Gln Glu Ala Leu Ile Arg Phe Arg Asn Ala Ser Ser
            260                 265                 270

Glu Glu Met Val Asn Ala Ala Ser Tyr Leu Ser Ala Ala Leu Phe Arg
        275                 280                 285

Tyr Lys Glu Phe Asp Asp Glu Leu Phe Lys Lys Ala Asn Asp Asn Phe
    290                 295                 300

Gly Arg Asp Asp Gly Tyr Asp Phe Asp Tyr Ile Asn Thr Lys Lys Glu
305                 310                 315                 320

Leu Val Ile Leu Ala Ser Val Leu Asp Gly Leu Asp Leu Ile Met Glu
                325                 330                 335

Arg Leu Ile Glu Asn Phe Ser Asp Val Asn Asn Thr Asp Asp Ile Lys
            340                 345                 350

Lys Ala Phe Asp Glu Cys Lys Ser Asn Ala Ile Ile Leu Lys Lys Lys
```

-continued

```
        355                 360                 365

Ile Leu Asp Asn Asp Glu Asp Tyr Lys Ile Asn Phe Arg Glu Met Val
    370                 375                 380

Asn Glu Val Thr Cys Ala Asn Thr Lys Phe Glu Ala Leu Asn Asp Leu
385                 390                 395                 400

Ile Ile Ser Asp Cys Glu Lys Lys Gly Ile Lys Ile Asn Arg Asp Val
                405                 410                 415

Ile Ser Ser Tyr Lys Leu Leu Leu Ser Thr Ile Thr Tyr Ile Val Gly
            420                 425                 430

Ala Gly Val Glu Ala Val Thr Val Ser Val Ser Ala Thr Ser Asn Gly
        435                 440                 445

Thr Glu Ser Gly Gly Ala Gly Ser Gly Thr Gly Thr Ser Val Ser Ala
    450                 455                 460

Thr Ser Thr Leu Thr Gly Asn Gly Gly Thr Glu Ser Gly Gly Thr Ala
465                 470                 475                 480

Gly Thr Thr Thr Ser Ser Gly Thr Trp Phe Gly Lys
                485                 490


<210> SEQ ID NO 22
<211> LENGTH: 138
<212> TYPE: PRT
<213> ORGANISM: Babesia microti

<400> SEQUENCE: 22

Ser Leu Gly Gln Pro Ala Ser Leu Gly Gln Pro Ala Ser Leu Gly Gln
 1               5                  10                  15

Pro Ala Ser Leu Gly Gln Pro Ala Ser Leu Gly Gln Pro Ala Ser Leu
            20                  25                  30

Gly Gln Pro Val Pro Leu Gly Pro Pro Ala Ser Leu Gly Pro Pro Ala
        35                  40                  45

Ser Leu Gly Pro Pro Ala Ser Leu Gly Gln Pro Val Pro Leu Gly Pro
    50                  55                  60

Pro Ala Ser Leu Gly Pro Pro Ala Ser Leu Gly Pro Pro Ala Ser Leu
65                  70                  75                  80

Gly Pro Pro Ala Ser Leu Gly Pro Pro Ala Ser Leu Gly Pro Pro Ala
                85                  90                  95

Ser Leu Gly Pro Pro Ala Ser Leu Gly Pro Pro Ala Ser Leu Gly Pro
            100                 105                 110

Thr Val Pro Leu Gly Pro Pro Ala Ser Arg Ser Val Ser Pro Ala Lys
        115                 120                 125

Thr Ala Pro Leu Ile Lys Lys Ser Val Ile
    130                 135


<210> SEQ ID NO 23
<211> LENGTH: 303
<212> TYPE: PRT
<213> ORGANISM: Babesia microti

<400> SEQUENCE: 23

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
        35                  40                  45

Gly Pro Ser Glu Ala Gly Gly Pro Ser Glu Ala Gly Gly Pro Ser Glu
```

-continued

```
    50                  55                  60

Ala Gly Gly Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Glu Ala Gly Trp Pro Ser Glu Ala Gly Trp Pro Ser Glu
            100                 105                 110

Ala Gly Trp Pro Ser Glu Ala Gly Trp Pro Ser Glu Ala Gly Trp Pro
        115                 120                 125

Ser Glu Arg Phe Gly Tyr Gln Leu Leu Trp Tyr Ser Arg Arg Ile Val
    130                 135                 140

Ile Phe Asn Glu Ile Tyr Leu Ser His Ile Tyr Glu His Ser Val Met
145                 150                 155                 160

Ile Leu Glu Arg Asp Arg Val Asn Asp Gly His Lys Asp Tyr Ile Glu
                165                 170                 175

Glu Lys Thr Lys Glu Lys Asn Lys Leu Lys Lys Glu Leu Glu Lys Cys
            180                 185                 190

Phe Pro Glu Gln Tyr Ser Leu Met Lys Lys Glu Glu Leu Ala Arg Ile
        195                 200                 205

Ile Asp Asn Ala Ser Thr Ile Ser Ser Lys Tyr Lys Leu Leu Val Asp
    210                 215                 220

Glu Ile Ser Asn Lys Ala Tyr Gly Thr Leu Glu Gly Pro Ala Ala Asp
225                 230                 235                 240

Asp Phe Asp His Phe Arg Asn Ile Trp Lys Ser Ile Val Pro Lys Asn
                245                 250                 255

Met Phe Leu Tyr Cys Asp Leu Leu Leu Lys His Leu Ile Arg Lys Phe
            260                 265                 270

Tyr Cys Asp Asn Thr Ile Asn Asp Ile Lys Lys Asn Phe Asp Asp Ile
        275                 280                 285

Glu Lys Leu Gly Cys Phe Gln Ala Arg Ser Phe Leu Pro Val Asn
    290                 295                 300


<210> SEQ ID NO 24
<211> LENGTH: 592
<212> TYPE: PRT
<213> ORGANISM: Babesia microti

<400> SEQUENCE: 24

Met Met Lys Phe Asn Ile Asp Lys Ile Ile Leu Ile Asn Leu Ile Val
 1               5                  10                  15

Leu Leu Asn Arg Asn Val Val Tyr Cys Val Asp Thr Asn Asn Ser Ser
            20                  25                  30

Leu Ile Glu Ser Gln Pro Val Thr Thr Asn Ile Asp Thr Asp Asn Thr
        35                  40                  45

Ile Thr Thr Asn Lys Tyr Thr Gly Thr Ile Ile Asn Ala Asn Ile Val
    50                  55                  60

Glu Tyr Arg Glu Phe Glu Asp Glu Pro Leu Thr Ile Gly Phe Arg Tyr
65                  70                  75                  80

Thr Ile Asp Lys Ser Gln Gln Asn Lys Leu Ser His Pro Asn Lys Ile
                85                  90                  95

Asp Lys Ile Lys Phe Ser Asp Tyr Ile Ile Glu Phe Asp Asp Asn Ala
            100                 105                 110

Lys Leu Pro Thr Asp Asn Val Ile Cys Ile Ser Ile Tyr Thr Cys Lys
        115                 120                 125
```

-continued

```
His Asn Asn Pro Val Leu Ile Arg Phe Ser Cys Ser Ile Glu Lys Tyr
    130                 135                 140

Tyr Tyr His Tyr Phe Tyr Ser Met Asn Asn Asp Thr Asn Lys Trp Asn
145                 150                 155                 160

Asn His Lys Leu Lys Tyr Asp Lys Thr Tyr Asn Glu Tyr Thr Asp Asn
                165                 170                 175

Asn Gly Val Asn Tyr Tyr Lys Ile Tyr Tyr Ser Asp Lys Gln Asn Ser
            180                 185                 190

Pro Thr Asn Gly Asn Glu Tyr Glu Asp Val Ala Leu Ala Arg Ile His
        195                 200                 205

Cys Asn Glu Glu Arg Cys Ala Asn Val Lys Val Asp Lys Ile Lys Tyr
    210                 215                 220

Lys Asn Leu Glu Ile Tyr Val Lys Gln Leu Gly Thr Ile Ile Asn Ala
225                 230                 235                 240

Asn Ile Val Glu Tyr Leu Val Phe Glu Asp Glu Pro Leu Thr Ile Gly
                245                 250                 255

Phe Arg Tyr Thr Ile Asp Lys Ser Gln Gln Asn Glu Leu Ser His Pro
            260                 265                 270

Asn Lys Ile Tyr Lys Ile Lys Phe Ser Asp Tyr Ile Ile Glu Phe Asp
        275                 280                 285

Asp Asp Ala Lys Leu Thr Thr Ile Gly Thr Val Glu Asp Ile Thr Ile
    290                 295                 300

Tyr Thr Cys Lys His Asn Asn Pro Val Leu Ile Arg Phe Ser Cys Ser
305                 310                 315                 320

Ile Glu Lys Tyr Tyr Tyr Tyr Tyr Phe Tyr Ser Met Asn Asn Asn Thr
                325                 330                 335

Asn Lys Trp Asn Asn His Asn Leu Lys Tyr Asp Asn Arg Phe Lys Glu
            340                 345                 350

His Ser Asp Lys Asn Gly Ile Asn Tyr Tyr Glu Ile Ser Ala Phe Lys
        355                 360                 365

Trp Ser Phe Ser Cys Phe Phe Val Asn Lys Tyr Glu His Lys Glu Leu
    370                 375                 380

Ala Arg Ile His Cys Asn Glu Glu Arg Cys Ala Asn Val Lys Val Asp
385                 390                 395                 400

Lys Ile Lys Tyr Lys Asn Leu Glu Ile Tyr Val Lys Gln Leu Gly Thr
                405                 410                 415

Ile Ile Asn Ala Asn Ile Val Glu Tyr Leu Val Phe Glu Asp Glu Pro
            420                 425                 430

Leu Thr Ile Gly Phe Arg Tyr Thr Ile Asp Lys Ser Gln Gln Asn Glu
        435                 440                 445

Leu Ser His Pro Asn Lys Ile Tyr Lys Ile Lys Phe Ser Asp Tyr Ile
    450                 455                 460

Ile Glu Phe Asp Asp Asp Ala Lys Leu Thr Thr Ile Gly Thr Val Glu
465                 470                 475                 480

Asp Ile Thr Ile Tyr Thr Cys Lys His Asn Asn Pro Val Leu Ile Arg
                485                 490                 495

Phe Ser Cys Ser Ile Glu Lys Tyr Tyr Tyr Tyr Tyr Phe Tyr Ser Met
            500                 505                 510

Asn Asn Asn Thr Asn Lys Trp Asn Asn His Asn Leu Lys Tyr Asp Asn
        515                 520                 525

Arg Phe Lys Glu His Ser Asp Lys Asn Gly Ile Asn Tyr Tyr Glu Ile
    530                 535                 540

Ser Ala Phe Lys Trp Ser Phe Ser Cys Phe Phe Val Asn Lys Tyr Glu
```

-continued 545 550 555 560

His Lys Glu Leu Ala Arg Ile His Cys Asn Glu Glu Lys Cys Val Asn
565 570 575

Val Lys Val Asp Asn Ile Gly Asn Lys Asn Leu Glu Ile Tyr Val Lys
580 585 590

<210> SEQ ID NO 25
<211> LENGTH: 463
<212> TYPE: PRT
<213> ORGANISM: Babesia microti

<400> SEQUENCE: 25

Ile Ile Met Lys Ile Asn Ile Asp Asn Ile Ile Leu Ile Asn Leu Ile
1 5 10 15

Ile Leu Leu Asn Arg Asn Val Val Tyr Cys Val Asp Lys Asn Asp Val
20 25 30

Ser Leu Trp Lys Ser Lys Pro Ile Thr Thr Val Ser Thr Thr Asn Asp
35 40 45

Thr Ile Thr Asn Lys Tyr Thr Ser Thr Val Ile Asn Ala Asn Phe Ala
50 55 60

Ser Tyr Arg Glu Phe Glu Asp Arg Glu Pro Leu Thr Ile Gly Phe Glu
65 70 75 80

Tyr Met Ile Asp Lys Ser Gln Gln Asp Lys Leu Ser His Pro Asn Lys
85 90 95

Ile Asp Lys Ile Lys Ile Ser Asp Tyr Ile Ile Glu Phe Asp Asp Asn
100 105 110

Ala Lys Leu Pro Thr Gly Ser Val Asn Asp Ile Ser Ile Ile Thr Cys
115 120 125

Lys His Asn Asn Pro Val Leu Ile Arg Phe Ser Cys Leu Ile Glu Gly
130 135 140

Ser Ile Cys Tyr Tyr Phe Tyr Leu Leu Asn Asn Asp Thr Asn Lys Trp
145 150 155 160

Asn Asn His Lys Leu Lys Tyr Asp Lys Thr Tyr Asn Glu His Thr Asp
165 170 175

Asn Asn Gly Ile Asn Tyr Tyr Lys Ile Asp Tyr Ser Glu Ser Thr Glu
180 185 190

Pro Thr Thr Glu Ser Thr Thr Cys Phe Cys Phe Arg Lys Lys Asn His
195 200 205

Lys Ser Glu Arg Lys Glu Leu Glu Asn Tyr Lys Tyr Glu Gly Thr Glu
210 215 220

Leu Ala Arg Ile His Cys Asn Lys Gly Lys Cys Val Lys Leu Gly Asp
225 230 235 240

Ile Lys Ile Lys Asp Lys Asn Leu Glu Ile Tyr Val Lys Gln Leu Met
245 250 255

Ser Val Asn Thr Pro Val Asn Phe Asp Asn Pro Thr Ser Ile Asn Leu
260 265 270

Pro Thr Val Ser Thr Thr Asn Asp Thr Ile Thr Asn Lys Tyr Thr Gly
275 280 285

Thr Ile Ile Asn Ala Asn Ile Val Glu Tyr Cys Glu Phe Glu Asp Glu
290 295 300

Pro Leu Thr Ile Gly Phe Arg Tyr Thr Ile Asp Lys Ser Gln Gln Asn
305 310 315 320

Lys Leu Ser His Pro Asn Lys Ile Asp Lys Ile Lys Phe Phe Asp Tyr
325 330 335

-continued

```
Ile Ile Glu Phe Asp Asp Asp Val Lys Leu Pro Thr Ile Gly Thr Val
            340                 345                 350

Asn Ile Ile Tyr Ile Tyr Thr Cys Glu His Asn Asn Pro Val Leu Val
        355                 360                 365

Glu Phe Ile Val Ser Ile Glu Glu Ser Tyr Tyr Phe Tyr Phe Tyr Ser
    370                 375                 380

Met Asn Asn Asn Thr Asn Lys Trp Asn Asn His Lys Leu Lys Tyr Asp
385                 390                 395                 400

Lys Arg Phe Lys Lys Tyr Thr Lys Asn Gly Ile Asn Cys Tyr Glu Tyr
                405                 410                 415

Val Leu Arg Lys Cys Ser Ser Tyr Thr Arg Lys Asn Glu Tyr Glu His
            420                 425                 430

Lys Glu Leu Ala Arg Ile His Cys Asn Glu Glu Lys Cys Val Asn Val
        435                 440                 445

Lys Val Asp Asn Ile Glu Lys Lys Asn Leu Glu Ile Tyr Val Lys
    450                 455                 460


<210> SEQ ID NO 26
<211> LENGTH: 297
<212> TYPE: PRT
<213> ORGANISM: Babesia microti

<400> SEQUENCE: 26

Arg Ala Ala Arg Ala Asp Tyr Tyr Lys Tyr Leu Val Asp Glu Tyr Ser
 1               5                  10                  15

Ser Pro Arg Glu Glu Arg Glu Leu Ala Arg Val His Cys Asn Glu Glu
            20                  25                  30

Lys Cys Val Lys Leu Asp Gly Ile Lys Phe Lys Asp Lys Asn Leu Glu
        35                  40                  45

Ile Tyr Val Lys Gln Leu Met Ser Val Asn Thr Pro Val Val Phe Asp
    50                  55                  60

Asn Asn Thr Leu Ile Asn Pro Thr Ser Ser Ser Gly Ala Thr Asp Asp
65                  70                  75                  80

Ile Thr Tyr Glu Leu Ser Val Glu Ser Gln Pro Val Pro Thr Asn Ile
                85                  90                  95

Asp Thr Gly Asn Asn Ile Thr Thr Asn Thr Ser Asn Asn Asn Leu Ile
            100                 105                 110

Lys Ala Lys Phe Leu Tyr Asn Phe Asn Leu Pro Gly Lys Pro Ser Thr
        115                 120                 125

Gly Leu Phe Glu Tyr Thr Ile Asp Lys Ser Glu Gln Asn Lys Leu Ser
    130                 135                 140

His Pro Asn Lys Ile Asp Lys Ile Lys Phe Ser Asp Tyr Ile Ile Glu
145                 150                 155                 160

Phe Asp Asp Asp Ala Lys Leu Pro Thr Ile Gly Thr Val Asn Ile Ile
                165                 170                 175

Ser Ile Ile Thr Cys Lys His Asn Asn Pro Val Leu Val Glu Phe Ile
            180                 185                 190

Val Ser Thr Glu Ile Tyr Cys Tyr Tyr Asn Tyr Phe Tyr Ser Met Asn
        195                 200                 205

Asn Asn Thr Asn Lys Trp Asn Asn His Lys Leu Lys Tyr Asp Lys Arg
    210                 215                 220

Tyr Lys Glu Glu Tyr Thr Asp Asp Asn Gly Ile Asn Tyr Tyr Lys Leu
225                 230                 235                 240

Asn Asp Ser Glu Pro Thr Glu Ser Thr Glu Ser Thr Thr Cys Phe Cys
                245                 250                 255
```

-continued

```
Phe Arg Lys Lys Asn His Lys Tyr Glu Asn Glu Arg Thr Ala Leu Ala
            260                 265                 270

Lys Glu His Cys Asn Glu Glu Arg Cys Val Lys Val Asp Asn Ile Lys
        275                 280                 285

Asp Asn Asn Leu Glu Ile Tyr Leu Lys
    290                 295


<210> SEQ ID NO 27
<211> LENGTH: 121
<212> TYPE: PRT
<213> ORGANISM: Babesia microti

<400> SEQUENCE: 27

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Ser Asp Thr Asp
            20                  25                  30

Pro Glu Ala Gly Gly Pro Ser Glu Ala Gly Gly Pro Ser Glu Ala Gly
        35                  40                  45

Gly Pro Ser Gly Thr Val Gly Pro Ser Glu Ala Gly Gly Pro Ser Glu
    50                  55                  60

Ala Gly Gly Pro Ser Gly Thr Gly Trp Pro Ser Glu Ala Gly Gly Pro
65                  70                  75                  80

Ser Glu Ala Gly Gly Pro Ser Gly Thr Gly Trp Pro Ser Glu Ala Gly
                85                  90                  95

Trp Ser Ser Glu Arg Phe Gly Tyr Gln Leu Leu Pro Tyr Ser Arg Arg
            100                 105                 110

Ile Val Thr Phe Asn Glu Val Cys Leu
        115                 120


<210> SEQ ID NO 28
<211> LENGTH: 267
<212> TYPE: PRT
<213> ORGANISM: Babesia microti

<400> SEQUENCE: 28

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Ser Asp Thr Asp
            20                  25                  30

Pro Glu Ala Gly Gly Pro Ser Gly Thr Val Gly Pro Ser Glu Ala Gly
        35                  40                  45

Gly Pro Ser Glu Ala Gly Gly Pro Ser Gly Thr Gly Trp Pro Ser Glu
    50                  55                  60

Ala Gly Gly Pro Ser Glu Ala Gly Gly Pro Ser Gly Thr Gly Trp Pro
65                  70                  75                  80

Ser Glu Ala Gly Trp Ser Ser Glu Arg Phe Gly Tyr Gln Leu Leu Pro
                85                  90                  95

Tyr Ser Arg Arg Ile Val Thr Phe Asn Glu Val Cys Leu Ser Tyr Ile
            100                 105                 110

Tyr Lys His Ser Val Met Ile Leu Glu Arg Asp Arg Val Asn Asp Gly
        115                 120                 125

His Lys Asp Tyr Ile Glu Glu Lys Thr Lys Glu Lys Asn Lys Leu Lys
    130                 135                 140

Lys Glu Leu Glu Lys Cys Phe Pro Glu Gln Tyr Ser Leu Met Lys Lys
145                 150                 155                 160
```

-continued

Glu Glu Leu Ala Arg Ile Phe Asp Asn Ala Ser Thr Ile Ser Ser Lys
165 170 175

Tyr Lys Leu Leu Val Asp Glu Ile Ser Asn Lys Ala Tyr Gly Thr Leu
180 185 190

Glu Gly Pro Ala Ala Asp Asn Phe Asp His Phe Arg Asn Ile Trp Lys
195 200 205

Ser Ile Val Leu Lys Asp Met Phe Ile Tyr Cys Asp Leu Leu Leu Gln
210 215 220

His Leu Ile Tyr Lys Phe Tyr Tyr Asp Asn Thr Ile Asn Asp Ile Lys
225 230 235 240

Lys Asn Phe Asp Glu Ser Lys Ser Lys Ala Leu Val Leu Arg Asp Lys
245 250 255

Ile Thr Lys Lys Asp Val Tyr Val Asn Asp His
260 265

<210> SEQ ID NO 29
<211> LENGTH: 16
<212> TYPE: PRT
<213> ORGANISM: Babesia microti

<400> SEQUENCE: 29

Ala Trp Thr Phe Ser Val Leu Glu Leu Gln Glu Phe Ser Tyr Thr Val
1 5 10 15

<210> SEQ ID NO 30
<211> LENGTH: 465
<212> TYPE: PRT
<213> ORGANISM: Babesia microti

<400> SEQUENCE: 30

Met Leu Thr Phe Gly Asn Ile Arg Phe His Asn Ile Asn Leu Pro Pro
1 5 10 15

Phe Ser Leu Gly Ile Ile His Ser Ile Thr Val Glu Lys Ala Ile Asn
20 25 30

Ser Glu Asp Phe Asp Gly Ile Gln Thr Leu Leu Gln Val Ser Ile Ile
35 40 45

Ala Ser Tyr Gly Pro Ser Gly Asp Tyr Ser Ser Phe Val Phe Thr Pro
50 55 60

Val Val Thr Ala Asp Thr Asn Val Phe Tyr Lys Leu Glu Thr Asp Phe
65 70 75 80

Lys Leu Asp Val Asp Val Ile Thr Lys Thr Ser Leu Glu Leu Pro Thr
85 90 95

Ser Val Pro Gly Phe His Tyr Thr Glu Thr Ile Tyr Gln Gly Thr Glu
100 105 110

Leu Ser Lys Phe Ser Lys Pro Gln Cys Lys Leu Asn Asp Pro Pro Ile
115 120 125

Thr Thr Gly Ser Gly Leu Gln Ile Ile His Asp Gly Leu Asn Asn Ser
130 135 140

Thr Ile Ile Thr Asn Lys Glu Val Asn Val Asp Gly Thr Asp Leu Val
145 150 155 160

Phe Phe Glu Leu Leu Pro Pro Ser Asp Gly Ile Pro Thr Leu Arg Ser
165 170 175

Lys Leu Phe Pro Val Leu Lys Ser Ile Pro Met Ile Ser Thr Gly Val
180 185 190

Asn Glu Leu Leu Leu Glu Val Leu Glu Asn Pro Ser Phe Pro Ser Ala
195 200 205

-continued

```
Ile Ser Asn Tyr Thr Gly Leu Thr Gly Arg Leu Asn Lys Leu Leu Thr
    210                 215                 220

Val Leu Asp Gly Ile Val Asp Ser Ala Ile Ser Val Lys Thr Thr Glu
225                 230                 235                 240

Thr Val Pro Asp Asp Ala Glu Thr Ser Ile Ser Ser Leu Lys Ser Leu
                245                 250                 255

Ile Lys Ala Ile Arg Asp Asn Ile Thr Thr Thr Arg Asn Glu Val Thr
            260                 265                 270

Lys Asp Asp Val Tyr Ala Leu Lys Lys Ala Leu Thr Cys Leu Thr Thr
        275                 280                 285

His Leu Ile Tyr His Ser Lys Val Asp Gly Ile Ser Phe Asp Met Leu
    290                 295                 300

Gly Thr Gln Lys Asn Lys Ser Ser Pro Leu Gly Lys Ile Gly Thr Ser
305                 310                 315                 320

Met Asp Asp Ile Ile Ala Met Phe Ser Asn Pro Asn Met Tyr Leu Val
                325                 330                 335

Lys Val Ala Tyr Leu Gln Ala Ile Glu His Ile Phe Leu Ile Ser Thr
            340                 345                 350

Lys Tyr Asn Asp Ile Phe Asp Tyr Thr Ile Asp Phe Ser Lys Arg Glu
        355                 360                 365

Ala Thr Asp Ser Gly Ser Phe Thr Asp Ile Leu Leu Gly Asn Lys Val
    370                 375                 380

Lys Glu Ser Leu Ser Phe Ile Glu Gly Leu Ile Ser Asp Ile Lys Ser
385                 390                 395                 400

His Ser Leu Lys Ala Gly Val Thr Gly Gly Ile Ser Ser Ser Ser Leu
                405                 410                 415

Phe Asp Glu Ile Phe Asp Glu Leu Asn Leu Asp Gln Ala Thr Ile Arg
            420                 425                 430

Thr Leu Val Ala Pro Leu Asp Trp Pro Leu Ile Ser Asp Lys Ser Leu
        435                 440                 445

His Pro Ser Leu Lys Met Val Val Val Leu Pro Gly Phe Phe Ile Val
    450                 455                 460

Pro
465


<210> SEQ ID NO 31
<211> LENGTH: 128
<212> TYPE: PRT
<213> ORGANISM: Babesia microti

<400> SEQUENCE: 31

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Ser Asp Thr Asp
            20                  25                  30

Pro Glu Ala Gly Gly Pro Ser Glu Ala Gly Gly Pro Ser Gly Thr Val
        35                  40                  45

Gly Pro Ser Glu Ala Gly Gly Pro Ser Glu Ala Gly Gly Pro Ser Gly
    50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
               85                  90                  95

Trp Pro Ser Gly Thr Gly Trp Pro Ser Glu Ala Gly Trp Ser Ser Glu
```

-continued

```
            100                 105                 110

Arg Phe Gly Tyr Gln Leu Leu Pro Tyr Ser Arg Arg Ile Val Ile Phe
        115                 120                 125
```

<210> SEQ ID NO 32
<211> LENGTH: 245
<212> TYPE: PRT
<213> ORGANISM: Babesia microti

<400> SEQUENCE: 32

```
Gln Glu Cys Cys Leu Val Val Lys Asp Lys Val Ile Arg His Ala Ala
 1               5                  10                  15

Phe Ala Ala Thr Ile Ile Ile Arg Arg Arg Arg Val Ser Phe Ile Ile
            20                  25                  30

Leu Gly Leu Ile Ile Ala Thr Met Thr Pro Phe Phe Thr Lys Val Phe
        35                  40                  45

Phe Phe Gln Arg Cys Leu Ser Ile Met Arg Phe Tyr Ser Ser Leu Pro
    50                  55                  60

Thr Phe Ile Leu Ile Glu Ile Ala Met Leu Phe Phe Met Ser Val Thr
65                  70                  75                  80

Cys Phe Leu Arg Cys Leu Ser Ile Ile Arg Phe Tyr Ser Ser Ile Ser
                85                  90                  95

Thr Phe Ile Leu Ile Asp Phe Val Met Pro Phe Phe Thr Leu Phe Thr
            100                 105                 110

Tyr Phe Leu Arg Cys Leu Ser Ile Met Arg Phe Ser Phe Ser Leu Leu
        115                 120                 125

Thr Phe Ile Arg Ile Asp Phe Val Met Pro Phe Phe Met Ser Val Thr
    130                 135                 140

Cys Phe Leu Arg Cys Leu Ser Ile Ile Arg Phe Tyr Ser Ser Ile Ser
145                 150                 155                 160

Thr Phe Ile Leu Ile Asp Phe Val Met Pro Phe Phe Thr Leu Phe Thr
                165                 170                 175

Tyr Phe Leu Arg Cys Leu Ser Ile Ile Arg Phe Tyr Ser Ser Ile Ser
            180                 185                 190

Thr Phe Ile Leu Ile Asp Phe Val Met Pro Phe Phe Thr Leu Phe Thr
        195                 200                 205

Tyr Phe Leu Arg Cys Leu Ser Ile Met Arg Phe Ser Phe Ser Leu Leu
    210                 215                 220

Thr Phe Ile Arg Ile Gly Phe Ala Met Pro Phe Phe Thr Leu Phe Ile
225                 230                 235                 240

Tyr Phe Leu Cys Arg
                245
```

<210> SEQ ID NO 33
<211> LENGTH: 293
<212> TYPE: PRT
<213> ORGANISM: Babesia microti

<400> SEQUENCE: 33

```
Thr Ala Phe Ala Ala Phe Leu Ala Phe Gly Asn Ile Ser Pro Val Leu
 1               5                  10                  15

Ser Ala Gly Gly Ser Gly Gly Asn Gly Gly Asn Gly Gly Gly His Gln
            20                  25                  30

Glu Gln Asn Asn Ala Asn Asp Ser Ser Asn Pro Thr Gly Ala Gly Gly
        35                  40                  45

Gln Pro Asn Asn Glu Ser Lys Lys Lys Ala Val Lys Leu Asp Leu Asp
```

-continued

```
    50                  55                  60

Leu Met Lys Glu Thr Lys Asn Val Cys Thr Thr Val Asn Thr Lys Leu
65                  70                  75                  80

Val Gly Lys Ala Lys Ser Lys Leu Asn Lys Leu Glu Gly Glu Ser His
                85                  90                  95

Lys Glu Tyr Val Ala Glu Lys Thr Lys Glu Ile Asp Glu Lys Asn Lys
            100                 105                 110

Lys Phe Asn Glu Asn Leu Val Lys Ile Glu Lys Lys Lys Lys Ile Lys
        115                 120                 125

Val Pro Ala Asp Thr Gly Ala Glu Val Asp Ala Val Asp Asp Gly Val
    130                 135                 140

Ala Gly Ala Leu Ser Asp Leu Ser Ser Asp Ile Ser Ala Ile Lys Thr
145                 150                 155                 160

Leu Thr Asp Asp Val Ser Glu Lys Val Ser Glu Asn Leu Lys Asp Asp
                165                 170                 175

Glu Ala Ser Ala Thr Glu His Thr Asp Ile Lys Glu Lys Ala Thr Leu
            180                 185                 190

Leu Gln Glu Ser Cys Asn Gly Ile Gly Thr Ile Leu Asp Lys Leu Ala
        195                 200                 205

Glu Tyr Leu Asn Asn Asp Thr Thr Gln Asn Ile Lys Lys Glu Phe Asp
    210                 215                 220

Glu Arg Lys Lys Asn Leu Thr Ser Leu Lys Thr Lys Val Glu Asn Lys
225                 230                 235                 240

Asp Glu Asp Tyr Val Asp Val Thr Met Thr Ser Lys Thr Asp Leu Ile
                245                 250                 255

Ile His Cys Leu Thr Cys Thr Asn Asp Ala His Gly Leu Phe Asp Phe
            260                 265                 270

Glu Ser Lys Ser Leu Ile Lys Gln Thr Phe Lys Leu Arg Ser Lys Asp
        275                 280                 285

Glu Gly Glu Leu Cys
    290


<210> SEQ ID NO 34
<211> LENGTH: 431
<212> TYPE: PRT
<213> ORGANISM: Babesia microti

<400> SEQUENCE: 34

Gly Pro Lys Met Lys Val Asn Ser Ala Asn Leu Asp Phe Arg Trp Ala
 1               5                  10                  15

Met Tyr Met Leu Asn Ser Lys Ile His Leu Ile Glu Ser Ser Leu Ile
            20                  25                  30

Asp Asn Phe Thr Leu Asp Asn Pro Ser Ala Tyr Glu Ile Leu Arg Val
        35                  40                  45

Ser Tyr Asn Ser Asn Glu Phe Gln Val Gln Ser Pro Gln Asn Ile Asn
    50                  55                  60

Asn Glu Met Glu Ser Ser Thr Pro Glu Ser Asn Ile Ile Trp Val Val
65                  70                  75                  80

His Ser Asp Val Ile Met Lys Arg Phe Asn Cys Lys Asn Arg Lys Ser
                85                  90                  95

Leu Ser Thr His Ser Leu Thr Glu Asn Asp Ile Leu Lys Phe Gly Arg
            100                 105                 110

Ile Glu Leu Ser Val Lys Cys Ile Ile Met Gly Ala Gly Ile Thr Ala
        115                 120                 125
```

-continued

```
Ser Asp Leu Asn Leu Lys Gly Leu Gly Phe Ile Ser Pro Asp Lys Gln
    130                 135                 140

Ser Thr Asn Val Cys Asn Tyr Phe Glu Asp Met His Glu Ser Tyr His
145                 150                 155                 160

Ile Leu Asp Thr Gln Arg Ala Ser Asp Cys Val Ser Asp Asp Gly Ala
                165                 170                 175

Asp Ile Asp Ile Ser Asn Phe Asp Met Val Gln Asp Gly Asn Ile Asn
            180                 185                 190

Ser Val Asp Ala Asp Ser Glu Thr Cys Met Ala Asn Ser Gly Val Thr
        195                 200                 205

Val Asn Asn Thr Glu Asn Val Ser Asn Ser Glu Asn Phe Gly Lys Leu
    210                 215                 220

Lys Ser Leu Val Ser Thr Thr Thr Pro Leu Cys Arg Ile Cys Leu Cys
225                 230                 235                 240

Gly Glu Ser Asp Pro Gly Pro Leu Val Thr Pro Cys Asn Cys Lys Gly
                245                 250                 255

Ser Leu Asn Tyr Val His Leu Glu Cys Leu Arg Thr Trp Ile Lys Gly
            260                 265                 270

Arg Leu Ser Ile Val Lys Asp Asp Asp Ala Ser Phe Phe Trp Lys Glu
        275                 280                 285

Leu Ser Cys Glu Leu Cys Gly Lys Pro Tyr Pro Ser Val Leu Gln Val
    290                 295                 300

Asp Asp Thr Glu Thr Asn Leu Met Asp Ile Lys Lys Pro Asp Ala Pro
305                 310                 315                 320

Tyr Val Val Leu Glu Met Arg Ser Asn Ser Gly Asp Gly Cys Phe Val
                325                 330                 335

Val Ser Val Ala Lys Asn Lys Ala Ile Ile Gly Arg Gly His Glu Ser
            340                 345                 350

Asp Val Arg Leu Ser Asp Ile Ser Val Ser Arg Met His Ala Ser Leu
        355                 360                 365

Glu Leu Asp Gly Gly Lys Val Val Ile His Asp Gln Gln Ser Lys Phe
    370                 375                 380

Gly Thr Leu Val Arg Ala Lys Ala Pro Phe Ser Met Pro Ile Lys Gly
385                 390                 395                 400

Pro Ile Cys Leu Gln Val Ser Ile Phe Phe Leu Asn Leu Lys Ile Ser
                405                 410                 415

Thr His Ser Leu Thr Met Glu Arg Gly Met Glu His Val Leu Leu
            420                 425                 430
```

<210> SEQ ID NO 35
<211> LENGTH: 6
<212> TYPE: PRT
<213> ORGANISM: Babesia microti
<220> FEATURE:
<221> NAME/KEY: VARIANT
<222> LOCATION: (1)...(1)
<223> OTHER INFORMATION: Xaa = Glutamic Acid or Glycine
<221> NAME/KEY: VARIANT
<222> LOCATION: (2)...(2)
<223> OTHER INFORMATION: Xaa = Alanine or Threonine
<221> NAME/KEY: VARIANT
<222> LOCATION: (3)...(3)
<223> OTHER INFORMATION: Xaa = Glycine or Valine
<221> NAME/KEY: VARIANT
<222> LOCATION: (4)...(4)
<223> OTHER INFORMATION: Xaa = Tryptophan or Glycine
<221> NAME/KEY: VARIANT
<222> LOCATION: (5)...(5)
<223> OTHER INFORMATION: Xaa = Proline or Serine -continued

<400> SEQUENCE: 35

Xaa Xaa Xaa Xaa Xaa Ser
 1               5

<210> SEQ ID NO 36
<211> LENGTH: 32
<212> TYPE: PRT
<213> ORGANISM: Babesia microti
<220> FEATURE:
<221> NAME/KEY: VARIANT
<222> LOCATION: (6)...(6)
<223> OTHER INFORMATION: Xaa = Methionine or Isoleucine
<221> NAME/KEY: VARIANT
<222> LOCATION: (9)...(9)
<223> OTHER INFORMATION: Xaa = Tyrosine or Serine
<221> NAME/KEY: VARIANT
<222> LOCATION: (10)...(10)
<223> OTHER INFORMATION: Xaa = Serine or Phenylalanine
<221> NAME/KEY: VARIANT
<222> LOCATION: (12)...(12)
<223> OTHER INFORMATION: Xaa = Leucine or Isoleucine
<221> NAME/KEY: VARIANT
<222> LOCATION: (13)...(13)
<223> OTHER INFORMATION: Xaa = Proline, Serine or Leucine
<221> NAME/KEY: VARIANT
<222> LOCATION: (17)...(17)
<223> OTHER INFORMATION: Xaa = Leucine or Arginine
<221> NAME/KEY: VARIANT
<222> LOCATION: (19)...(19)
<223> OTHER INFORMATION: Xaa = Glutamic Acid, Aspartic Acid or Glycine
<221> NAME/KEY: VARIANT
<222> LOCATION: (20)...(20)
<223> OTHER INFORMATION: Xaa = Isoleucine or Phenylalanine
<221> NAME/KEY: VARIANT
<222> LOCATION: (21)...(21)
<223> OTHER INFORMATION: Xaa = Alanine or Valine
<221> NAME/KEY: VARIANT
<222> LOCATION: (23)...(23)
<223> OTHER INFORMATION: Xaa = Leucine or Proline
<221> NAME/KEY: VARIANT
<222> LOCATION: (26)...(26)
<223> OTHER INFORMATION: Xaa = Methionine or Threonine
<221> NAME/KEY: VARIANT
<222> LOCATION: (27)...(27)
<223> OTHER INFORMATION: Xaa = Serine or Leucine
<221> NAME/KEY: VARIANT
<222> LOCATION: (28)...(28)
<223> OTHER INFORMATION: Xaa = Valine or Phenylalanine
<221> NAME/KEY: VARIANT
<222> LOCATION: (29)...(29)
<223> OTHER INFORMATION: Xaa = Threonine or Isoleucine
<221> NAME/KEY: VARIANT
<222> LOCATION: (30)...(30)
<223> OTHER INFORMATION: Xaa = Cysteine ro Tyrosine

<400> SEQUENCE: 36

Arg Cys Leu Ser Ile Xaa Arg Phe Xaa Xaa Ser Xaa Xaa Thr Phe Ile
 1               5                  10                  15

Xaa Ile Xaa Xaa Xaa Met Xaa Phe Phe Xaa Xaa Xaa Xaa Xaa Phe Leu
            20                  25                  30

<210> SEQ ID NO 37
<211> LENGTH: 1820
<212> TYPE: DNA
<213> ORGANISM: Babesia microti

<400> SEQUENCE: 37
cggcacgagt agcccccacc atcttttgca ttcatttcaa gtttctccaa atctcgatgg 60
gacctccaat tttggctcca ccacaaacaa gtctgacata ttgagcaaaa catattgatt 120
taatttaaag aacagacatc tggccattca tgctaagagg tctcttcatt gttgagtggg 180

-continued

```
aacagccttg tatacgggct tacaacacaa tggaaaaaca ccttgtagaa gagatcatgc    240

ttcactcagt gctagatgtt gatgccagtg atttgcttgg ggtagtaagc cagtactaga    300

atacaggatg cacttggact ggcaaacaga atacacctgt tgcctgaata gaaactcaca    360

gagacccgat gctgtctggt accaacaagg ttctgcttct gggaagaatt tacagatatt    420

atgttgggaa aagagacacc ctgtatgtgt agaaacaaag aagcacagat cttagatgaa    480

ttaatataag aatgatactt ctctagaaac aaatgtagtt accaactata ttccagaacc    540

caatgcggat tcagaatctg tacatgttga aatccaggaa catgataaca tcaatccaca    600

agacgcttgc gatagtgagc cgctcgaaca aatggattct gataccaggg tgttgcccga    660

aagtttggat gagggggtac cacaccaatt ctctagatta gggcaccact cagacatggc    720

atctgatata aatgatgaag aaccatcatt taaaatcggc gagaatgaca taattcaacc    780

accctgggaa gatacagctc cataccattc aatagatgat gaagagcttg acaacttaat    840

gagactaacg gcgcaagaaa caagtgacga tcatgaagaa gggaatggca aactcaatac    900

gaataaaagt gagaagactg aaagaaaatc gcatgatact cagacaccgc aagaaatata    960

tgaagagctt gacaacttac tgagactaac ggcacaagaa atatatgaag agcgtaaaga   1020

agggcatggc aaacccaata cgaataaaag tgagaaggct gaaagaaaat cgcatgatac   1080

tcagacaacg caagaaatat gtgaagagtg tgaagaaggg catgacaaaa tcaataagaa   1140

taaaagtgga aatgctggaa taaaatcgta tgatactcag acaacgcaag aaatatgtga   1200

agagtgtgaa gaagggcatg acaaaatcaa taagaataaa agtggaaatg ctggaataaa   1260

atcgtatgat actcagacac cgcaggaaac aagtgacgct catgaagaag ggcatgacaa   1320

aatcaatacg aataaaagtg agaaggctga aagaaaatcg catgatactc agacaacgca   1380

agaaatatgt gaagagtgtg aagaagggca tgacaaaatc aataagaata aaagtggaaa   1440

tgctggaata aaatcgtatg atactcagac accgcaggaa acaagtgacg ctcatgaaga   1500

agagcatggc aatctcaata agaataaaag tgggaaggct ggaataaaat cgcataatac   1560

tcagacaccg ctgaaaaaaa aagacttttg taaagaaggg tgtcatggtt gcaataataa   1620

gcccgaggat aatgaaagag acccgtcgtc gcctgatgat gatggtggct gcgaatgcgg   1680

catgacgaat cactttgtct ttgactacaa gacaacactc ttgttaaaga gcctcaagac   1740

tgaaacatcc actcattatt acattgccat ggctgcaatt tttactattt cattattccc   1800

atgcatgttt aaggctttcc                                               1820
```

<210> SEQ ID NO 38
<211> LENGTH: 445
<212> TYPE: PRT
<213> ORGANISM: Babesia microti

<400> SEQUENCE: 38

```
Tyr Lys Asn Asp Thr Ser Leu Glu Thr Asn Val Val Thr Asn Tyr Ile
 1               5                  10                  15

Pro Glu Pro Asn Ala Asp Ser Glu Ser Val His Val Glu Ile Gln Glu
            20                  25                  30

His Asp Asn Ile Asn Pro Gln Asp Ala Cys Asp Ser Glu Pro Leu Glu
        35                  40                  45

Gln Met Asp Ser Asp Thr Arg Val Leu Pro Glu Ser Leu Asp Glu Gly
    50                  55                  60

Val Pro His Gln Phe Ser Arg Leu Gly His His Ser Asp Met Ala Ser
65                  70                  75                  80
```

-continued

```
Asp Ile Asn Asp Glu Glu Pro Ser Phe Lys Ile Gly Glu Asn Asp Ile
                85                  90                  95

Ile Gln Pro Pro Trp Glu Asp Thr Ala Pro Tyr His Ser Ile Asp Asp
            100                 105                 110

Glu Glu Leu Asp Asn Leu Met Arg Leu Thr Ala Gln Glu Thr Ser Asp
        115                 120                 125

Asp His Glu Glu Gly Asn Gly Lys Leu Asn Thr Asn Lys Ser Glu Lys
    130                 135                 140

Thr Glu Arg Lys Ser His Asp Thr Gln Thr Pro Gln Glu Ile Tyr Glu
145                 150                 155                 160

Glu Leu Asp Asn Leu Leu Arg Leu Thr Ala Gln Glu Ile Tyr Glu Glu
                165                 170                 175

Arg Lys Glu Gly His Gly Lys Pro Asn Thr Asn Lys Ser Glu Lys Ala
            180                 185                 190

Glu Arg Lys Ser His Asp Thr Gln Thr Thr Gln Glu Ile Cys Glu Glu
        195                 200                 205

Cys Glu Glu Gly His Asp Lys Ile Asn Lys Asn Lys Ser Gly Asn Ala
    210                 215                 220

Gly Ile Lys Ser Tyr Asp Thr Gln Thr Thr Gln Glu Ile Cys Glu Glu
225                 230                 235                 240

Cys Glu Glu Gly His Asp Lys Ile Asn Lys Asn Lys Ser Gly Asn Ala
                245                 250                 255

Gly Ile Lys Ser Tyr Asp Thr Gln Thr Pro Gln Glu Thr Ser Asp Ala
            260                 265                 270

His Glu Glu Gly His Asp Lys Ile Asn Thr Asn Lys Ser Glu Lys Ala
        275                 280                 285

Glu Arg Lys Ser His Asp Thr Gln Thr Thr Gln Glu Ile Cys Glu Glu
    290                 295                 300

Cys Glu Glu Gly His Asp Lys Ile Asn Lys Asn Lys Ser Gly Asn Ala
305                 310                 315                 320

Gly Ile Lys Ser Tyr Asp Thr Gln Thr Pro Gln Glu Thr Ser Asp Ala
                325                 330                 335

His Glu Glu Glu His Gly Asn Leu Asn Lys Asn Lys Ser Gly Lys Ala
            340                 345                 350

Gly Ile Lys Ser His Asn Thr Gln Thr Pro Leu Lys Lys Lys Asp Phe
        355                 360                 365

Cys Lys Glu Gly Cys His Gly Cys Asn Asn Lys Pro Glu Asp Asn Glu
    370                 375                 380

Arg Asp Pro Ser Ser Pro Asp Asp Asp Gly Gly Cys Glu Cys Gly Met
385                 390                 395                 400

Thr Asn His Phe Val Phe Asp Tyr Lys Thr Thr Leu Leu Leu Lys Ser
                405                 410                 415

Leu Lys Thr Glu Thr Ser Thr His Tyr Tyr Ile Ala Met Ala Ala Ile
            420                 425                 430

Phe Thr Ile Ser Leu Phe Pro Cys Met Phe Lys Ala Phe
        435                 440                 445
```

<210> SEQ ID NO 39
<211> LENGTH: 32
<212> TYPE: PRT
<213> ORGANISM: Babesia microti
<220> FEATURE:
<221> NAME/KEY: VARIANT
<222> LOCATION: (3)...(3)
<223> OTHER INFORMATION: Xaa = Glycine or Aspartic Acid
<221> NAME/KEY: VARIANT -continued
<222> LOCATION: (5)...(5)
<223> OTHER INFORMATION: Xaa = Proline or Isoleucine
<221> NAME/KEY: VARIANT
<222> LOCATION: (7)...(7)
<223> OTHER INFORMATION: Xaa = Lysine or Threonine
<221> NAME/KEY: VARIANT
<222> LOCATION: (11)...(11)
<223> OTHER INFORMATION: Xaa = Glutamic Acid or Glycine
<221> NAME/KEY: VARIANT
<222> LOCATION: (12)...(12)
<223> OTHER INFORMATION: Xaa = Lysine or Asparagine
<221> NAME/KEY: VARIANT
<222> LOCATION: (14)...(14)
<223> OTHER INFORMATION: Xaa = Glutamic Acid or Glycine
<221> NAME/KEY: VARIANT
<222> LOCATION: (15)...(15)
<223> OTHER INFORMATION: Xaa = Isoleucine or Arginine
<221> NAME/KEY: VARIANT
<222> LOCATION: (18)...(18)
<223> OTHER INFORMATION: Xaa = Histidine or Tyrosine
<221> NAME/KEY: VARIANT
<222> LOCATION: (23)...(23)
<223> OTHER INFORMATION: Xaa = Threonine or Proline
<221> NAME/KEY: VARIANT
<222> LOCATION: (26)...(26)
<223> OTHER INFORMATION: Xaa = Isoleucine or Threonine
<221> NAME/KEY: VARIANT
<222> LOCATION: (27)...(27)
<223> OTHER INFORMATION: Xaa = Cysteine or Serine
<221> NAME/KEY: VARIANT
<222> LOCATION: (28)...(28)
<223> OTHER INFORMATION: Xaa = Aspartic Acid or Glutamic Acid
<221> NAME/KEY: VARIANT
<222> LOCATION: (29)...(29)
<223> OTHER INFORMATION: Xaa = Glutamic Acid or Alanine
<221> NAME/KEY: VARIANT
<222> LOCATION: (30)...(30)
<223> OTHER INFORMATION: Xaa = Cysteine or Histidine

<400> SEQUENCE: 39

```
Gly His Xaa Lys Xaa Asn Xaa Asn Lys Ser Xaa Xaa Ala Xaa Xaa Lys
 1               5                  10                  15

Ser Xaa Asp Thr Gln Thr Xaa Gln Glu Xaa Xaa Xaa Xaa Xaa Glu Glu
            20                  25                  30
```

<210> SEQ ID NO 40
<211> LENGTH: 2430
<212> TYPE: DNA
<213> ORGANISM: Babesia microti

<400> SEQUENCE: 40

```
tgtattgtgt agataaaaat gatgtttcat tatggaaatc aaaacctata acaactgtca     60

gtaccactaa tgatactatt acaaatacac acactactaa tgtaattaat gccaatctta    120

ttggccactt taattataag gatagggaac ctttaacaat agtatttgta tacatgatcg    180

atgaatcaga acaaaataaa ttatcacatc cgaataaaat tgataaaatc aaaatttctg    240

attatataat tgaatttgat gacaatgcta aattaccaac tggtagtgtt attgatttaa    300

acatctatac ttgcaaacat aataatccag tattaattga attttatgtt tctatagaag    360

gatctttctg ctattatttc tctcattgaa taatgataca aatgaatgga ataatcacaa    420

aataaaatat gataaaaaat ataaagaata tacggacatg aatggtattc attattatta    480

tattgatggt agtttacttg taagtggcga agttacatct aattttcgtt atatttctaa    540

agaatatgaa tatgagcata caggattagt aaaaaaatat tgtaatgaag aaagatgtgt    600

aaaattggat aacattaaga taaaggataa taatttggaa atttatgtga aataatttaa    660

tgaagtataa tattatttat aataattcaa agattaatat aatcaattat tataattaca    720
```

-continued

```
aaaataatta attgtagaat attatattat taatcaattc agattataaa tacatatttt    780

tacatacatt tcaatttaaa cattcaaatt aatgtcattt ttatctacat tattataatt    840

ataactataa tattcattaa atactattaa aaaaaatatc ctctacatta tattaattat    900

tatagtatgt cattatataa catattcaca acgtataaca aatcaatcat taacatatac    960

atatatgata tcattaataa tcaatattta attgatacaa taatcaatag tcatctgtaa   1020

tataatcatt gtatactaat ttattataaa ttattacaaa atacactctt ttacttcatt   1080

ttatttctgt taaatttcat attctaatat tatattcatc tttctcatgt tactttaatc   1140

tatttccata tttatcccaa tttcttcatt taagactgag atgttcgttc gttcatacat   1200

aaataatgtg taaattttgt aatatataat aatgtataca tctggtatta catctatttt   1260

gtaataaata ttaaaaaaac ggttaaagtt agtgccttaa ttccaggaat tattacatta   1320

gaaactttgg tgattttagt gatttcggtg atcattgaaa gaaatggttt gaaacttgca   1380

atactgtcat actcatcata atccccaatg ttggaaatca tgatgtcaac aattttatta   1440

aattcttctg ctgcactatt caactcctta atcatgtcct caaaatgagt gttataatct   1500

ccatcctttt tagtgatctt atccctcaaa actaaagctt tagatttgga ttcgtcaaaa   1560

tttttcttga tatcattaac ggtattgtca taatagaatt tatagattaa atgttgtaat   1620

aataagtcac aatatataaa catatcttta agtacaatag acttccatat attacggaaa   1680

tggtcaaaat tatcagcagc tggaccttcc aatgtaccat aggccttgtt tgatatttca   1740

tcaaccaata acttatattt tgaagagata gtggatgcat tatcaaatat tctagccaat   1800

tcttctttct tcataaggga atattgttca ggaaaacatt tttccaattc ttttttcaat   1860

ttattcttct ccttggtttt ttcttcaatg tagtctttat gaccatcgtt caccctatct   1920

cgttccaata tcataacact atgtttgtat atataagata aacaaacttc attaaatata   1980

actattcttc tagaatacgg aagaagctga tatccaaatc gttcactaga ccaaccagct   2040

tcactaggcc aaccagttcc actaggccaa ccagttccac taggcccacc agcttcacta   2100

ggcccaccag cttcactagg cccaccagct tcactaggcc caccagcttc actaggccaa   2160

ccagttccac taggcccacc agcttcacta ggcccaccag cttcactggg cccaacagtt   2220

ccactaggcc caccagcttc actaggccca ccagcttcgg gatcggtatc acttgcaaag   2280

acagcaccgc tcattaaaaa gagtgtaata taaggaacta atattgattt aaatgacacc   2340

atctttataa accatagtta ttggtacatt attagtacat tattggtata tgattggtac   2400

gtggtagtga ttgtggtgct gcatctagtt                                    2430
```

<210> SEQ ID NO 41
<211> LENGTH: 128
<212> TYPE: PRT
<213> ORGANISM: Babesia microti

<400> SEQUENCE: 41

```
Tyr Cys Val Asp Lys Asn Asp Val Ser Leu Trp Lys Ser Lys Pro Ile
 1               5                  10                  15

Thr Thr Val Ser Thr Thr Asn Asp Thr Ile Thr Asn Thr His Thr Thr
            20                  25                  30

Asn Val Ile Asn Ala Asn Leu Ile Gly His Phe Asn Tyr Lys Asp Arg
        35                  40                  45

Glu Pro Leu Thr Ile Val Phe Val Tyr Met Ile Asp Glu Ser Glu Gln
    50                  55                  60

Asn Lys Leu Ser His Pro Asn Lys Ile Asp Lys Ile Lys Ile Ser Asp
```

-continued

```
65                  70                  75                  80

Tyr Ile Ile Glu Phe Asp Asp Asn Ala Lys Leu Pro Thr Gly Ser Val
                85                  90                  95

Ile Asp Leu Asn Ile Tyr Thr Cys Lys His Asn Asn Pro Val Leu Ile
            100                 105                 110

Glu Phe Tyr Val Ser Ile Glu Gly Ser Phe Cys Tyr Tyr Phe Ser His
        115                 120                 125


<210> SEQ ID NO 42
<211> LENGTH: 1271
<212> TYPE: DNA
<213> ORGANISM: Babesia microti

<400> SEQUENCE: 42

tgagaaaacg catataattg taactacgcc agagaagttt gacgtagtta cacgtaaaac     60

aggcaatgag cccctgcttg agcggcttag attggttata attgatgaaa tacacctact    120

ccatgacact aggggtccag tgctggaggc tattgtggcc cgcctgagtc agaggcccga    180

acgcgtaagg ctagttggtc tatcggccac gcttccaaac tacgaagacg tggctagatt    240

tctcactgtt aatctagacc gagggctttt ctactttggc agccacttta ggcctgtgcc    300

cttggagcag gtgtattatg gcgtgaagga gaagaaggct atcaaacgtt tcaacgcaat    360

caacgaaatt ctctaccaag aggtgattaa cgatgtttct agctgccaaa ttcttgtttt    420

tgtgcattct agaaaggaaa cgtacaggac ggcaaaattt atcaaagaca cggccctttc    480

acgggacaac ttgggagcct aaaccctaaa ccctaaaccc taaaccctaa ccctaaaccc    540

taaaccctaa accctaaacc ctaaacccta accctaaccc taaccctaac cctaacctag    600

ccttcattga cgtctatccc caatcttaga aaaatcttca aatcgattct agaataactg    660

gaagcaatta tcagaaattg tataactgct tattagctta ttagcttatt agttaggatg    720

tatgcacatt gatgacaact agatgcagca ccacaatcac taccacgtac caatcatata    780

ccaataatgt actaataatg taccaataac tatggtttat aaagatggtg tcatttaaat    840

caatattagt tccttatatt acactctttt taatgagcgg tgctgtcttt gcaggtgata    900

ccgatcgcga agctggtggg cctagtggaa ctgttgggcc tagtgaagct ggtgggccta    960

gtgaagctgg tgggcctagt gaagctggtg ggcctagtga agctggtggg cctagtgaag   1020

ctggtgggcc tagtgaagct ggtgggccta gtgaagctgg tgggcctagt gaagctggtg   1080

ggcctagtgg aactggttgg cctagtgaag ctggtgggcc tagtgaagct ggtgggccta   1140

gtgaagctgg tgggcctagt ggaactggtt ggcctagtga agctggttgg cctagtgaag   1200

ctggttggcc tagtgaagct ggttggccta gtgaagctgg ttggcctagt gaagctggtt   1260

ggcctagtga a                                                         1271


<210> SEQ ID NO 43
<211> LENGTH: 166
<212> TYPE: PRT
<213> ORGANISM: Babesia microti

<400> SEQUENCE: 43

Glu Lys Thr His Ile Ile Val Thr Thr Pro Glu Lys Phe Asp Val Val
 1               5                  10                  15

Thr Arg Lys Thr Gly Asn Glu Pro Leu Leu Glu Arg Leu Arg Leu Val
            20                  25                  30

Ile Ile Asp Glu Ile His Leu Leu His Asp Thr Arg Gly Pro Val Leu
        35                  40                  45
```

-continued

Glu Ala Ile Val Ala Arg Leu Ser Gln Arg Pro Glu Arg Val Arg Leu
50 55 60

Val Gly Leu Ser Ala Thr Leu Pro Asn Tyr Glu Asp Val Ala Arg Phe
65 70 75 80

Leu Thr Val Asn Leu Asp Arg Gly Leu Phe Tyr Phe Gly Ser His Phe
85 90 95

Arg Pro Val Pro Leu Glu Gln Val Tyr Tyr Gly Val Lys Glu Lys Lys
100 105 110

Ala Ile Lys Arg Phe Asn Ala Ile Asn Glu Ile Leu Tyr Gln Glu Val
115 120 125

Ile Asn Asp Val Ser Ser Cys Gln Ile Leu Val Phe Val His Ser Arg
130 135 140

Lys Glu Thr Tyr Arg Thr Ala Lys Phe Ile Lys Asp Thr Ala Leu Ser
145 150 155 160

Arg Asp Asn Leu Gly Ala
165

<210> SEQ ID NO 44
<211> LENGTH: 154
<212> TYPE: PRT
<213> ORGANISM: Babesia microti

<400> SEQUENCE: 44

Leu Trp Phe Ile Lys Met Val Ser Phe Lys Ser Ile Leu Val Pro Tyr
1 5 10 15

Ile Thr Leu Phe Leu Met Ser Gly Ala Val Phe Ala Gly Asp Thr Asp
20 25 30

Arg Glu Ala Gly Gly Pro Ser Gly Thr Val Gly Pro Ser Glu Ala Gly
35 40 45

Gly Pro Ser Glu Ala Gly Gly Pro Ser Glu Ala Gly Gly Pro Ser Glu
50 55 60

Ala Gly Gly Pro Ser Glu Ala Gly Gly Pro Ser Glu Ala Gly Gly Pro
65 70 75 80

Ser Glu Ala Gly Gly Pro Ser Glu Ala Gly Gly Pro Ser Gly Thr Gly
85 90 95

Trp Pro Ser Glu Ala Gly Gly Pro Ser Glu Ala Gly Gly Pro Ser Glu
100 105 110

Ala Gly Gly Pro Ser Gly Thr Gly Trp Pro Ser Glu Ala Gly Trp Pro
115 120 125

Ser Glu Ala Gly Trp Pro Ser Glu Ala Gly Trp Pro Ser Glu Ala Gly
130 135 140

Trp Pro Ser Glu Ala Gly Trp Pro Ser Glu
145 150

<210> SEQ ID NO 45
<211> LENGTH: 4223
<212> TYPE: DNA
<213> ORGANISM: Babesia microti

<400> SEQUENCE: 45
ctcgtgcctt tctcaactga taacagctaa caaaaagtct cttatcttaa accatcctat 60
acctcgtatt ataatatgaa aagggccttt tctaaatctt tccccaaagt tctgctattt 120
aattaaaaaa aaaaaagact cattcaataa acgggtgggg cagaaagggt acctttccaa 180
gtgttcttcc atgacgaccc acaatgcaaa gttcttctta caaagaaaag agaaagatcc 240

-continued

```
actgagtgat aagtaaccca gctggggccg ggcggtggtg gcgcacacct ttaatcccag    300
cactcgggag gcagaggcag gcggatctct gtgagttcga gaccaggctg gaccgacagc    360
ctccaaaaca atacagagaa accctgtctc ataaaaaacc aaaaaaaaag taacccagct    420
ggatttggta actgtctcag aaacagacta tataaaacct catcacccta caacaagtag    480
gaagctagcg ctccccaccc catcccaaca cacacacaca cacacacaca cacacacaca    540
cacacacaca cacgcacaca cgcacgcacg cacacacgca cgcacgcaca cacgcacaca    600
cgcacgcaca cacgcacaca cgcacgcacg cacgcacgca cgcacgcacg cacgcccttc    660
tgtgtctgtt ctgttcaaga agggtaccac aaaaaagtac cttatggcca catcaatgac    720
aattattact gtatataaaa tgcccccatg gatggcattg tattgtcgaa attaaaggca    780
cccccgaaag aacagcacag aggggctacc accaattaac tcccaggagg aaataaagac    840
agaagtgtga aggagggaga gagggaggga ggaagggagg gagaaaagga gggaaaggaa    900
caaggagtaa cagggacaaa agcagcagat ggtgccaggc aggagtgtgc ctaccacacc    960
gggccttccc gttacttcat ttactctcct ttgcagcctg ggaataaaca agtcacgcgt   1020
cacccggtgt ctcaagctca gcatggcttg atctgagtgc ccgtgtatgt gttcattcta   1080
taactgattt aaggaacaac tttctgctca ttgcctctat cttctcaaac atttcgaagc   1140
agttattttt tataagaaaa tataaaacag gccgactaaa ttcgatcttt ctctccccag   1200
ctgctagttt cttatctagc tgctttaggc agtctccaca gattgcagcc aggcccctat   1260
tctcaattcc atctgacttc tgacagcgct ctccatttct tatttgcagc ttagacatct   1320
tcactgagag caggagtaat tcattcaaat gacaatgagg tatctgaata tcacacaaac   1380
acttcaaatt ctgtttattg gaaatagatc tgctcctgcc ccatcataac aatccttttt   1440
atcttactta acaggggcaa gaaaatcttt cacttcattt cctatcatct caaatgagtt   1500
cctgtacatg aatgacttaa ggtaaccata tccaacaact tgaagccaac cagtccctgg   1560
tcctactaca gacgttaggg aacatatgtg aaaacctggt gtacaaccta aatcataact   1620
agacagaaga cagcactatt tcctggtcac atagaaagca gaatagcatc ctcacaccaa   1680
tgaggaaaat gtcatgaagg caggagagat catgactgag gtgatacttt taccaaagac   1740
ttgccagtga ttaatttctc aattagttag caaaaaatat ggctctctag tgaatttgtg   1800
tccacaccat tttccagatg ttttgatgtc acttaaatca atctaattat ttaagttaaa   1860
aaatgttaca gatcattgct ttttttcttt tttagaagac atcaaaacaa taggatttct   1920
atgaaatatt ctcacttcac agctgtgtca gttaaagtgc tttgggttat acataaagaa   1980
aacagactca agaaagtaag aacaggaatt tggagcttgc aacactgatg ttctttgtaa   2040
aaagagagac tttatccagg gattagattc tgtcacaagg cctggaactc tctcttctca   2100
gccttatttc cccaatatgg attagaatct tacactgcaa gcttcccaca agggtggaca   2160
ggtcctcacc atttgtttca gcaggaaaaa gagtctgtat gcatccgtga tatctaagtc   2220
acaattccag aagtgagctt tcctggctcc tattggtcgg acttaggtca ggtgtcacat   2280
ttccttttgg attagtctgt gattaatgaa tgggcccact ttgctcaccc attaagacaa   2340
taggcttcca ttctcgaagc tggaagcatg acatgtccca cagaaactgt aataagagag   2400
aacataggtt gctgtgtgga gaaacgaggc aaccggcaag tcataagatg acaaagtctt   2460
ggaaagtcta agtcagtggt tctcagcctt ccctaaaccc taaaccctaa accctaaacc   2520
ctaaacccta aaccctaaac ccctaaaccc taaaccctaa accctaaacc ctaaacccta   2580
accctaaacc ctaaacccta aaccctaaac cctaaaccct aaccctaacc ctaaccctaa   2640
```

```
ccctaaccta gccttcattg acgtctatcc ccaatcttag aaaaatcttc aaatcgattc   2700

tagaataact ggaagcaatt atcagaaatt gtataactgc ttattagctt attagcttat   2760

tagttaggat gtatgcacat tgatgacaac tagatgcagc accacaatca ctaccacgta   2820

ccaatcatat accaataatg tactaataat gtaccaataa ctatggttta taaagatggt   2880

gtcatttaaa tcaatattag ttccttatat tacactcttt ttaatgagcg gtgctgtctt   2940

tgcaggtgat accgatcgcg aagctggtgg gcctagtgga actgttgggc ctagtgaagc   3000

tggtgggcct agtgaagctg gtgggcctag tgaagctggt gggcctagtg aagctggtgg   3060

gcctagtgaa gctggtgggc ctagtgaagc tggtgggcct agtgaagctg gtgggcctag   3120

tggaactgtt gggcctagtg aagctggtgg gcctagtgaa gctggtgggc ctagtgaagc   3180

tggtgggcct agtgaagctg gttggcctag tgaagctggt tggcctagtg aagctggttg   3240

gcctagtgaa gctggttggc ctagtgaagc tggttggcct agtgaagctg gttggcctag   3300

tgaacgattt ggatatcagc ttctttggta ttctagaaga atagttatat ttaatgaaat   3360

ttatttatct catatatacg aacatagtgt tatgatattg gaacgagata gggtgaacga   3420

tggtcataaa gactacattg aagaaaaaac caaggagaag aataaattga aaaaagaatt   3480

ggaaaaatgt tttcctgaac aatattccct tatgaagaaa gaagaattgg ctagaataat   3540

tgataatgca tccactatct cttcaaaata taagttattg gttgatgaaa tatccaacaa   3600

agcctatggt acattggaag gtccagctgc tgatgatttt gaccatttcc gtaatatatg   3660

gaagtctatt gtacctaaaa atatgtttct atattgtgac ttattattaa aacatttaat   3720

ccgtttaacc cccagaaaga gctgaccaga caaaggttaa ctcttgaatc ccaggcatca   3780

gcctgggaat ccatcatggg actgatcaag accccctgaa tgtgggtgtc agtgaggagg   3840

cctaggtaat ctattgagcc tcgggcagca gatcagtacc catcccaatt atacacaatt   3900

gcagtgttgt ggtttcacag tgaataattg taggtcacag tccattatat tgatgtcaca   3960

gtttttaatt gtcatgtcac agtgcaagct agtgatgtca gagtgtataa ctgtgttcat   4020

agagaatgta ttgatgtcac agtcaataat cgtgatgtca tagtgcagta tattgatgtc   4080

acaatgtata attgtgatgt taaagtgcaa gatagtgaag tcacagtata taattgtgat   4140

gtcatattgc attataatga tgtcacactt tataattttt tacatacagc actatagtga   4200

tgtaacagcc aataattgtg atg                                           4223
```

```
<210> SEQ ID NO 46
<211> LENGTH: 294
<212> TYPE: PRT
<213> ORGANISM: Babesia microti

<400> SEQUENCE: 46

Leu Trp Phe Ile Lys Met Val Ser Phe Lys Ser Ile Leu Val Pro Tyr
 1               5                  10                  15

Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
        35                  40                  45

Gly Pro Ser Glu Ala Gly Gly Pro Ser Glu Ala Gly Gly Pro Ser Glu
    50                  55                  60

Ala Gly Gly Pro Ser Glu Ala Gly Gly Pro Ser Glu Ala Gly Gly Pro
65                  70                  75                  80

Ser Glu Ala Gly Gly Pro Ser Gly Thr Val Gly Pro Ser Glu Ala Gly
```

-continued

```
                85                  90                  95

Gly Pro Ser Glu Ala Gly Gly Pro Ser Glu Ala Gly Gly Pro Ser Glu
            100                 105                 110

Ala Gly Trp Pro Ser Glu Ala Gly Trp Pro Ser Glu Ala Gly Trp Pro
        115                 120                 125

Ser Glu Ala Gly Trp Pro Ser Glu Ala Gly Trp Pro Ser Glu Ala Gly
    130                 135                 140

Trp Pro Ser Glu Arg Phe Gly Tyr Gln Leu Leu Trp Tyr Ser Arg Arg
145                 150                 155                 160

Ile Val Ile Phe Asn Glu Ile Tyr Leu Ser His Ile Tyr Glu His Ser
                165                 170                 175

Val Met Ile Leu Glu Arg Asp Arg Val Asn Asp Gly His Lys Asp Tyr
            180                 185                 190

Ile Glu Glu Lys Thr Lys Glu Lys Asn Lys Leu Lys Lys Glu Leu Glu
        195                 200                 205

Lys Cys Phe Pro Glu Gln Tyr Ser Leu Met Lys Lys Glu Glu Leu Ala
    210                 215                 220

Arg Ile Ile Asp Asn Ala Ser Thr Ile Ser Ser Lys Tyr Lys Leu Leu
225                 230                 235                 240

Val Asp Glu Ile Ser Asn Lys Ala Tyr Gly Thr Leu Glu Gly Pro Ala
                245                 250                 255

Ala Asp Asp Phe Asp His Phe Arg Asn Ile Trp Lys Ser Ile Val Pro
            260                 265                 270

Lys Asn Asn Phe Leu Tyr Cys Asp Leu Leu Leu Lys His Leu Ile Arg
        275                 280                 285

Leu Thr Pro Arg Lys Ser
    290


<210> SEQ ID NO 47
<211> LENGTH: 30
<212> TYPE: PRT
<213> ORGANISM: Artificial Sequence
<220> FEATURE:
<223> OTHER INFORMATION: Synthetic peptide of repeat region of antigen
      BMNI-3 (SEQ ID NO:3)

<400> SEQUENCE: 47

Ser Glu Ala Gly Gly Pro Ser Glu Ala Gly Gly Pro Ser Gly Thr Gly
 1               5                  10                  15

Trp Thr Ser Gly Thr Gly Trp Pro Ser Glu Ala Gly Trp Ser
            20                  25                  30


<210> SEQ ID NO 48
<211> LENGTH: 30
<212> TYPE: PRT
<213> ORGANISM: Artificial Sequence
<220> FEATURE:
<223> OTHER INFORMATION: Synthetic peptide of repeat region of antigen
      BMNI-3 (SEQ ID NO:3)

<400> SEQUENCE: 48

Glu Ala Gly Gly Pro Ser Gly Thr Val Gly Pro Ser Gly Thr Gly Trp
 1               5                  10                  15

Pro Ser Glu Ala Gly Trp Gly Ser Glu Ala Gly Trp Ser Ser
            20                  25                  30


<210> SEQ ID NO 49
<211> LENGTH: 367
<212> TYPE: PRT
```

-continued

<213> ORGANISM: Babesia microti

<400> SEQUENCE: 49

```
Met Val Ser Phe Lys Ser Ile Leu Val Pro Tyr Ile Thr Leu Phe Leu
 1               5                  10                  15

Met Ser Gly Ala Val Phe Ala Ser Asp Thr Asp Pro Glu Ala Gly Gly
            20                  25                  30

Pro Ser Glu Ala Gly Gly Pro Ser Gly Thr Val Gly Pro Ser Glu Ala
        35                  40                  45

Gly Gly Pro Ser Glu Ala Gly Gly Pro Ser Gly Thr Gly Trp Pro Ser
    50                  55                  60

Glu Ala Gly Gly Pro Ser Glu Ala Gly Gly Pro Ser Glu Ala Gly Gly
65                  70                  75                  80

Pro Ser Glu Ala Gly Gly Pro Ser Gly Thr Gly Ser Glu Ala Gly Gly
                85                  90                  95

Trp Pro Ser Gly Thr Gly Trp Pro Ser Glu Ala Gly Trp Ser Ser Glu
            100                 105                 110

Arg Phe Gly Tyr Gln Leu Leu Pro Tyr Ser Arg Arg Ile Val Ile Phe
        115                 120                 125

Asn Glu Val Cys Leu Ser Tyr Ile Tyr Lys His Ser Val Met Ile Leu
    130                 135                 140

Glu Arg Asp Arg Val Asn Asp Gly His Lys Asp Tyr Ile Glu Glu Lys
145                 150                 155                 160

Thr Lys Glu Lys Asn Lys Leu Lys Lys Glu Leu Glu Lys Cys Phe Pro
                165                 170                 175

Glu Gln Tyr Ser Leu Met Lys Lys Glu Glu Leu Ala Arg Ile Phe Asp
            180                 185                 190

Asn Ala Ser Thr Ile Ser Ser Lys Tyr Lys Leu Leu Val Asp Glu Ile
        195                 200                 205

Ser Asn Lys Ala Tyr Gly Thr Leu Glu Gly Pro Ala Ala Asp Asn Phe
    210                 215                 220

Asp His Phe Arg Asn Ile Trp Lys Ser Ile Val Leu Lys Asp Met Phe
225                 230                 235                 240

Ile Tyr Cys Asp Leu Leu Leu Gln His Leu Ile Tyr Lys Phe Tyr Tyr
                245                 250                 255

Asp Asn Thr Val Asn Asp Ile Lys Lys Asn Phe Asp Glu Ser Lys Ser
            260                 265                 270

Lys Ala Leu Val Leu Arg Asp Lys Ile Thr Lys Lys Asp Gly Asp Tyr
        275                 280                 285

Asn Thr His Phe Glu Asp Met Ile Lys Glu Leu Asn Ser Ala Ala Glu
    290                 295                 300

Glu Phe Asn Lys Ile Val Asp Ile Met Ile Ser Asn Ile Gly Asp Tyr
305                 310                 315                 320

Asp Glu Tyr Asp Ser Ile Ala Ser Phe Lys Pro Phe Leu Ser Met Ile
                325                 330                 335

Thr Glu Ile Thr Lys Ile Thr Lys Val Ser Asn Val Ile Ile Pro Gly
            340                 345                 350

Ile Lys Ala Leu Thr Leu Thr Val Phe Leu Ile Phe Ile Thr Lys
        355                 360                 365
```

<210> SEQ ID NO 50
<211> LENGTH: 1908
<212> TYPE: DNA
<213> ORGANISM: Babesia microti -continued

<400> SEQUENCE: 50
aaaagattta atgaacatac tgacatgaat ggtattcatt attattatat tgatggtagt 60
ttacttgcga gtggcgaagt tacatctaat tttcgttata tttctaaaga atatgaatat 120
gagcatacag aattagcaaa agagcattgc aagaaagaaa aatgtgtaaa tgtggataac 180
attgaggata ataatttgaa aatatatgcg aaacagttta aatctgtagt tactactcca 240
gctgatgtag cgggtgtgtc agatggattt tttatacgtg gccaaaatct tggtgctgtg 300
ggcagtgtaa atgaacaacc taatactgtt ggtatgagtt tagaacaatt catcaagaac 360
gagctttatt cttttagtaa tgaaatttat catacaatat ctagtcaaat cagtaattct 420
ttcttaataa tgatgtctga tgcaattgtt aaacatgata actatatttt aaaaaaagaa 480
ggtgaaggct gtgaacaaat ctacaattat gaggaattta tagaaaagtt gaggggtgct 540
agaagtgagg ggaataatat gtttcaggaa gctctgataa ggtttaggaa tgctagtagt 600
gaagaaatgg ttaatgctgc aagttatcta tccgccgccc ttttcagata taaggaattt 660
gatgatgaat tattcaaaaa ggccaacgat aattttggac gcgatgatgg atatgatttt 720
gattatataa atacaaagaa agagttagtt atacttgcca gtgtgttgga tggtttggat 780
ttaataatgg aacgtttgat cgaaaatttc agtgatgtca ataatacaga tgatattaag 840
aaggcatttg acgaatgcaa atctaatgct attatattga agaaaaagat acttgacaat 900
gatgaagatt ataagattaa ttttagggaa atggtgaatg aagtaacatg tgcaaacaca 960
aaatttgaag ccctaaatga tttgataatt tccgactgtg agaaaaaagg tattaagata 1020
aacagagatg tgatttcaag ctacaaattg cttctttcca caatcaccta tattgttgga 1080
gctggagttg aagctgtaac tgttagtgtg tctgctacat ctaatggaac tgaatctggt 1140
ggagctggta gtggaactgg aactagtgtg tctgctacat ctactttaac tggtaatggt 1200
ggaactgaat ctggtggaac agctggaact actacgtcta gtggaactga agctggtgga 1260
actagtggaa ctactacgtc tagtggagct gctagtggta aagctggaac tggaacagct 1320
ggaactacta cgtctagtga aggtgctggt agtgataaag ctggaactgg aactagtgga 1380
actactacgt ctagtggaac tggtgctggt ggagctggta gtggtggacc tagtggacat 1440
gcttctaatg caaaaattcc tggaataatg acactaactc tatttgcatt attaacattt 1500
attgtaaatt gaatgaaaca catgatttat acattattat atattacaaa atttacacat 1560
tatttatgta tgaacgaacg aacatcttgc tcttaaataa agaaattgag atatatatgg 1620
aaatagatta aagtaacatg agaaagatga atataatatt agaatatgaa atttaacaga 1680
aataaaatga agtaaaagag tgtattttgt aataatttat aataaattag tatacaatga 1740
ttatattaca aatggctatt aaatatttta ttaattaaat attgattagt aatgatatta 1800
tgtatgtaca tgttagggtt gattgttata cattgtgaat atattatata attgtatatt 1860
atattgattg atataatgta gaggatattt ttttaaatag tatttaat 1908

<210> SEQ ID NO 51
<211> LENGTH: 1460
<212> TYPE: DNA
<213> ORGANISM: Babesia microti

<400> SEQUENCE: 51
aatccaacat ctagcctagt tagtatatat aggttaatat cacattatag attatctttg 60
gatgattggt tattatataa catgtcgctg aatgacgatt attttgctag ataatataac 120
taccggtgat tctgaggacc tactttaaag agaataatta acatatctac cagaatcagt 180

-continued

```
tccaatttat gtattttaaa gctaatcact actcgaaaac tacggtgaaa atggaaaaac    240

aagtggaagc tgtatgtcgt ggaaagtcac tacattttat gtgggcaaat ttaataattc    300

taaatactat gtttttgatg ttaaaaagcg aaaaacacac tttaatgcac attttaacat    360

catctgtata atatatatat cagcgttgaa atcatatggc aaaggtaata aagcgttaca    420

ttttgagcga ataaaggcac atatgcaaac gtatgaagcc ttgtatattt gtggaattat    480

attatgctag taatttgtga ttaataatgg caatatttat atacaaatat tcgagcgttc    540

tattatatgc atgcacataa ttaatcacaa actctcatat catggggcgg tttcgcccat    600

cataaacatt actgttagca ctctggtaga ttagcatggt gaatctctcg atacctgggc    660

tactgttgct ttccgcatat tccttaaatt ctgcaagtgc gggggatgta tatgagatat    720

cttctggtaa tccacccgac atagagccaa catctacttc tctagaaaca aatgtagtta    780

ccaactatat tccagaaccc aatgcggatt cagaatctgt acatgttgaa atccaggaac    840

atgataacat caatccacaa gacgcttgcg atagtgagcc gctcgaacaa atggattctg    900

ataccagggt gttgcccgaa agtttggatg agggggtacc acaccaattc tctagattag    960

ggcaccactc agacatggca tctgatataa atgatgaaga accatcattt aaaatcggcg   1020

agaatgacat aattcaacca ccctgggaag atacagctcc ataccattca atagatgatg   1080

aagagcttga caacttaatg agactaacgg cgcaagaaac aagtgacgat catgaagaag   1140

ggaatggcaa actcaatacg aataaaagtg agaagactga aagaaaatcg catgatactc   1200

agacaccgca agaaatatat gaagagcttg acaacttact gagactaacg gcacaagaaa   1260

tatatgaaga gcgtaaagaa gggcatggca aacccaatac gaataaaagt gagaaggctg   1320

aaagaaaatc gcatgatact cagacaacgc aagaaatatg tgaagagtgt gaagaagggc   1380

atgacaaaat caataagaat aaaagtggaa atgctggaat aaaatcgtat gatactcaga   1440

caccgcagga aacaagtgac                                               1460
```

<210> SEQ ID NO 52
<211> LENGTH: 503
<212> TYPE: PRT
<213> ORGANISM: Babesia microti

<400> SEQUENCE: 52

```
Lys Arg Phe Asn Glu His Thr Asp Met Asn Gly Ile His Tyr Tyr Tyr
 1               5                  10                  15

Ile Asp Gly Ser Leu Leu Ala Ser Gly Glu Val Thr Ser Asn Phe Arg
            20                  25                  30

Tyr Ile Ser Lys Glu Tyr Glu Tyr Glu His Thr Glu Leu Ala Lys Glu
        35                  40                  45

His Cys Lys Lys Glu Lys Cys Val Asn Val Asp Asn Ile Glu Asp Asn
    50                  55                  60

Asn Leu Lys Ile Tyr Ala Lys Gln Phe Lys Ser Val Val Thr Thr Pro
65                  70                  75                  80

Ala Asp Val Ala Gly Val Ser Asp Gly Phe Phe Ile Arg Gly Gln Asn
                85                  90                  95

Leu Gly Ala Val Gly Ser Val Asn Glu Gln Pro Asn Thr Val Gly Met
            100                 105                 110

Ser Leu Glu Gln Phe Ile Lys Asn Glu Leu Tyr Ser Phe Ser Asn Glu
        115                 120                 125

Ile Tyr His Thr Ile Ser Ser Gln Ile Ser Asn Ser Phe Leu Ile Met
    130                 135                 140
```

-continued

Met Ser Asp Ala Ile Val Lys His Asp Asn Tyr Ile Leu Lys Lys Glu
145 150 155 160

Gly Glu Gly Cys Glu Gln Ile Tyr Asn Tyr Glu Glu Phe Ile Glu Lys
165 170 175

Leu Arg Gly Ala Arg Ser Glu Gly Asn Asn Met Phe Gln Glu Ala Leu
180 185 190

Ile Arg Phe Arg Asn Ala Ser Ser Glu Glu Met Val Asn Ala Ala Ser
195 200 205

Tyr Leu Ser Ala Ala Leu Phe Arg Tyr Lys Glu Phe Asp Asp Glu Leu
210 215 220

Phe Lys Lys Ala Asn Asp Asn Phe Gly Arg Asp Asp Gly Tyr Asp Phe
225 230 235 240

Asp Tyr Ile Asn Thr Lys Lys Glu Leu Val Ile Leu Ala Ser Val Leu
245 250 255

Asp Gly Leu Asp Leu Ile Met Glu Arg Leu Ile Glu Asn Phe Ser Asp
260 265 270

Val Asn Asn Thr Asp Asp Ile Lys Lys Ala Phe Asp Glu Cys Lys Ser
275 280 285

Asn Ala Ile Ile Leu Lys Lys Lys Ile Leu Asp Asn Asp Glu Asp Tyr
290 295 300

Lys Ile Asn Phe Arg Glu Met Val Asn Glu Val Thr Cys Ala Asn Thr
305 310 315 320

Lys Phe Glu Ala Leu Asn Asp Leu Ile Ile Ser Asp Cys Glu Lys Lys
325 330 335

Gly Ile Lys Ile Asn Arg Asp Val Ile Ser Ser Tyr Lys Leu Leu Leu
340 345 350

Ser Thr Ile Thr Tyr Ile Val Gly Ala Gly Val Glu Ala Val Thr Val
355 360 365

Ser Val Ser Ala Thr Ser Asn Gly Thr Glu Ser Gly Gly Ala Gly Ser
370 375 380

Gly Thr Gly Thr Ser Val Ser Ala Thr Ser Thr Leu Thr Gly Asn Gly
385 390 395 400

Gly Thr Glu Ser Gly Gly Thr Ala Gly Thr Thr Thr Ser Ser Gly Thr
405 410 415

Glu Ala Gly Gly Thr Ser Gly Thr Thr Thr Ser Ser Gly Ala Ala Ser
420 425 430

Gly Lys Ala Gly Thr Gly Thr Ala Gly Thr Thr Thr Ser Ser Glu Gly
435 440 445

Ala Gly Ser Asp Lys Ala Gly Thr Gly Thr Ser Gly Thr Thr Thr Ser
450 455 460

Ser Gly Thr Gly Ala Gly Gly Ala Gly Ser Gly Gly Pro Ser Gly His
465 470 475 480

Ala Ser Asn Ala Lys Ile Pro Gly Ile Met Thr Leu Thr Leu Phe Ala
485 490 495

Leu Leu Thr Phe Ile Val Asn
500

<210> SEQ ID NO 53
<211> LENGTH: 275
<212> TYPE: PRT
<213> ORGANISM: Babesia microti

<400> SEQUENCE: 53

Met Val Asn Leu Ser Ile Pro Gly Leu Leu Leu Leu Ser Ala Tyr Ser

-continued

```
 1               5                   10                  15

Leu Asn Ser Ala Ser Ala Gly Asp Val Tyr Glu Ile Ser Ser Gly Asn
            20                  25                  30

Pro Pro Asp Ile Glu Pro Thr Ser Thr Ser Leu Glu Thr Asn Val Val
        35                  40                  45

Thr Asn Tyr Ile Pro Glu Pro Asn Ala Asp Ser Glu Ser Val His Val
    50                  55                  60

Glu Ile Gln Glu His Asp Asn Ile Asn Pro Gln Asp Ala Cys Asp Ser
65                  70                  75                  80

Glu Pro Leu Glu Gln Met Asp Ser Asp Thr Arg Val Leu Pro Glu Ser
                85                  90                  95

Leu Asp Glu Gly Val Pro His Gln Phe Ser Arg Leu Gly His His Ser
            100                 105                 110

Asp Met Ala Ser Asp Ile Asn Asp Glu Glu Pro Ser Phe Lys Ile Gly
        115                 120                 125

Glu Asn Asp Ile Ile Gln Pro Arg Trp Glu Asp Thr Ala Pro Tyr His
    130                 135                 140

Ser Ile Asp Asp Glu Glu Leu Asp Asn Leu Met Arg Leu Thr Ala Gln
145                 150                 155                 160

Glu Thr Ser Asp Asp His Glu Glu Gly Asn Gly Lys Leu Asn Thr Asn
                165                 170                 175

Lys Ser Glu Lys Thr Glu Arg Lys Ser His Asp Thr Gln Thr Pro Gln
            180                 185                 190

Glu Ile Tyr Glu Glu Leu Asp Asn Leu Leu Arg Leu Thr Ala Gln Glu
        195                 200                 205

Ile Tyr Glu Glu Arg Lys Glu Gly His Gly Lys Pro Asn Thr Asn Lys
    210                 215                 220

Ser Glu Lys Ala Glu Arg Lys Ser His Asp Thr Gln Thr Thr Gln Glu
225                 230                 235                 240

Ile Cys Glu Glu Cys Glu Glu Gly His Asp Lys Ile Asn Lys Asn Lys
                245                 250                 255

Ser Gly Asn Ala Gly Ile Lys Ser Tyr Asp Thr Gln Thr Pro Gln Glu
            260                 265                 270

Thr Ser Asp
        275


<210> SEQ ID NO 54
<211> LENGTH: 22
<212> TYPE: DNA
<213> ORGANISM: Artificial Sequence
<220> FEATURE:
<223> OTHER INFORMATION: PCR Primer

<400> SEQUENCE: 54

tttgcaggtg ataccgatcg cg                                               22


<210> SEQ ID NO 55
<211> LENGTH: 24
<212> TYPE: DNA
<213> ORGANISM: Artificial Sequence
<220> FEATURE:
<223> OTHER INFORMATION: PCR Primer

<400> SEQUENCE: 55

tggtattcta gaagaatagt tata                                             24


<210> SEQ ID NO 56
```

-continued

<211> LENGTH: 306
<212> TYPE: DNA
<213> ORGANISM: Babesia microti

<400> SEQUENCE: 56
ttgcaggtga taccgatcgc gaagctggtg ggcctagtgg aactgttggg cccagtgaag 60
ctggtgggcc tagtgaagct ggtgggccta gtggaactgt tgggcccagt gaagctggtg 120
ggcctagtga agctggtggg cctagtggaa ctggttggcc tagtgaagct ggtgggccta 180
gtggaactgt tgggcccagt gaagctggtg ggcctagtga agctggtggg cctagtggaa 240
ctggttggcc tagtggaact ggttggccta gtgaagttgg ttggcccatt gaaccatttg 300
gatatc 306

<210> SEQ ID NO 57
<211> LENGTH: 318
<212> TYPE: DNA
<213> ORGANISM: Babesia microti

<400> SEQUENCE: 57
ttgcaggtga taccgatcgc gaagctggtg ggcctagtgg aactgttggg cccagtgaag 60
ctggtgggcc tagtgaagct ggtgggccta gtggaactgt tgggcccagt gaagctggtg 120
ggcctagtga agctggtggg cctagtggaa ctggttggcc tagtgaagct ggtgggccta 180
gtggaactgt tgggcccagt gaagctggtg ggcctagtga agctggtggg cctagtggaa 240
ctggttggcc tagtggaact ggttggccta gtgaagttgg ttggcctaat gaaccatttg 300
gatatcacct tctttggt 318

<210> SEQ ID NO 58
<211> LENGTH: 358
<212> TYPE: DNA
<213> ORGANISM: Babesia microti

<400> SEQUENCE: 58
ttgcaggtga taccgatcgc gaagctggtg ggcctagtgg aactgttggg cctagtgaag 60
ctggtgggcc tagtgaagct ggtgggccta gtgaagctgg tgggcctagt gaagctggtg 120
ggcctagtga agctggtggg cctagtgaag ctggtgggcc tagtgaagct ggtgggccta 180
gtgaagctgg tgggcctagt gaagctggtg ggcctagtga agctggttgg cctagtgaag 240
ctggttggcc tagtgaagct ggtgggccta gtggaactgg ttggcctagt gaagctggtt 300
ggcctagtga agctggttgg cctagtgaag ctggttggcc tagtgaagct ggttggcc 358

<210> SEQ ID NO 59
<211> LENGTH: 409
<212> TYPE: DNA
<213> ORGANISM: Babesia microti

<400> SEQUENCE: 59
tgcaggtgat accgatcgcg aagctggtgg gcctagtgga actgttgggc ctagtgaagc 60
tggtgggcct agtgaagctg gtgggcctag tgaagctggt gggcctagtg aagctggtgg 120
gcctagtgaa gctggtgggc ctagtgaagc tggtgggcct agtgaagctg gtgggcctag 180
tgaagctggt gggcctagtg aagctggtgg gcctagtgaa gctggttggc ctagtgaagc 240
tggttggcct agtgaagctg gtgggcctag tggaactggt tggcctagtg aagctggttg 300
gcctagtgaa gctggttggc ctagtgaagc tggttggcct agtgaagctg gttggcctag 360
tgaacgattt ggatatcagc ttctttggta ttctagaaga atagttata 409

-continued

<210> SEQ ID NO 60
<211> LENGTH: 351
<212> TYPE: DNA
<213> ORGANISM: Babesia microti

<400> SEQUENCE: 60
gtgaagctgg tgggcctagt ggaactgttg ggcctagtga agctggtggg cctagtgaag 60
ctggtgggcc tagtgaagct ggtgggccta gtgaagctgg tgggcctagt gaagctggtg 120
ggcctagtga agctggtggg cctagtgaag ctggtgggcc tagtgaagct ggtgggccta 180
gtgaagctgg tgggcctagt gaagctggtt ggcctagtga agctggttgg cctagtgaag 240
ctggtgggcc tagtggaact ggttggccta gtgaagctgg ttggcctagt gaagctggtt 300
ggcctagtga agctggttgg cctagtgaag ctggttggcc tagtgaacga t 351

<210> SEQ ID NO 61
<211> LENGTH: 410
<212> TYPE: DNA
<213> ORGANISM: Babesia microti

<400> SEQUENCE: 61
aggtgatacc gatcgcgaag ctggtgggcc tagtggaact gttgggccta gtgaagctgg 60
tgggcctagt gaagctggtg ggcctagtga agctggtggg cctagtgaag ctggtgggcc 120
tagtgaagct ggtgggccta gtgaagctgg tgggcctagt gaagctggtg ggcctagtga 180
agctggtggg cctagtgaag ctggtgggcc tagtgaagct ggtgggccta gtgaagctgg 240
ttggcctagt gaagctggtt ggcctagtga agctggtggg cctagtggaa ctggttggcc 300
tagtgaagct ggttggccta gtgaagctgg ttggcctagt gaagctggtt ggcctagtga 360
agctggttgg cctagtgaac gatttggata tcagcttctt tggtattcta 410

<210> SEQ ID NO 62
<211> LENGTH: 416
<212> TYPE: DNA
<213> ORGANISM: Babesia microti

<400> SEQUENCE: 62
ttgcaggtga taccgatcgc gaagctggtg ggcctagtgg aactgttggg cctagtgaag 60
ctggtgggcc tagtgaagct ggtgggccta gtgaagctgg tgggcctagt gaagctggtg 120
ggcctagtga agctggtggg cctagtgaag ctggtgggcc tagtgaagct ggtgggccta 180
gtgaagctgg tgggcctagt gaagctggtg ggcctagtga agctggtggg cctagtgaag 240
ctggtgggcc tagtgaagct ggttggccta gtgaagctgg ttggcctagt gaagctggtg 300
ggcctagtgg aactggttgg cctagtgaag ctggttggcc tagtgaagct ggttggccta 360
gtgaagctgg ttggcctagt gaagctggtt ggcctagtga acgatttgga tatcag 416

<210> SEQ ID NO 63
<211> LENGTH: 356
<212> TYPE: DNA
<213> ORGANISM: Babesia microti

<400> SEQUENCE: 63
ttgcaggtga taccgatcgc gaagctggtg ggcctagtgg aactgttggg cctagtgaag 60
ctggtgggcc tagtgaagct ggtgggccta gtgaagctgg tgggcctagt gaagctggtg 120
ggcctagtga agctggtggg cctagtgaag ctggtgggcc tagtgaagct ggtgggccta 180

-continued

```
gtgaagctgg tgggcctagt ggaactggtt ggcctagtga agctggttgg cctagtgaag    240

ctggttggcc tagtgaagct ggttggccta gtgaagctgg ttggcctagt gaagctggtt    300

ggcctagtga acgatttgga tatcagcttc tttggtattc tagaagaata gttata        356


<210> SEQ ID NO 64
<211> LENGTH: 285
<212> TYPE: DNA
<213> ORGANISM: Babesia microti

<400> SEQUENCE: 64

ttgcaggtga taccgatcgc gaagctggtg ggcctagtgg aactgttggg cctagtgaag     60

ctggtgggcc tagtgaagct ggtgggccta gtgaagctgg tgggcctagt gaagctggtg    120

ggcctagtga agctggtggg cctagtgaag ctggtgggcc tagtgaagct ggtgggccta    180

gtggaactgg ttggcctagt gaagctggtt ggcctagtga agctggttgg cctagtgaag    240

ctggttggcc tagtgaagct ggttggccta gtgaagctgg ttggc                    285


<210> SEQ ID NO 65
<211> LENGTH: 342
<212> TYPE: DNA
<213> ORGANISM: Babesia microti

<400> SEQUENCE: 65

ttgcaggtga taccgatcgc gaagctggtg ggcctagtgg aactgttggg cctagtgaag     60

ctggtgggcc tagtgaagct ggtgggccta gtgaagctgg tgggcctagt gaagctggtg    120

ggcctagtga agctggtggg cctagtgaag ctggtgggcc tagtgaagct ggtgggccta    180

gtgaagctgg tgggcctagt ggaactggtt ggcctagtga agctggttgg cctagtgaag    240

ctggttggcc tagtgaagct ggttggccta gtgaagctgg ttggcctagt gaagctggtt    300

ggcctagtga acgatttgga tatcagcttc tttggtattc ta                       342


<210> SEQ ID NO 66
<211> LENGTH: 363
<212> TYPE: DNA
<213> ORGANISM: Babesia microti

<400> SEQUENCE: 66

ttgcaggtga taccgatcgc gaagctggtg ggcctagtgg aactgttggg cctagtgaag     60

ctggtgggcc tagtgaagct ggtgggccta gtgaagctgg tgggcctagt gaagctggtg    120

ggcctagtga agctggtggg cctagtgaag ctggtgggcc tagtgaagct ggtgggccta    180

gtgaagctgg tgggcctagt gaagctggtg ggcctagtgg aactggttgg cctagtgaag    240

ctggttggcc tagtgaagct ggttggccta gtgaagctgg ttggcctagt gaagctggtt    300

ggcctagtga agctggttgg cctagtgaac gatttggata tcagcttctt tggtattcta    360

gaa                                                                  363


<210> SEQ ID NO 67
<211> LENGTH: 363
<212> TYPE: DNA
<213> ORGANISM: Babesia microti

<400> SEQUENCE: 67

ttgcaggtga taccgatcgc gaagctggtg ggcctagtgg aactgttggg cctagtgaag     60

ctggtgggcc tagtgaagct ggtgggccta gtgaagctgg tgggcctagt gaagctggtg    120

ggcctagtga agctggtggg cctagtgaag ctggtgggcc tagtgaagct ggtgggccta    180
```

gtgaagctgg tgggcctagt gaagctggtg ggcctagtgg aactggttgg cctagtgaag 240
ctggttggcc tagtgaagct ggttggccta gtgaagctgg ttggcctagt gaagctggtt 300
ggcctagtga agctggttgg cctagtgaac gatttggata tcagcttctt tggtattcta 360
gaa 363

<210> SEQ ID NO 68
<211> LENGTH: 101
<212> TYPE: PRT
<213> ORGANISM: Babesia microti

<400> SEQUENCE: 68

Ala Gly Asp Thr Asp Arg Glu Ala Gly Gly Pro Ser Gly Thr Val Gly
1 5 10 15

Pro Ser Glu Ala Gly Gly Pro Ser Glu Ala Gly Gly Pro Ser Gly Thr
20 25 30

Val Gly Pro Ser Glu Ala Gly Gly Pro Ser Glu Ala Gly Gly Pro Ser
35 40 45

Gly Thr Gly Trp Pro Ser Glu Ala Gly Gly Pro Ser Gly Thr Val Gly
50 55 60

Pro Ser Glu Ala Gly Gly Pro Ser Glu Ala Gly Gly Pro Ser Gly Thr
65 70 75 80

Gly Trp Pro Ser Gly Thr Gly Trp Pro Ser Glu Val Gly Trp Pro Ile
85 90 95

Glu Pro Phe Gly Tyr
100

<210> SEQ ID NO 69
<211> LENGTH: 105
<212> TYPE: PRT
<213> ORGANISM: Babesia microti

<400> SEQUENCE: 69

Ala Gly Asp Thr Asp Arg Glu Ala Gly Gly Pro Ser Gly Thr Val Gly
1 5 10 15

Pro Ser Glu Ala Gly Gly Pro Ser Glu Ala Gly Gly Pro Ser Gly Thr
20 25 30

Val Gly Pro Ser Glu Ala Gly Gly Pro Ser Glu Ala Gly Gly Pro Ser
35 40 45

Gly Thr Gly Trp Pro Ser Glu Ala Gly Gly Pro Ser Gly Thr Val Gly
50 55 60

Pro Ser Glu Ala Gly Gly Pro Ser Glu Ala Gly Gly Pro Ser Gly Thr
65 70 75 80

Gly Trp Pro Ser Gly Thr Gly Trp Pro Ser Glu Val Gly Trp Pro Asn
85 90 95

Glu Pro Phe Gly Tyr His Leu Leu Trp
100 105

<210> SEQ ID NO 70
<211> LENGTH: 118
<212> TYPE: PRT
<213> ORGANISM: Babesia microti

<400> SEQUENCE: 70

Ala Gly Asp Thr Asp Arg Glu Ala Gly Gly Pro Ser Gly Thr Val Gly
1 5 10 15

Pro Ser Glu Ala Gly Gly Pro Ser Glu Ala Gly Gly Pro Ser Glu Ala

-continued

```
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Glu Ala Gly Trp Pro Ser Glu Ala
65                  70                  75                  80

Gly Trp Pro Ser Glu Ala Gly Gly Pro Ser Gly Thr Gly Trp Pro Ser
                85                  90                  95

Glu Ala Gly Trp Pro Ser Glu Ala Gly Trp Pro Ser Glu Ala Gly Trp
            100                 105                 110

Pro Ser Glu Ala Gly Trp
        115


<210> SEQ ID NO 71
<211> LENGTH: 136
<212> TYPE: PRT
<213> ORGANISM: Babesia microti

<400> SEQUENCE: 71

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Glu Ala Gly Trp Pro Ser Glu Ala
65                  70                  75                  80

Gly Trp Pro Ser Glu Ala Gly Gly Pro Ser Gly Thr Gly Trp Pro Ser
                85                  90                  95

Glu Ala Gly Trp Pro Ser Glu Ala Gly Trp Pro Ser Glu Ala Gly Trp
            100                 105                 110

Pro Ser Glu Ala Gly Trp Pro Ser Glu Arg Phe Gly Tyr Gln Leu Leu
        115                 120                 125

Trp Tyr Ser Arg Arg Ile Val Ile
    130                 135


<210> SEQ ID NO 72
<211> LENGTH: 116
<212> TYPE: PRT
<213> ORGANISM: Babesia microti

<400> SEQUENCE: 72

Glu Ala Gly Gly Pro Ser Gly Thr Val Gly Pro Ser Glu Ala Gly Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Trp Pro Ser Glu Ala Gly Trp Pro Ser Glu Ala
65                  70                  75                  80

Gly Gly Pro Ser Gly Thr Gly Trp Pro Ser Glu Ala Gly Trp Pro Ser
```

-continued

```
                85                  90                  95

Glu Ala Gly Trp Pro Ser Glu Ala Gly Trp Pro Ser Glu Ala Gly Trp
            100                 105                 110

Pro Ser Glu Arg
        115


<210> SEQ ID NO 73
<211> LENGTH: 136
<212> TYPE: PRT
<213> ORGANISM: Babesia microti

<400> SEQUENCE: 73

Gly Asp Thr Asp Arg Glu Ala Gly Gly Pro Ser Gly Thr Val Gly Pro
 1               5                  10                  15

Ser Glu Ala Gly Gly Pro Ser Glu Ala Gly Gly Pro Ser Glu Ala Gly
            20                  25                  30

Gly Pro Ser Glu Ala Gly Gly Pro Ser Glu Ala Gly Gly Pro Ser Glu
        35                  40                  45

Ala Gly Gly Pro Ser Glu Ala Gly Gly Pro Ser Glu Ala Gly Gly Pro
    50                  55                  60

Ser Glu Ala Gly Gly Pro Ser Glu Ala Gly Gly Pro Ser Glu Ala Gly
65                  70                  75                  80

Trp Pro Ser Glu Ala Gly Trp Pro Ser Glu Ala Gly Gly Pro Ser Gly
                85                  90                  95

Thr Gly Trp Pro Ser Glu Ala Gly Trp Pro Ser Glu Ala Gly Trp Pro
            100                 105                 110

Ser Glu Ala Gly Trp Pro Ser Glu Ala Gly Trp Pro Ser Glu Arg Phe
        115                 120                 125

Gly Tyr Gln Leu Leu Trp Tyr Ser
    130                 135


<210> SEQ ID NO 74
<211> LENGTH: 138
<212> TYPE: PRT
<213> ORGANISM: Babesia microti

<400> SEQUENCE: 74

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Glu Ala Gly Gly Pro Ser Glu Ala
65                  70                  75                  80

Gly Gly Pro Ser Glu Ala Gly Trp Pro Ser Glu Ala Gly Trp Pro Ser
                85                  90                  95

Glu Ala Gly Gly Pro Ser Gly Thr Gly Trp Pro Ser Glu Ala Gly Trp
            100                 105                 110

Pro Ser Glu Ala Gly Trp Pro Ser Glu Ala Gly Trp Pro Ser Glu Ala
        115                 120                 125

Gly Trp Pro Ser Glu Arg Phe Gly Tyr Gln
    130                 135
```

-continued

<210> SEQ ID NO 75
<211> LENGTH: 118
<212> TYPE: PRT
<213> ORGANISM: Babesia microti

<400> SEQUENCE: 75

```
Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Gly Thr Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Arg Phe Gly Tyr Gln Leu Leu Trp Tyr
            100                 105                 110

Ser Arg Arg Ile Val Ile
        115
```

<210> SEQ ID NO 76
<211> LENGTH: 94
<212> TYPE: PRT
<213> ORGANISM: Babesia microti

<400> SEQUENCE: 76

```
Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Gly Thr Gly Trp
    50                  55                  60

Pro Ser Glu Ala Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp
                85                  90
```

<210> SEQ ID NO 77
<211> LENGTH: 113
<212> TYPE: PRT
<213> ORGANISM: Babesia microti

<400> SEQUENCE: 77

```
Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Gly Thr Gly Trp Pro Ser Glu Ala Gly Trp Pro Ser Glu Ala
65                  70                  75                  80
```

-continued

```
Gly Trp Pro Ser Glu Ala Gly Trp Pro Ser Glu Ala Gly Trp Pro Ser
                85                  90                  95

Glu Ala Gly Trp Pro Ser Glu Arg Phe Gly Tyr Gln Leu Leu Trp Tyr
            100                 105                 110

Ser


<210> SEQ ID NO 78
<211> LENGTH: 120
<212> TYPE: PRT
<213> ORGANISM: Babesia microti

<400> SEQUENCE: 78

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Gly Thr Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Ala Gly Trp Pro Ser Glu Arg Phe Gly
            100                 105                 110

Tyr Gln Leu Leu Trp Tyr Ser Arg
        115                 120


<210> SEQ ID NO 79
<211> LENGTH: 120
<212> TYPE: PRT
<213> ORGANISM: Babesia microti

<400> SEQUENCE: 79

Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Gly Thr Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Ala Gly Trp Pro Ser Glu Arg Phe Gly
            100                 105                 110

Tyr Gln Leu Leu Trp Tyr Ser Arg
        115                 120


<210> SEQ ID NO 80
<211> LENGTH: 29
<212> TYPE: DNA
<213> ORGANISM: Artificial Sequence
<220> FEATURE:
```

-continued

<223> OTHER INFORMATION: PCR Primer

<400> SEQUENCE: 80
cagagcagta ctgatgatat taagaaggc 29

<210> SEQ ID NO 81
<211> LENGTH: 43
<212> TYPE: DNA
<213> ORGANISM: Artificial Sequence
<220> FEATURE:
<223> OTHER INFORMATION: PCR Primer

<400> SEQUENCE: 81
caatatgaat tcagtgaata tttacaataa atgttaataa tgc 43

<210> SEQ ID NO 82
<211> LENGTH: 32
<212> TYPE: DNA
<213> ORGANISM: Artificial Sequence
<220> FEATURE:
<223> OTHER INFORMATION: PCR Primer

<400> SEQUENCE: 82
cataacaata ttccagaacc caatgcggat tc 32

<210> SEQ ID NO 83
<211> LENGTH: 32
<212> TYPE: DNA
<213> ORGANISM: Artificial Sequence
<220> FEATURE:
<223> OTHER INFORMATION: PCR Primer

<400> SEQUENCE: 83
cgctagaatt cattagaaag ccttaaacat gc 32

<210> SEQ ID NO 84
<211> LENGTH: 2001
<212> TYPE: DNA
<213> ORGANISM: Babesia

<400> SEQUENCE: 84
atgcagcatc accaccatca ccacactgat gatattaaga aggcatttga cgaatgcaaa 60
tctaatgcta ttatattgaa gaaaaagata cttgacaatg atgaagatta taagattaat 120
tttagggaaa tggtgaatga agtaacatgt gcaaacacaa aatttgaagc cctaaatgat 180
ttgataattt ccgactgtga gaaaaaaggt attaagataa acagagatgt gatttcaagc 240
tacaaattgc ttctttccac aatcacctat attgttggag ctggagttga agctgtaact 300
gttagtgtgt ctgctacatc taatggaact gaatctggtg gagctggtag tggaactgga 360
actagtgtgt ctgctacatc tactttaact ggtaatggtg gaactgaatc tggtggaaca 420
gctggaacta ctacgtctag tggaactgaa gctggtggaa ctagtggaac tactacgtct 480
agtggagctg ctagtggtaa agctggaact ggaacagctg gaactactac gtctagtgaa 540
ggtgctggta gtgataaagc tggaactgga actagtggaa ctactacgtc tagtggaact 600
ggtgctggtg gagctggtag tggtggacct agtggacatg cttctaatgc aaaaaattcct 660 ggaataatga cactaactct atttgcatta ttaacattta ttgtaaatat tccagaaccc 720
aatgcggatt cagaatctgt acatgttgaa atccaggaac atgataacat caatccacaa 780
gacgcttgcg atagtgagcc gctcgaacaa atggattctg ataccagggt gttgcccgaa 840
agtttggatg agggggtacc acaccaattc tctagattag ggcaccactc agacatggca 900

-continued

```
tctgatataa atgatgaaga accatcattt aaaatcggcg agaatgacat aattcaacca    960

ccctgggaag atacagctcc ataccattca atagatgatg aagagcttga caacttaatg   1020

agactaacgg cgcaagaaac aagtgacgat catgaagaag ggaatggcaa actcaatacg   1080

aataaaagtg agaagactga aagaaaatcg catgatactc agacaccgca agaaatatat   1140

gaagagcttg acaacttact gagactaacg gcacaagaaa tatatgaaga gcgtaaagaa   1200

gggcatggca aacccaatac gaataaaagt gagaaggctg aaagaaaatc gcatgatact   1260

cagacaacgc aagaaatatg tgaagagtgt gaagaagggc atgacaaaat caataagaat   1320

aaaagtggaa atgctggaat aaaatcgtat gatactcaga caacgcaaga aatatgtgaa   1380

gagtgtgaag aagggcatga caaaatcaat aagaataaaa gtggaaatgc tggaataaaa   1440

tcgtatgata ctcagacacc gcaggaaaca agtgacgctc atgaagaagg gcatgacaaa   1500

atcaatacga ataaaagtga gaaggctgaa agaaaatcgc atgatactca gacaacgcaa   1560

gaaatatgtg aagagtgtga agaagggcat gacaaaatca ataagaataa aagtggaaat   1620

gctggaataa aatcgtatga tactcagaca ccgcaggaaa caagtgacgc tcatgaagaa   1680

gagcatggca atctcaataa gaataaaagt gggaaggctg gaataaaatc gcataatact   1740

cagacaccgc tgaaaaaaaa agacttttgt aaagaagggt gtcatggttg caataataag   1800

cccgaggata atgaaagaga cccgtcgtcg cctgatgatg atggtggctg cgaatgcggc   1860

atgacgaatc actttgtctt tgactacaag acaacactct tgttaaagag cctcaagact   1920

gaaacatcca ctcattatta cattgccatg gctgcaattt ttactatttc attattccca   1980

tgcatgttta aggctttctg a                                             2001
```

```
<210> SEQ ID NO 85
<211> LENGTH: 666
<212> TYPE: PRT
<213> ORGANISM: Babesia

<400> SEQUENCE: 85

Met Gln His His His His His His Thr Asp Asp Ile Lys Lys Ala Phe
                5                   10                  15

Asp Glu Cys Lys Ser Asn Ala Ile Ile Leu Lys Lys Lys Ile Leu Asp
            20                  25                  30

Asn Asp Glu Asp Tyr Lys Ile Asn Phe Arg Glu Met Val Asn Glu Val
        35                  40                  45

Thr Cys Ala Asn Thr Lys Phe Glu Ala Leu Asn Asp Leu Ile Ile Ser
    50                  55                  60

Asp Cys Glu Lys Lys Gly Ile Lys Ile Asn Arg Asp Val Ile Ser Ser
 65                 70                  75                  80

Tyr Lys Leu Leu Leu Ser Thr Ile Thr Tyr Ile Val Gly Ala Gly Val
                85                  90                  95

Glu Ala Val Thr Val Ser Val Ser Ala Thr Ser Asn Gly Thr Glu Ser
            100                 105                 110

Gly Gly Ala Gly Ser Gly Thr Gly Thr Ser Val Ser Ala Thr Ser Thr
        115                 120                 125

Leu Thr Gly Asn Gly Gly Thr Glu Ser Gly Gly Thr Ala Gly Thr Thr
    130                 135                 140

Thr Ser Ser Gly Thr Glu Ala Gly Gly Thr Ser Gly Thr Thr Thr Ser
145                 150                 155                 160

Ser Gly Ala Ala Ser Gly Lys Ala Gly Thr Gly Thr Ala Gly Thr Thr
                165                 170                 175
```

-continued

```
Thr Ser Ser Glu Gly Ala Gly Ser Asp Lys Ala Gly Thr Gly Thr Ser
            180                 185                 190

Gly Thr Thr Thr Ser Ser Gly Thr Gly Ala Gly Gly Ala Gly Ser Gly
        195                 200                 205

Gly Pro Ser Gly His Ala Ser Asn Ala Lys Ile Pro Gly Ile Met Thr
    210                 215                 220

Leu Thr Leu Phe Ala Leu Leu Thr Phe Ile Val Asn Ile Pro Glu Pro
225                 230                 235                 240

Asn Ala Asp Ser Glu Ser Val His Val Glu Ile Gln Glu His Asp Asn
                245                 250                 255

Ile Asn Pro Gln Asp Ala Cys Asp Ser Glu Pro Leu Glu Gln Met Asp
            260                 265                 270

Ser Asp Thr Arg Val Leu Pro Glu Ser Leu Asp Glu Gly Val Pro His
        275                 280                 285

Gln Phe Ser Arg Leu Gly His His Ser Asp Met Ala Ser Asp Ile Asn
    290                 295                 300

Asp Glu Glu Pro Ser Phe Lys Ile Gly Glu Asn Asp Ile Ile Gln Pro
305                 310                 315                 320

Pro Trp Glu Asp Thr Ala Pro Tyr His Ser Ile Asp Asp Glu Glu Leu
                325                 330                 335

Asp Asn Leu Met Arg Leu Thr Ala Gln Glu Thr Ser Asp Asp His Glu
            340                 345                 350

Glu Gly Asn Gly Lys Leu Asn Thr Asn Lys Ser Glu Lys Thr Glu Arg
        355                 360                 365

Lys Ser His Asp Thr Gln Thr Pro Gln Glu Ile Tyr Glu Glu Leu Asp
    370                 375                 380

Asn Leu Leu Arg Leu Thr Ala Gln Glu Ile Tyr Glu Glu Arg Lys Glu
385                 390                 395                 400

Gly His Gly Lys Pro Asn Thr Asn Lys Ser Glu Lys Ala Glu Arg Lys
                405                 410                 415

Ser His Asp Thr Gln Thr Thr Gln Glu Ile Cys Glu Glu Cys Glu Glu
            420                 425                 430

Gly His Asp Lys Ile Asn Lys Asn Lys Ser Gly Asn Ala Gly Ile Lys
        435                 440                 445

Ser Tyr Asp Thr Gln Thr Thr Gln Glu Ile Cys Glu Glu Cys Glu Glu
    450                 455                 460

Gly His Asp Lys Ile Asn Lys Asn Lys Ser Gly Asn Ala Gly Ile Lys
465                 470                 475                 480

Ser Tyr Asp Thr Gln Thr Pro Gln Glu Thr Ser Asp Ala His Glu Glu
                485                 490                 495

Gly His Asp Lys Ile Asn Thr Asn Lys Ser Glu Lys Ala Glu Arg Lys
            500                 505                 510

Ser His Asp Thr Gln Thr Thr Gln Glu Ile Cys Glu Glu Cys Glu Glu
        515                 520                 525

Gly His Asp Lys Ile Asn Lys Asn Lys Ser Gly Asn Ala Gly Ile Lys
    530                 535                 540

Ser Tyr Asp Thr Gln Thr Pro Gln Glu Thr Ser Asp Ala His Glu Glu
545                 550                 555                 560

Glu His Gly Asn Leu Asn Lys Asn Lys Ser Gly Lys Ala Gly Ile Lys
                565                 570                 575

Ser His Asn Thr Gln Thr Pro Leu Lys Lys Lys Asp Phe Cys Lys Glu
            580                 585                 590
```

-continued

Gly Cys His Gly Cys Asn Asn Lys Pro Glu Asp Asn Glu Arg Asp Pro
595 600 605

Ser Ser Pro Asp Asp Asp Gly Gly Cys Glu Cys Gly Met Thr Asn His
610 615 620

Phe Val Phe Asp Tyr Lys Thr Thr Leu Leu Leu Lys Ser Leu Lys Thr
625 630 635 640

Glu Thr Ser Thr His Tyr Tyr Ile Ala Met Ala Ala Ile Phe Thr Ile
645 650 655

Ser Leu Phe Pro Cys Met Phe Lys Ala Phe
660 665

<210> SEQ ID NO 86
<211> LENGTH: 3402
<212> TYPE: DNA
<213> ORGANISM: Babesia

<400> SEQUENCE: 86
atgcagcatc accaccatca ccacttgact tttggaaata tacgttttca taatataaat 60
ctcccaccat tttcattggg cataattcac tcgattacgg tagaaaaggc gattaactct 120
gaagattttg acggaataca aacactttta caagtgtcta tcattgctag ttacggtcca 180
tctggcgatt acagtagttt tgtgttcact ccagttgtaa cagcagacac caacgttttt 240
tacaaattag agacggattt caaacttgat gttgatgtta ttactaagac atcactagaa 300
ttgcccacaa gtgttcctgg ctttcactac accgaaacta tttaccaagg cacagaattg 360
tcaaaattta gcaagcctca gtgcaaactt aacgatcctc ctattacaac aggatcgggg 420
ttgcaaataa tacatgatgg tttgaataat tcgacaatta taaccaacaa agaagttaat 480
gtggatggaa cagatttagt tttttttgaa ttgctccctc catcggatgg cattcccacc 540
ttgcgatcaa aattatttcc cgtcctgaaa tcaattccaa tgatatctac cggggttaat 600
gaattactgt tggaagtact cgagaacccc tctttcccta gtgcaattag caattacacc 660
ggactgacag gccgacttaa caaattactt acagttttag acggtattgt tgatagcgcc 720
attagtgtca agactacaga aactgtccct gacgacgcag aaacttctat ttcttcattg 780
aaatcattga taaaggcaat acgagataat attactacca ctcgaaacga agttaccaaa 840
gatgatgttt atgcattgaa gaaggccctc acttgtctaa cgacacacct aatatatcat 900
tcaaaagtag atggtatatc attcgacatg ctgggaacac aaaaaaataa atctagccca 960
ctaggcaaga tcggaacgtc tatggacgat attatagcca tgttttcgaa tcccaatatg 1020
tatcttgtga aggtggcgta cttgcaagcc attgaacaca tttttctcat atcaaccaaa 1080
tacaatgata tatttgatta caccattgat tttagtaagc gtgaagctac tgattctgga 1140
tcatttaccg atatattgct cggaaacaag gtgaaggaat ctttgtcatt tattgagggt 1200
ttgatttctg acataaaatc tcactcattg aaagctgggg ttacaggagg tatatcaagt 1260
tcatcattat ttgatgaaat cttcgacgag ttaaatttgg atcaagcaac aattagaacc 1320
cttgttgcac cattagattg gccacttatc tcagacaaaa gcctccaccc ttcactgaag 1380
atggttgtgg tcctgccagg atttttcata gttcctggat ccactgatga tattaagaag 1440
gcatttgacg aatgcaaatc taatgctatt atattgaaga aaaagatact tgacaatgat 1500
gaagattata agattaattt tagggaaatg gtgaatgaag taacatgtgc aaacacaaaa 1560
tttgaagccc taaatgattt gataatttcc gactgtgaga aaaaaggtat taagataaac 1620
agagatgtga tttcaagcta caaattgctt ctttccacaa tcacctatat tgttggagct 1680

-continued

```
ggagttgaag ctgtaactgt tagtgtgtct gctacatcta atggaactga atctggtgga   1740

gctggtagtg gaactggaac tagtgtgtct gctacatcta ctttaactgg taatggtgga   1800

actgaatctg gtggaacagc tggaactact acgtctagtg gaactgaagc tggtggaact   1860

agtggaacta ctacgtctag tggagctgct agtggtaaag ctggaactgg aacagctgga   1920

actactacgt ctagtgaagg tgctggtagt gataaagctg gaactggaac tagtggaact   1980

actacgtcta gtggaactgg tgctggtgga gctggtagtg gtggacctag tggacatgct   2040

tctaatgcaa aaattcctgg aataatgaca ctaactctat ttgcattatt aacatttatt   2100

gtaaatattc cagaacccaa tgcggattca gaatctgtac atgttgaaat ccaggaacat   2160

gataacatca atccacaaga cgcttgcgat agtgagccgc tcgaacaaat ggattctgat   2220

accagggtgt tgcccgaaag tttggatgag ggggtaccac accaattctc tagattaggg   2280

caccactcag acatggcatc tgatataaat gatgaagaac catcatttaa aatcggcgag   2340

aatgacataa ttcaaccacc ctgggaagat acagctccat accattcaat agatgatgaa   2400

gagcttgaca acttaatgag actaacggcg caagaaacaa gtgacgatca tgaagaaggg   2460

aatggcaaac tcaatacgaa taaaagtgag aagactgaaa gaaaatcgca tgatactcag   2520

acaccgcaag aaatatatga agagcttgac aacttactga gactaacggc acaagaaata   2580

tatgaagagc gtaaagaagg gcatggcaaa cccaatacga ataaaagtga gaaggctgaa   2640

agaaaatcgc atgatactca gacaacgcaa gaaatatgtg aagagtgtga agaagggcat   2700

gacaaaatca ataagaataa aagtggaaat gctggaataa aatcgtatga tactcagaca   2760

acgcaagaaa tatgtgaaga gtgtgaagaa gggcatgaca aaatcaataa gaataaaagt   2820

ggaaatgctg gaataaaatc gtatgatact cagacaccgc aggaaacaag tgacgctcat   2880

gaagaagggc atgacaaaat caatacgaat aaaagtgaga aggctgaaag aaaatcgcat   2940

gatactcaga caacgcaaga aatatgtgaa gagtgtgaag aagggcatga caaaatcaat   3000

aagaataaaa gtggaaatgc tggaataaaa tcgtatgata ctcagacacc gcaggaaaca   3060

agtgacgctc atgaagaaga gcatggcaat ctcaataaga ataaaagtgg gaaggctgga   3120

ataaaatcgc ataatactca gacaccgctg aaaaaaaaag acttttgtaa agaagggtgt   3180

catggttgca ataataagcc cgaggataat gaaagagacc cgtcgtcgcc tgatgatgat   3240

ggtggctgcg aatgcggcat gacgaatcac tttgtctttg actacaagac aacactcttg   3300

ttaaagagcc tcaagactga aacatccact cattattaca ttgccatggc tgcaattttt   3360

actatttcat tattcccatg catgtttaag gctttctaat ga                      3402
```

<210> SEQ ID NO 87
<211> LENGTH: 1132
<212> TYPE: PRT
<213> ORGANISM: Babesia

<400> SEQUENCE: 87

```
Met Gln His His His His His His Leu Thr Phe Gly Asn Ile Arg Phe
                5                   10                  15

His Asn Ile Asn Leu Pro Pro Phe Ser Leu Gly Ile Ile His Ser Ile
            20                  25                  30

Thr Val Glu Lys Ala Ile Asn Ser Glu Asp Phe Asp Gly Ile Gln Thr
        35                  40                  45

Leu Leu Gln Val Ser Ile Ile Ala Ser Tyr Gly Pro Ser Gly Asp Tyr
    50                  55                  60

Ser Ser Phe Val Phe Thr Pro Val Val Thr Ala Asp Thr Asn Val Phe
```

-continued

```
 65                  70                  75                  80

Tyr Lys Leu Glu Thr Asp Phe Lys Leu Asp Val Asp Val Ile Thr Lys
                 85                  90                  95

Thr Ser Leu Glu Leu Pro Thr Ser Val Pro Gly Phe His Tyr Thr Glu
            100                 105                 110

Thr Ile Tyr Gln Gly Thr Glu Leu Ser Lys Phe Ser Lys Pro Gln Cys
        115                 120                 125

Lys Leu Asn Asp Pro Pro Ile Thr Thr Gly Ser Gly Leu Gln Ile Ile
    130                 135                 140

His Asp Gly Leu Asn Asn Ser Thr Ile Ile Thr Asn Lys Glu Val Asn
145                 150                 155                 160

Val Asp Gly Thr Asp Leu Val Phe Phe Glu Leu Leu Pro Pro Ser Asp
                165                 170                 175

Gly Ile Pro Thr Leu Arg Ser Lys Leu Phe Pro Val Leu Lys Ser Ile
            180                 185                 190

Pro Met Ile Ser Thr Gly Val Asn Glu Leu Leu Leu Glu Val Leu Glu
        195                 200                 205

Asn Pro Ser Phe Pro Ser Ala Ile Ser Asn Tyr Thr Gly Leu Thr Gly
    210                 215                 220

Arg Leu Asn Lys Leu Leu Thr Val Leu Asp Gly Ile Val Asp Ser Ala
225                 230                 235                 240

Ile Ser Val Lys Thr Thr Glu Thr Val Pro Asp Asp Ala Glu Thr Ser
                245                 250                 255

Ile Ser Ser Leu Lys Ser Leu Ile Lys Ala Ile Arg Asp Asn Ile Thr
            260                 265                 270

Thr Thr Arg Asn Glu Val Thr Lys Asp Asp Val Tyr Ala Leu Lys Lys
        275                 280                 285

Ala Leu Thr Cys Leu Thr Thr His Leu Ile Tyr His Ser Lys Val Asp
    290                 295                 300

Gly Ile Ser Phe Asp Met Leu Gly Thr Gln Lys Asn Lys Ser Ser Pro
305                 310                 315                 320

Leu Gly Lys Ile Gly Thr Ser Met Asp Asp Ile Ile Ala Met Phe Ser
                325                 330                 335

Asn Pro Asn Met Tyr Leu Val Lys Val Ala Tyr Leu Gln Ala Ile Glu
            340                 345                 350

His Ile Phe Leu Ile Ser Thr Lys Tyr Asn Asp Ile Phe Asp Tyr Thr
        355                 360                 365

Ile Asp Phe Ser Lys Arg Glu Ala Thr Asp Ser Gly Ser Phe Thr Asp
    370                 375                 380

Ile Leu Leu Gly Asn Lys Val Lys Glu Ser Leu Ser Phe Ile Glu Gly
385                 390                 395                 400

Leu Ile Ser Asp Ile Lys Ser His Ser Leu Lys Ala Gly Val Thr Gly
                405                 410                 415

Gly Ile Ser Ser Ser Ser Leu Phe Asp Glu Ile Phe Asp Glu Leu Asn
            420                 425                 430

Leu Asp Gln Ala Thr Ile Arg Thr Leu Val Ala Pro Leu Asp Trp Pro
        435                 440                 445

Leu Ile Ser Asp Lys Ser Leu His Pro Ser Leu Lys Met Val Val Val
    450                 455                 460

Leu Pro Gly Phe Phe Ile Val Pro Gly Ser Thr Asp Asp Ile Lys Lys
465                 470                 475                 480

Ala Phe Asp Glu Cys Lys Ser Asn Ala Ile Ile Leu Lys Lys Lys Ile
                485                 490                 495
```

-continued

```
Leu Asp Asn Asp Glu Asp Tyr Lys Ile Asn Phe Arg Glu Met Val Asn
            500                 505                 510

Glu Val Thr Cys Ala Asn Thr Lys Phe Glu Ala Leu Asn Asp Leu Ile
        515                 520                 525

Ile Ser Asp Cys Glu Lys Lys Gly Ile Lys Ile Asn Arg Asp Val Ile
    530                 535                 540

Ser Ser Tyr Lys Leu Leu Leu Ser Thr Ile Thr Tyr Ile Val Gly Ala
545                 550                 555                 560

Gly Val Glu Ala Val Thr Val Ser Val Ser Ala Thr Ser Asn Gly Thr
                565                 570                 575

Glu Ser Gly Gly Ala Gly Ser Gly Thr Gly Thr Ser Val Ser Ala Thr
            580                 585                 590

Ser Thr Leu Thr Gly Asn Gly Gly Thr Glu Ser Gly Gly Thr Ala Gly
        595                 600                 605

Thr Thr Thr Ser Ser Gly Thr Glu Ala Gly Gly Thr Ser Gly Thr Thr
    610                 615                 620

Thr Ser Ser Gly Ala Ala Ser Gly Lys Ala Gly Thr Gly Thr Ala Gly
625                 630                 635                 640

Thr Thr Thr Ser Ser Glu Gly Ala Gly Ser Asp Lys Ala Gly Thr Gly
                645                 650                 655

Thr Ser Gly Thr Thr Thr Ser Ser Gly Thr Gly Ala Gly Gly Ala Gly
            660                 665                 670

Ser Gly Gly Pro Ser Gly His Ala Ser Asn Ala Lys Ile Pro Gly Ile
        675                 680                 685

Met Thr Leu Thr Leu Phe Ala Leu Leu Thr Phe Ile Val Asn Ile Pro
    690                 695                 700

Glu Pro Asn Ala Asp Ser Glu Ser Val His Val Glu Ile Gln Glu His
705                 710                 715                 720

Asp Asn Ile Asn Pro Gln Asp Ala Cys Asp Ser Glu Pro Leu Glu Gln
                725                 730                 735

Met Asp Ser Asp Thr Arg Val Leu Pro Glu Ser Leu Asp Glu Gly Val
            740                 745                 750

Pro His Gln Phe Ser Arg Leu Gly His His Ser Asp Met Ala Ser Asp
        755                 760                 765

Ile Asn Asp Glu Glu Pro Ser Phe Lys Ile Gly Glu Asn Asp Ile Ile
    770                 775                 780

Gln Pro Pro Trp Glu Asp Thr Ala Pro Tyr His Ser Ile Asp Asp Glu
785                 790                 795                 800

Glu Leu Asp Asn Leu Met Arg Leu Thr Ala Gln Glu Thr Ser Asp Asp
                805                 810                 815

His Glu Glu Gly Asn Gly Lys Leu Asn Thr Asn Lys Ser Glu Lys Thr
            820                 825                 830

Glu Arg Lys Ser His Asp Thr Gln Thr Pro Gln Glu Ile Tyr Glu Glu
        835                 840                 845

Leu Asp Asn Leu Leu Arg Leu Thr Ala Gln Glu Ile Tyr Glu Glu Arg
    850                 855                 860

Lys Glu Gly His Gly Lys Pro Asn Thr Asn Lys Ser Glu Lys Ala Glu
865                 870                 875                 880

Arg Lys Ser His Asp Thr Gln Thr Thr Gln Glu Ile Cys Glu Glu Cys
                885                 890                 895

Glu Glu Gly His Asp Lys Ile Asn Lys Asn Lys Ser Gly Asn Ala Gly
            900                 905                 910
```

-continued

```
Ile Lys Ser Tyr Asp Thr Gln Thr Thr Gln Glu Ile Cys Glu Glu Cys
        915                 920                 925

Glu Glu Gly His Asp Lys Ile Asn Lys Asn Lys Ser Gly Asn Ala Gly
    930                 935                 940

Ile Lys Ser Tyr Asp Thr Gln Thr Pro Gln Glu Thr Ser Asp Ala His
945                 950                 955                 960

Glu Glu Gly His Asp Lys Ile Asn Thr Asn Lys Ser Glu Lys Ala Glu
                965                 970                 975

Arg Lys Ser His Asp Thr Gln Thr Thr Gln Glu Ile Cys Glu Glu Cys
            980                 985                 990

Glu Glu Gly His Asp Lys Ile Asn Lys Asn Lys Ser Gly Asn Ala Gly
        995                 1000                1005

Ile Lys Ser Tyr Asp Thr Gln Thr Pro Gln Glu Thr Ser Asp Ala His
    1010                1015                1020

Glu Glu Glu His Gly Asn Leu Asn Lys Asn Lys Ser Gly Lys Ala Gly
1025                1030                1035                1040

Ile Lys Ser His Asn Thr Gln Thr Pro Leu Lys Lys Lys Asp Phe Cys
                1045                1050                1055

Lys Glu Gly Cys His Gly Cys Asn Asn Lys Pro Glu Asp Asn Glu Arg
            1060                1065                1070

Asp Pro Ser Ser Pro Asp Asp Asp Gly Gly Cys Glu Cys Gly Met Thr
        1075                1080                1085

Asn His Phe Val Phe Asp Tyr Lys Thr Thr Leu Leu Leu Lys Ser Leu
    1090                1095                1100

Lys Thr Glu Thr Ser Thr His Tyr Tyr Ile Ala Met Ala Ala Ile Phe
1105                1110                1115                1120

Thr Ile Ser Leu Phe Pro Cys Met Phe Lys Ala Phe
                1125                1130
```

<210> SEQ ID NO 88
<211> LENGTH: 29
<212> TYPE: DNA
<213> ORGANISM: Artificial Sequence
<220> FEATURE:
<223> OTHER INFORMATION: PCR Primer

<400> SEQUENCE: 88
ccgtcgcagc tgacttttgg aaatatacg 29

<210> SEQ ID NO 89
<211> LENGTH: 36
<212> TYPE: DNA
<213> ORGANISM: Artificial Sequence
<220> FEATURE:
<223> OTHER INFORMATION: PCR Primer

<400> SEQUENCE: 89
ctagaattca taggatccag gaactatgaa aaatcc 36

<210> SEQ ID NO 90
<211> LENGTH: 27
<212> TYPE: DNA
<213> ORGANISM: Artificial Sequence
<220> FEATURE:
<223> OTHER INFORMATION: PCR Primer

<400> SEQUENCE: 90
cgtggatcca ctgatgatat taagaag 27

-continued

<210> SEQ ID NO 91
<211> LENGTH: 1148
<212> TYPE: DNA
<213> ORGANISM: Babesia microti

<400> SEQUENCE: 91
tgactggata tcgccaattg tattgtaaca ggtggttgct atggaaatat taccaagctg 60
cagcgcttta tcgccgagtc tcttccacct ttcaatattt atgggttcaa tttgcatttt 120
agacgcggat tttctgggcg agtttacctc agatgaatta tttggtgatt tcaaggcacc 180
tttataaaat gtctcataag aatcaccatt caattgttcc agacactaaa tatttgtcaa 240
cttactaact caacatcacc ggtgctcaaa gccaattcaa atttccttga tgcatttacc 300
gttatggcaa ctgctagctg tatattaccc atagcttcaa ctattacgct tatcctttcc 360
cgtaaatggg ttggtatttc agcaaccata tcaagtacta atccccaatt attctccaac 420
attgcagtct aaatgaattg attggattac attcaacttc aaataagttt cagttaggtt 480
gtatgacaga acatttccat ctcgatcaat aagatatatc ttgcttgttt caatggaata 540
gcccgagaat gtacagktta cgatctagat aagcgtgcgg atcaggcacg ccagttgtgt 600
acaaataaga gtctcagacc aactgktgkg taaataaatg tatcacaaac ccatactcca 660
ctcacaatac sktctgtaat ctaggttaaa caacaattta acctcagtat ccagctcaaa 720
tgttgatggt actccctcgt catcctgagg cgtattggca gcgactgata ccaaaaagga 780
attatgatca tattcttcta gttacgtttt ttctactgat ggaatcttta ccaaagttac 840
cccagctaca gggttttcaa ttggttgtgt aatatttggc aatcaattaa ttccacagtc 900
catggatgtt atcactagga ccgtttcata caccactaaa tatcctttga ttgttgttag 960
gattcaagat aagacttcga gttctacttc aaccgtttac tatgagcaat ctggtttaca 1020
atctagcaaa tttgttttga gggatgaccc agaatttatt attcctcaaa atcgaagtag 1080
tacttataca gtcaatgaca taacatataa atcatttgat atttctagtg ccgatgatac 1140
gaatttta 1148

<210> SEQ ID NO 92
<211> LENGTH: 605
<212> TYPE: DNA
<213> ORGANISM: Babesia microti
<220> FEATURE:
<221> NAME/KEY: misc_feature
<222> LOCATION: (1)...(605)
<223> OTHER INFORMATION: n=A,T,C or G

<400> SEQUENCE: 92
tggccttgcc tcaacttaat gtgccaggga ggcattagca tttctgagga gtattcactc 60
ctcagtgtgt ggtgggttga ggggaggtag ggagaaaggg agaaaggcag ggaggggaaa 120
ctctaggtgt tatgaaaagt gtatataaca ttaaaattga gggtgagaag taatgaggat 180
aaatgtaatt acccataaga acttcggtcc agcaactgaa aagtagtgga aacaactaaa 240
tgaacaaact ctgagaaaag gagaccatgt ttaataggaa ttcattccta cagaactatg 300
aaacactggt acttggtaca taagacaaac tacagaaagt aggatacgaa tgtcagagcc 360
ttctttttat tttttttctg agagatttga tcttgctcag agatgccaat tgagttctat 420
actccaataa ttgagcactt gtaccttgac ctttaatatc ctccggaaaa attatagata 480
tgagggagta taggtatgag aaaattgtct catttgtatc ctgacctccm cttgtatcct 540
gatctccact tgttgntgac ccttcacttg tttgntgacc ttcccttgtt tggtgacctt 600

-continued

```
ccttg                                                              605


<210> SEQ ID NO 93
<211> LENGTH: 631
<212> TYPE: DNA
<213> ORGANISM: Babesia microti

<400> SEQUENCE: 93

gttcctactt tgtcatcatt ggtcaagttg ttcagtgaag ttatgctgag agtgaaggat     60

gcgtcttcca cagaggctac catacgcatg ttcctccgtt tcaacgcatt tataaaattt    120

ttgaatgagg agaaatccag aggtgacaaa agtgcgttga atgatgaggg attgatgagg    180

tttatatcga tgaccagtgg atttatcgat gaccttgaat tagttttaga tgagttatcc    240

aagcacagtt tgcttataaa taacgaaggt gccaagagca tgctatcctc tctcatacta    300

agcttccgtt atattaatca cataagaaat ttgatcaatg gtatttacct tggattgaat    360

aacccatcat cgtccattgg tgagacagca caagaaacaa ctgaaccctc cactcccact    420

cccactccca gcacacagac aatcctgaaa ccgaagggat ccgagataag ggctatata    480

ataaaagttg atcaaacagc taatctcatc acattcatag atgcattgat caaggagttg    540

aacgttcata ttaaacagac aacaacttcg tctggtkgtt ggcactaaag aaactaatgg    600

cactaccagt ggttctyctg aaagcaatcc c                                   631


<210> SEQ ID NO 94
<211> LENGTH: 632
<212> TYPE: DNA
<213> ORGANISM: Babesia microti
<220> FEATURE:
<221> NAME/KEY: misc_feature
<222> LOCATION: (1)...(632)
<223> OTHER INFORMATION: n=A,T,C or G

<400> SEQUENCE: 94

ataaataagt aaatacttac tgaaaacact tcaaaaacat gcaaaaacac agcataggac     60

ttaacaatta caaagtgaaa ctgtacaatt ccatccttct aatgccattt acaagttgag    120

aatttaggaa atataaatca taagcagata gatcaaaaac agaatatctg gaataatgaa    180

acataaaatg gaaatctaaa ctagaagtaa gttttataaa gccacaggca ggtactgaac    240

ctgagttcct ggttaccgac tgttagtctt cccttaatgg ggtagacttg gctggcccca    300

aagccactgg tatcatcatt ctgtctttgc atgtcctgtg caagggctca aggtgtgctg    360

ctgtgtccag tttgctacaa gagtactgag gctgagccca tatccccatg gttatatggt    420

gaacaatttc cacatggagc attctcccca gttcatcttc cagaattcaa tattgatgta    480

tcagttctta attcattgat gtaagtcaat ctcccttaaa ttaaaaatta atagaaagca    540

atttctctaa cgggcaactt tctgcttgcg tgtaatatgt atgtgaaatc tagattctgc    600

ngaggagacc aaaccagtnt atttttgtgc ct                                  632


<210> SEQ ID NO 95
<211> LENGTH: 426
<212> TYPE: DNA
<213> ORGANISM: Babesia microti
<220> FEATURE:
<221> NAME/KEY: misc_feature
<222> LOCATION: (1)...(426)
<223> OTHER INFORMATION: n=A,T,C or G

<400> SEQUENCE: 95

attttgtact gttcaaatgt gtaatatatt tgtgaaagaa gaaaataatt taagtcaaga     60
```

-continued

```
ggatgatgaa agggcagaag taatacttga gataagcact tcacatctta caattaaaac    120

tcttctgtgt ctacctgcaa attcatgaca gatgaaatta acttgntttc tattcggttt    180

ctcctcttat ttctgccagt attataattt caggaaggaa catgcatcat aaattacatg    240

taactttcat gttgcagtga tgctggtttc tatttttgat ctcatttgac agcagtaaag    300

tcatacnaaa aataataaat acctctcatg gagcttgcca tttcctctgc atcttttttg    360

gggaagaant ggcctgaaaa gtaaagcgtt aagactcaca aagtcaaaaa ctttcagata    420

gaaccc                                                               426


<210> SEQ ID NO 96
<211> LENGTH: 472
<212> TYPE: DNA
<213> ORGANISM: Babesia microti
<220> FEATURE:
<221> NAME/KEY: misc_feature
<222> LOCATION: (1)...(472)
<223> OTHER INFORMATION: n=A,T,C or G

<400> SEQUENCE: 96

aggtnacaca tagaggagtg tggtcaatta aacactcaag caccctatgt cttggtttgc     60

tctctattgc tgtgataaac accagagcta agcccaactt gaagttgtca catggtctcc    120

acacaaatac acacacacac acaccacaca cacacctatt gtatgcacat gcaccccccc    180

ccccttncaa aaaaaaagga ncctctactc tttaccagca ataaaaaatg aactaggtga    240

aaagaaaacc aaccttgctt catcatttag tcatagaaaa tgatactggg gttggcattt    300

actatcatta acctaaaata aatgtgtccc tacctaaggg tataaactgt tatctggcct    360

tgtacagatt ttggatcttg aattctttta gngggttgcc caatagcatt ttaaggnccc    420

agaataaata gaccggatga aatgggatgg gctagagtag aatggaggct an            472


<210> SEQ ID NO 97
<211> LENGTH: 867
<212> TYPE: DNA
<213> ORGANISM: Babesia microti
<220> FEATURE:
<221> NAME/KEY: misc_feature
<222> LOCATION: (1)...(867)
<223> OTHER INFORMATION: n=A,T,C or G

<400> SEQUENCE: 97

ttaatattat gttcaccgaa acatcctgta gtatacaact caaccaattc accattaaat     60

gataatttga tcagtgtata ttgtgatgtt atatttattg gtattgttat ctcaccaacc    120

ttaacttcgc tgatgtaaat tttggaatct ggattattgg tgtacaacat gctcccatca    180

cttaatgata tttttaaaaa ttcgttatca tcggcactag aaatatcaaa tgatttatat    240

gttatgtcat tgactgtata agtactactt cgattttgag gaataataaa ttctgggtca    300

tccctcaaaa caaatttgct agattgnaaa ccagattgct catagtaaac gggtgaagta    360

gaactcgaag tcttatcttg aatcctaaca acmatcaaag gatatttagt ggtgtatgaa    420

acggtcctag tgataacaty catggactgt ggaattaatt gattgccaaa tattacacaa    480

ccaattgaaa accctgtagc tggggtaact ttggtaaaga ttccatcagt agaaaaaacg    540

taactagaag aaagaccctc tggaacttga tcaacaaatc ctatttcgtt tatgttaaga    600

ttcacaatat ttgtgacagc aacatcttgt gtggtctcca gagacggaga aattgttgat    660

gtggcagctg ttgttgatgt ggtagctgtt gttgatgtgg cagttgttgt tgatgtggca    720
```

-continued gttgttgttg atgtggtagc tgttgttgat gtagcagatg ttgttgatgt agcagtacat 780
actgacagta catgtgcatg tgtgtgtaaa taggattctt gtaaagccaa gtatatcctc 840
actgctgatt tgtctgatat tacctcc 867

<210> SEQ ID NO 98
<211> LENGTH: 815
<212> TYPE: DNA
<213> ORGANISM: Babesia microti

<400> SEQUENCE: 98
tagtcattag attatcatga caccaataag ctttttatct tgaagttgtt ttatatatta 60
atacaaccat agcatcataa aagctacatt tgttttttttt atcttaaccc atggtcatct 120
agtctttttc ctttattatt catcattgat tgtccttaaa tgctcaaagc atctgcccct 180
ttaaactact tctttctaaa ttagcatata ctctatatgg tcatacctat tctgtgtaat 240
catcaggttc cctgtgcagg ggaaaggagg aacgctcaag cactgaggaa tcatcccgct 300
gtgtgataac gttgatggaa gacaagtgat acagttagtt gttcaaacaa ataagcatat 360
tttaagggga agaatagtgt cgtactaact aaaatctaat ttgaccataa tacgcacatt 420
agtttgtttg tgctcaattt ttttaatgaa tcaggccccc gatttatatt tgtgaaagtc 480
catgtgggag cgtaaggatg ggatagttta tttacagtag cttctctggg gaaaggaaag 540
caaagcccca actgtataga gttcattgga gctgtcacct acgcccctgc cttcctgtcc 600
ctttagagtg cctcagtttg ctgtgtggca agagtctctc cctgctcctg ctctcctagc 660
cccctctgcc tgcctccccc agttgatgcg agagtccact gttggagaag ttaactctaa 720
tcttacacct ggggagagct actggaaatt aattttccat gtaactggct ttgagttcta 780
gcaggcttta gattttagaa gtttttgtgt gtgtg 815

<210> SEQ ID NO 99
<211> LENGTH: 1225
<212> TYPE: DNA
<213> ORGANISM: Babesia microti
<220> FEATURE:
<221> NAME/KEY: misc_feature
<222> LOCATION: (1)...(1225)
<223> OTHER INFORMATION: n=A,T,C or G

<400> SEQUENCE: 99
attgtgtaaa gggttaccat ggccatggca atttttgtaa aagaaagcat ttaaatgggg 60
gcttgtttac agtttaagag ggttgactca tgaccatcat tgtgggaagc atggtagcag 120
gttggcatgg tgctggatca gtaattgaga gctttacact ctgatcctaa ggcatcagac 180
aaagaaaagc ctggtcctgg tgtgggcttg aagcctcaaa atccccctct aatgacacac 240
ttccctcaag tacatactta ttcctaaatc cttctcaaac agtttcaaaa cttgtgcctg 300
agtgttcaaa tatatgaacc tacaggggcc attcacattc aaattatcac aggcagataa 360
gttactagtc atggaagttc aaatatatac tttgttatga aaatataaat atgctttaga 420
atctggggaa cccagaaggg tggagatggg gtcaagattc tctgagatgg ggtcaagatt 480
ctctgtgtct ccctgggcct ggctggaatg tccctcctgt cttccaagtc ctctgttcca 540
ggtgaccatg tccccatccc agtcccctcg atggtcctca tgccctcctc tcagttcctg 600
gctgctcccc cacccccgcc acatccccat caagggactg gccggctctc atactgctac 660
ccatgcaggg tgctcatgcc cttgcgcccc ggcaccttta gtgtttcngt cccttcccgg 720
ccccactcag cgccacccca tgtcgcaggg ccgccgtccg cgccacggga ccttgcaagt 780

-continued acaagcttga gccgcttccc ccctggcgyt gcgactgcgg tggctgccgc cttgcgggam 840
tccggcggtc gttccgacgt cacctactcg stgcttgtgc ctgctctgcg ggccgcgacg 900
gtccggcggg cgcatgccaa ccctgcgggc cacgcgtggc cttcgtcccg cgtcaggcag 960
ggttgcgaga acgcgccgcc acgsttgctg cacctgcggc cgggcgcgcg ctataccgtg 1020
cgcgtggccg cgctcaacgg tgtctcaggc ccagcggccg ccgcggaagc cacctacgcg 1080
caggtcaccg tgtccaccgg acccggaggt gaggccacgc gccccagcgg agtccgtccc 1140
cctccccaac cgcagttccc tctatgcatt ccaagtcatt caggaaccca cgtgactaca 1200
ccccatgccc caggtgcggc acgag 1225

<210> SEQ ID NO 100
<211> LENGTH: 537
<212> TYPE: DNA
<213> ORGANISM: Babesia microti
<220> FEATURE:
<221> NAME/KEY: misc_feature
<222> LOCATION: (1)...(537)
<223> OTHER INFORMATION: n=A,T,C or G

<400> SEQUENCE: 100
aaagaaagag aagaagggag agaagagcaa ggggaatgaa tgagagagga gagaagggaa 60
tagaagagag gggagggcag aggaggggaa gcagagggga ggggaaagga aggagaaaga 120
gaacagagac agagggaagg tcaggtacat cactgtccaa gagatcacat attatccaag 180
cmacggacag agctttagga agtgtacaga gaggcacctt tcacccagtg tcctataatg 240
accatttctg caaattctct agaacttagt tccattctgc acaacccctc catacctgtc 300
atcatgtgct tcacttacta gcctcaagta agctgttaag tgttccagtg ttatatgcca 360
ttctagtacc ttcatccagt gactgataga agcagagcta aacncccnca gttaaacaat 420
aaactgaatc cctagaaccc mgtgaccgag agtgktctca taattcttaa aaagatgcta 480
ttaaatttta tcctgtatca tactacatta tcttttttttc ttccttcccc tcccccc 537

<210> SEQ ID NO 101
<211> LENGTH: 543
<212> TYPE: DNA
<213> ORGANISM: Babesia microti
<220> FEATURE:
<221> NAME/KEY: misc_feature
<222> LOCATION: (1)...(543)
<223> OTHER INFORMATION: n=A,T,C or G

<400> SEQUENCE: 101
acataacact agggacttgg cattgcatat ctgtaaatat aattgaaacc aaaataaaat 60
attggtgagt tccataggtt gggttgttca cagtgacatt taaaagtgaa attcttgaga 120
gctggtttgg aggttctatt aggggagtgc ggtacttgta taccttggac tgaagaccag 180
tcctcctcta ttccgggaag gycgycctct tcgaccaagc atgcacttca ggatggacac 240
acatggagtg ttgagggagg aaagagatcc ccctaagcca gatagatcaa ctaaatgaac 300
cttggaaata aatggggtga cagatgtarc avcgagaatg ccctcacata ctgaaaatga 360
aataattamc cmccwttagt ttttccatyt gatacctagg cmctytctaa tttaattcca 420
mcattctkga aaagtgkstt ttgaaagatt ggtgggcaac ccccctaatt antcccctnc 480
caatggggta aggccaaaaa accagggggg aaattccaaa aattattgnt ttgtaaaggg 540
gaa 543

-continued

<210> SEQ ID NO 102
<211> LENGTH: 811
<212> TYPE: DNA
<213> ORGANISM: Babesia microti
<220> FEATURE:
<221> NAME/KEY: misc_feature
<222> LOCATION: (1)...(811)
<223> OTHER INFORMATION: n=A,T,C or G

<400> SEQUENCE: 102
tggataagga tgaagtcagt tagaccaata ctaattcatt ttattacatt ctttttaaca 60
agtggaaatg tctttgcagg aaatggtgat gttaatcaat attcaagtga ttttggacga 120
gcattaaacg atcttatgat cgcttttaac gaggctaaaa aaatgtatgc aaaattttct 180
gaacagatca cggacactat gattcatacc tgcaaaaata gtattgatat actagaagca 240
gatgagaaga atggtggtca taaaaattac cttgaaaaga aagaaattga gctcaaaagt 300
aaaattgtgg aatttaacgc catttttttca aacattgatt taaataatan gtacggktaa 360
aaatgaaata attaaactgc ttaatgatat atccactatc tctaccgata ttaagtcaat 420
tgttgatgaa atatactata aggctcttgg tacaattgaa ggtgaaaatg ctgaaaattt 480
tgagtatgaa attaagaaaa agaaagctga actacttaga aacctgctga atgataatat 540
taaaccaatt atggggatat ttaactgaga tatcaatatg ccatccaatt atatcaaata 600
aagcgaattt atgatatcaa gaaagcattt gaaaagcacg aattagaagc taatgttttg 660
atatcccaga tattagaaaa tatcagaatt ttggcactaa ttttaatgac attttaaatg 720
aagtgaatgg ngcaattgaa gaatttaata aaactattgg acgtcatgaa taacaccatt 780
ggggaccctt ggtattggta ttgacagcgg g 811

<210> SEQ ID NO 103
<211> LENGTH: 2966
<212> TYPE: DNA
<213> ORGANISM: Babesia microti

<400> SEQUENCE: 103
ctcgtgccga atgtcattta tgatctaata atattgtatt atctctaata ttatggtata 60
atagatactg tgaaaataaa ttcaactgga gataaggaaa ccatttgtat agatatttta 120
tacaaattat tatgaaataa tctaaataaa tgacaaaaaa tcgattatac aaatcacatt 180
aatgacaaac aaacttgtat acatatattg attaacatta caaaactaaa ttataatatt 240
tagattgata attgttataa tacttaacaa tattctactt tttaatataa ttttttattc 300
aataatatac tctttcatat tttgtactat tttatataat catatatatt atataattat 360
atatatttga taattgaata tatcaataat gatgatatac atgaatatgc atatataccc 420
catataatgt tattatattt agtgcttaca ttattaatta taaatatatt taaataatta 480
aataataatg aaaattaaca tagacaatat aatattaatc aatttgataa tattattgaa 540
tcgtaatgta gtatattgtg tggataaaaa tgatgtttca ttatggaaat caaaacctat 600
aacaactgtc agtaccacta atgatactat tacaaataaa tacactagta ctgtaattaa 660
tgccaatttt gctagctacc gtgaatttga ggatagggaa cctttaacaa taggatttga 720
atacatgatc gataaatcac aacaagataa attatcacat ccaaataaaa ttgataaaat 780
caaaatttct gattatataa ttgaatttga tgacaatgct aaattaccaa ctggtagtgt 840
taatgatata tccatcatta cttgcaagca taataatcca gtattaatta gattctcatg 900
tttaatagaa ggatctatct gctattattt ctacttattg aataatgata caaataaatg 960

-continued

```
gaataatcac aaattaaaat atgataaaac atacaatgaa catactgaca ataatggtat   1020
taattattat aaaatcgatt atagtgaatc tacagaacct actaccgaat ctactacctg   1080
tttttgtttt cgcaaaaaaa atcataaatc tgagcgtaaa gaattagaaa attataaata   1140
tgagggtaca gaattagcaa gaatacattg taataaaggg aaatgtgtaa aattgggtga   1200
cattaagata aaggataaga atttggaaat ttatgtgaaa cagttaatgt ctgtaaatac   1260
tccagtaaat tttgacaacc ctacatcgat taatctacca ctgtcagtac taccaatgat   1320
actattacaa ataaatacac tggactataa ttaatgccaa tattgttgag tactgtgatt   1380
gaggatgacc ttacaatagg ttagatcctt agataaatca caacaaaata aattatcaca   1440
tccaaataaa attgataaaa tcaaawttty tgattatata attgaatttg cacgagatgt   1500
taaattaaca acaattggta ctgtcaatat tatatatatc tatacttgca agcataataa   1560
tccagtatta gttgaattta tagtttctat agaagratct tactacaatt acttctactc   1620
aatgaataat gatacaaata aatggaataa tcataaaata aaatatgata caagatttaa   1680
tgaacatact gacatgaatg gtattaatta ttatgaatat gtacttggta aatgcagttc   1740
ttatacttgt aaaaatgaat atgagcataa agaattagca agaatacatt gtaatgaaga   1800
aaaatgtgta aatgtaaagg tagataacat tgggaataaa aatttggaaa tttatctaaa   1860
ataatttaac gaagtgtaat atgtaaaata gtttaatgaa gtataatatt atttaaaata   1920
attcaaaatt tcagaaatta atataattaa ttattataaa tacaaaataa ttaattacaa   1980
aataacgtat tattagccat ttcagattgt aaatacatat ttttacatat atttttatta   2040
aaactttcaa attaatgttt tcatttttat aagcattatt ataattatat actataatta   2100
tcagtcatca aataatatcc aaagttatcc tctacattat atcaatcata cagtatacaa   2160
ttatataaaa tattaacaac atataacaac caacattaat atatacataa tatctttatt   2220
aatcaatatt taatcaatac aataattaat agttaactaa ctatacacat agtgtatact   2280
aaattattat aaattatatg ttataattac aaaaacgtca tttacttatt ttatttcagt   2340
tatgtttcat agtctaattt agatttggtg aaacgcatct ggctgatgtg ctggtgagca   2400
agcagttcca cgaagcaaac aatatgactg atgcgctggc ggcgctttct gcggcggttg   2460
ccgcacagct gccttgccgt gacgcgctga tgcaggagta cgacgacaag tggcatcaga   2520
acggtctggt gatggataaa tggtttatcc tgcaagccac cagcccggcg gcgaatgtgc   2580
tggagacggt gcgcggcctg ttgcagcatc gctcatttac catgagcaac ccgaaccgta   2640
ttcgttcgtt gattggcgcg tttgcgggca gcaatccggc agcgttccat gccgaagatg   2700
gcagcggtta cctgttcctg gtggaaatgc ttaccgacct caacagccgt aacccgcagg   2760
tggcttcacg tctgattgaa ccgctgattc gcctgaaacg ttacgatgcc aaacgtcagg   2820
agaaaatgcg cgcggcgctg gaacagttga aagggctgga aaatctctct ggcgatctgt   2880
acgagaagat aactaaagca ctggcttgat aaataaccga atggcggcaa tagcgccgcc   2940
attcggggaa tttaccccctg ttttct                                         2966
```

<210> SEQ ID NO 104
<211> LENGTH: 1137
<212> TYPE: DNA
<213> ORGANISM: Babesia microti

<400> SEQUENCE: 104

```
gttttttccc cctgaggttt tgattgttaa tttaatgtca aattaattgg attaagaaat     60
```

-continued

```
gccagcagag catggtggtg aacacctcta attcccaggc aggtgaatct ttgagttcaa     120

ggccaacctc atgtacaaac ctagttccca gtatasccat gmytaamcag ggaaaccgkg     180

tctkgggaaa aamcaaaawt aaamcagaag agaaaggggg aaatgcctgg ggattagtga     240

ggttaatgcc agtggtggta tttattacca gagacaataa gaccgtgaga gctctgggaa     300

ttttgtttgt ttgtttttttg cttttccaag acagggtttc ttggtagctt tggagcctgt     360

cctggaactc aggctataga tcaggctggc ctcgaactca cagacatcca cctgcctctg     420

cctcccaaat gctgggatta aaggtgtgtg ctaccaccac ccgggctaga aagaacttgt     480

tagttgggat gtaaattctg ggtcatccct caaaacaaat ttgctagatt gtaaaccaga     540

ttgctcatag taaacggttg aagtagaact cgaagtctta tcttgaatcc taacaacaat     600

caaaggatat ttagtggtgt atgaaacggt cctagtgata acatccatgg actgtggaat     660

taattgattg ccaaatatta cacaaccaat tgaaaaccct gtagctgggg taactttggt     720

aaagattcca tcagtagaaa aaaccgtaac tagaagaaag accctctgga acttgatcaa     780

caaatcctat ttcgtttatg ttaagattca caatatttgt gacagcaaca tcttgtgtgg     840

tctccagaga cggagaaatt gttgatgtgg cagctgttgt tgatgtggta gctgttgttg     900

atgtggcagt tgttgttgat gtggcagttg ttgttgatgt ggtagctgtt gttgatgtag     960

cagatgttgt tgatgtagca gatgttgttg atgtagcagc tgttgttgat gtagcagctg    1020

ttgttgattg agcggcggtt gctgctgaag taggtattga atttgctata ctcacacttg    1080

tggcatcggt acctgcgcct cctctagtgt ttgttgccaa agtcagagtg agcctgt       1137
```

<210> SEQ ID NO 105
<211> LENGTH: 1010
<212> TYPE: DNA
<213> ORGANISM: Babesia microti

<400> SEQUENCE: 105

```
taggaatatg gatttgagct ttgcctatgg tatcatccca taggcatgag tcagggtcaa      60

aatcgccaga atattccagg caggttttag taaccctatc catcaatggc gtgttagggg     120

aaaccgaagg tatattattt gagttttcat ccttagatat acagttttct aaggcataag     180

gggttttccc gccagtgctt gtagtattgg ttattgacag tagtttttta gttccacttt     240

cattagtgat agctgcggag gcttttgcga tagagctggc tagtatagat gaagattttg     300

agtctttgtt tagggggaag tgaatggtgc aattgaagaa tttaataaaa ctattgacgt     360

catgaataac accattgggg accttggtat tgttattgac agcggtatta tttcaagcat     420

aaaatcatat atttccacaa tcgccaagat ttctaaagca ataatccctg gacaaatggc     480

attagttttt actgcattaa tattaattct aaattaaatg aaattcagat gtatatatta     540

ttatatagta caaaatttac acatttatta tatacatgaa cgaacatctt gctcttaaat     600

aaagaaattg agatataaat ggaaataaat taaaagtaac atgagaaaga tgaatataat     660

attaaaatat taaatttaac tgaaataaaa tgaaataaaa gaatgtattt tataataatt     720

tataataaat tagtatacaa tgattctaca ttataacaag cgagaataaa taattattga     780

ttagtcataa tattatgtat atgttaaggt ttattgttat gtgttgctaa tatgttatat     840

aattgtatac catagtgatt gatataatgt agaggataac tttggatatt atttgatgac     900

tgataattat agtatataat tataataatg kttataaaaa tgacattaat ttgaaagttt     960

aaattaaaat atatgtaaaa atatgtattt aaatctgaaa tggctaataa              1010
```

-continued

<210> SEQ ID NO 106
<211> LENGTH: 1162
<212> TYPE: DNA
<213> ORGANISM: Babesia microti

<400> SEQUENCE: 106

```
atgtgaatgc attgatcaag gagttgaacg ctcatattaa acagagagca acatctacaa     60

caacaattat tattgaaact aatgctaaag atgtggatga gttagtgaaa aaatttgcaa    120

caattgcatc ttttgatgat aagttcaaga acgtattctt tgataattct gttattgatg    180

aaattgtcaa aacgttggaa aagatgaagg ttgagtcaga tactgtatta cctagttgca    240

atggaatcca gaccactgaa aactctagta ctgacccata tacagtatta tcaaaactta    300

taaagaaaat taacgactcc ataatcagac ctatgacttc tcggctgatc aacaaatcct    360

ttccggagtt gtgcaagttg tttataaaaa tgcccgatgt cgactccaca aatttatggc    420

tttggatgtg gacataagcc amcactcttg taamcagrag agtcagatat tctgatggca    480

gatttaccat tgtaagcact gggtccaatt ttagatacac attggcmcca actgccgctt    540

ggtcatgatt tgtctctctt ctcccaattg ccaatctcaa tgattacggc acatcgcctc    600

aggagcaggc acttacatct tgcgtcagtc atggtaacga attcagcata gtaagcactg    660

caggcaagac aacttacact acacaatcta agttgttgtc acttttcaag ttatctgcgg    720

agacgttaag ggattttaat gaagctagat ttgcacttgg taacatgact gatagtgcta    780

ataaatctaa agctttggag gtctacaaat cgacactaac ttactatgaa atcaatatca    840

gtcgaattgg aaaagatttt tggcatatta aaatcaactc cgaatattac ttttgaatca    900

gttgtttcta aatacaaatt gactggtgtt aatacagttg atactgccaa tgctgatgtg    960

atcaacgaga caatgtttga cgatttgtcc aaggcaattt cctcatacct atactccctc   1020

atatctataa tttttccgga ggatattaaa ggtcaaggta caagtgaagg tcaacaaaca   1080

agtggaggtc aggatacaaa tgagacaatt ttctcatacc tatactccct catatctata   1140

atttttccgg aggatattaa ag                                             1162
```

<210> SEQ ID NO 107
<211> LENGTH: 984
<212> TYPE: DNA
<213> ORGANISM: Babesia microti

<400> SEQUENCE: 107

```
tgggtgagct agctgttgtc cagccttggt gtgattggac agtgtagagc tcatctgaag     60

tcttggcttg atagtgaggc tggaccatct cagctagcag ctttgaagct gttctggatg    120

cagaattttg agggaactgc aacagaggct ttctgagagg ctggatcaat tgggctactc    180

atctgtattg gtttctggtc cttttttttct gaaagcacaa acttttaaag gtaccatatg    240

tatctgcatt agcacaatgg aatgtgcagt gtgcacaggt caactaaagg ttttttcttc    300

tgtgtatgag caggtaaaag gcacctgtca actttataag tccaaacctt cgaaaatgat    360

ggcactatga catcaaaatt ttattccagg gagtccctag acccaacaac ctacatcgga    420

catgcaccta cagacatatt tacgtcgcca tggatcacga cccacatgca taacaagcgt    480

cttgttgact ttgaagttcc atttgaagca atttttgatg ataaactcat aagttattat    540

accggtacgg atgtcaacgg caagaataag gttcctgcag agcttaccaa ggcaatatgc    600

ggcaaagaag acgtgtgtga gcttaacatt accggtttat tgttgaaaga tattagtgct    660

aagaaattgg aggagtgtag gaagaagaat gcatctagtg gtactccatc tggtggtaca    720
```

-continued ccttctaatg ttccagagga gtgtgtgatt aaaagcaact tacagacggt tatgaagaag 780
gatgttacta caactttgaa atcggatgat gtcagcaatt acagtgttgt atccattcac 840
ttttacattg ataacgtgtt cagacataat actgcttttg gcagaattaa gattggcaac 900
cttgatctac cagcattttc cattgggttt atccactcga tcttcgtcga gagggttctc 960
atgggtgaca agagccttgc cagt 984

<210> SEQ ID NO 108
<211> LENGTH: 537
<212> TYPE: DNA
<213> ORGANISM: Babesia microti

<400> SEQUENCE: 108
ttatggaggg ctatttagat ctcgatttga attccaagat tggtaacttt atttcagcca 60
tcgaactcac taacctgacc aacacggtaa aatcagcgag cgtccaccct ccccaactaa 120
aagtgttggc tctgaagttt ggcaacaaga tcgttgatgt cgaggagaca ggcaggacat 180
ttgttacatt tgatgagaag ttgaattcaa tagaaataat taccttcgaa aatgatggca 240
ctatgacatc aaaattttat tccagggagt ccctagactc aacaacctac attggacatg 300
cctctacgta cacacttccc gaagtgctta ccaggtcatt atgtggtaaa gaggacttat 360
gtacgcttga cattacggat ctattgttga aagagattag tgctaagaaa ttggaggagt 420
gtaggaagaa gaatgcatct agtggtactc catctggtgg tacaccttct aatgttccag 480
aggagtgtgt aattagaacc aacttacaga tggttatgaa gaagaatgct cgtgccg 537

<210> SEQ ID NO 109
<211> LENGTH: 2559
<212> TYPE: DNA
<213> ORGANISM: Babesia microti
<220> FEATURE:
<221> NAME/KEY: misc_feature
<222> LOCATION: (1)...(2559)
<223> OTHER INFORMATION: n=A,T,C or G

<400> SEQUENCE: 109
ttcagaaatt aatataatta attattataa atacaaaata attaattaca aaataacgta 60
ttattagcca tttcagattt aaatacatat ttttacatat attttaattt aaactttcaa 120
attaatgtca tttttataaa cattattata attatatact ataattatca gtcatcaaat 180
aatatccaaa gttatcctct acattatatc aatcactatg gtatacaatt atataacata 240
ttagcaacac ataacaatca accttaacat atacataata ttatgactaa tcaataatta 300
tttattctcg cttgttataa tgtagaatca ttgtatacta atttattata aattattaca 360
aaatacactc ttttatttca ttttatttca gttaaattta atattttaat attatattca 420
tctttctcat gttactttaa tttatttcca tttatatctc aatttcttta tttaagagca 480
agatgttcgt tcatgtatat aataaatgtg naaattttgn actatataat aatatataca 540
tctgaatttc atttaattta gaattaatat taatgcagta aaaactagtg ccatttgtcc 600
agggattatt gaattagaaa tcttggcgat tgtggaaata tatgatttta tgcttgaaat 660
aataccgctg tcaataacaa taccaaggtc cccaatggtg ttattcatga cgtcaatagt 720
tttattaaat tcttcaattg caccattcac ttcatttaaa atgtcattaa aattagtgcc 780
aaaattctga ttattttcta atatcttgga tatcaaaaca ttagcttcta attcgtgctt 840
ttcaaatgct ttcttgatat cattaaattc gcttttattt gatataattg gtatgtgcat 900
attgtatatc tcagttaaat atcccataat tggtttaata ttatcattca gcaggtttct 960

-continued

```
aagtagttca gctttctttt tcttaatttc atactcaaaa ttttcagcat tttcaccttc   1020
aattgtacca agagccttat agtatatttc atcaacaatt gacttaatat cggtagagat   1080
agtggatata tcattaagca gtttaattat ttcattttta accgtactat tatttaaatc   1140
aatgtttgaa aaaatggcgt taaattccac aattttactt ttgagctcaa tttctttctt   1200
ttcaaggtaa tttttatgac caccattctt ctcatctgct tctagtatat caatactatt   1260
tttgcaggta tgaatcatag tgtccgtgat ctgttcagaa aattttgcat acattttttt   1320
agcctcgtta aaagcgatca taagatcgtt taatgctcgt ccaaaatcac ttgaatattg   1380
attaacatca ccatttcctg caaagacatt tccacttgtt aaaaagaatg taataaaatg   1440
aattagtatt ggtctaactg acttcatcct tatccacaat tgttattgat taatatatat   1500
gtttattata gttataataa cgttgtaata atgaaatact tgaattaatc ttcagataat   1560
aaatataagt tcaagttata aattgataga cgttatattc ttgttgatta ttatgtaata   1620
acatagttaa tttattatat ggggtcaaat aattttgtct ttatttgcct gcatacgtga   1680
tgtttatggt ttatcgctta attttattgt atattgtata aaaattgctc tataataata   1740
ataatataac agtaagattt gataatgata aatattgtat gataacataa ataatactaa   1800
ttatttctac aaatatatga ctatatcaca taaataaata ctatagtata gacatatttt   1860
atataacata gatatattag tatattttat attattactt tatcgttgta taatatacta   1920
gtcatttgac tttactttta ttatggcata tcatttgtgt ttatccttat tcctaataca   1980
atgttaatat aaacgtatct ccagtttata atgattgcaa gtatagatgc ttattaatat   2040
aaaagtatca ttggatatat ttgtaatatt gttaccaata tcacttttaa ctgacaatgg   2100
tatgattccc ttaataatcc attgtttcat cacacaatat agatccatat gttaaataac   2160
aatttgatta ttataaattt agatataaat aactttattt ttataataat taattatatt   2220
aatttcttaa atttcgaatt attttaaata atattatact tcattaaatt attttacata   2280
aatttccaaa ttcttatcct taatactata cacttttact catttttgct cactacattt   2340
ttgtttacca tattctgtat tataaggggg aaaggcacca tcacaaaagg tttcataata   2400
ttcaatacga ttatcgtcaa cttgatgact aatactggta cattctaatt tttcattttt   2460
ccattcatta ttatccttca atttgtagaa ataatagcgg gttgattttc ctatagtagc   2520
agaaaattgt attaatattg gttttttatg agaatcact                          2559
```

<210> SEQ ID NO 110
<211> LENGTH: 3141
<212> TYPE: DNA
<213> ORGANISM: Babesia microti
<220> FEATURE:
<221> NAME/KEY: misc_feature
<222> LOCATION: (1)...(3141)
<223> OTHER INFORMATION: n=A,T,C or G

<400> SEQUENCE: 110

```
acatgttgac ttttggaaat atacgttttc ataatataaa tctcccacca ttttcattgg     60
gcataattca ctcgattacg gtagaaaagg cgattaactc tgaagatttt gacggaatac    120
aaacactttt acaagtgtct atcattgcta gttacggtcc atctggcgat tacagtagtt    180
ttgtgttcac tccagttgta acagcagaca ccaacgtttt ttacaaatta gagacggatt    240
tcaaacttga tgttgatgtt attactaaga catcactaga attgcccaca agtgttcctg    300
gctttcacta caccgaaact atttaccaag gcacagaatt gtcaaaattt agcaagcctc    360
```

-continued

```
agtgcaaact taacgatcct cctattacaa caggatcggg gttgcaaata atacatgatg     420
gtttgaataa ttcgacaatt ataaccaaca aagaagttaa tgtggatgga acagatttag     480
tttttttga attgctccct ccatcggatg gcattcccac cttgcgatca aaattatttc     540
ccgtcctgaa atcaattcca atgatatcta ccggggttaa tgaattactg ttggaagtac     600
tcgagaaccc ctctttccct agtgcaatta gcaattacac cggactgaca ggccgactta     660
acaaattact tacagtttta gacggtattg ttgatagcgc cattagtgtc aagactacag     720
aaactgtccc tgacgacgca gaaacttcta tttcttcatt gaaatcattg ataaaggcaa     780
tacgagataa tattactacc actcgaaacg aagttaccaa agatgatgtt tatgcattga     840
agaaggccct cacttgtcta acgacacacc taatatatca ttcaagagta gatggtatat     900
cattcgacat gctgggaaca caaaaaaata aatctagccc actaggcaag atcggaacgt     960
ctatggacga tattatagcc atgttttcga atcccaatat gtatcttgtg aaggtggcgt    1020
acttgcaagc cattgaacac atttttctca tatcaaccaa atacaatgat atatttgatt    1080
acaccattga ttttagtaag cgtgaagcta ctgattctgg atcatttacc gatatattgc    1140
tcggaaacaa ggtgaaggaa tctttgtcat ttattgaggg tttgatttct gacataaaat    1200
ctcactcatt gaaagctggg gttacaggag gtatatcaag ttcatcatta tttgatgaaa    1260
tcttcgacga gttaaatttg gatcaagcaa caattagaac ccttgttgca ccattagaag    1320
aaattaaaaa tgagcttaag actatttcct ctcagaaaat agccgatgcc acagtaaccc    1380
cttctacccc caataccaat gtgaacatca aaacaattat cagcaagatt aagaaaattt    1440
tgatgataag tgagactatt tcatccacag ctcttgcacg tttatctgca gtattaagca    1500
ttcttggtag ggggacttcc acaaatgtca ttccggaacg tctaactagt atcgttgttg    1560
atttgaaatc ggcaactgtt ccacaggaag tggcgcttaa gaatggagtt tacaagttga    1620
aggaccaatt taagctaacg cacaagatga tacctgtttt tggcagcgtg caactgcaga    1680
ttccagagaa atcaacagtc gtgcagataa gtgtagtaga gcatgaaaat gataccaaaa    1740
tggcaatcat caccccttgat gatcattcga aattgacttt ggaaagggtg attctttcag    1800
aaacccctac tgttgttggt ttaacccaca ccacacaaga tccactggat gtattgctat    1860
caatatttgt caagatggat aatacaacgg atgatggggt tatggagggc tatttagatc    1920
tcgatttgaa ttccaagatt ggtactttta tttcggccat cgaactcatt gacttgacca    1980
cccggtaaat tcagcgagcg tccaccntcc ccaactaaaa gtgttggctc tgaagtttgg    2040
caccaagatc gttgatgtcg aggagacagg caggacattt gttacatttg atgagaagtt    2100
gaattcaata gaaataatta ccttcgaaaa tgatggcact tatgacatca aaattttatt    2160
ccagggagtc cctagaccca acaacctaca tcggacatgc acctacagac atatttacgt    2220
cgccatggat cacgacccac atgcataaca agcgtcttgt tgactttgaa gttccatttg    2280
aagcaatttt tgatgataaa ctcataagtt attataccgg tacggatgtc aacggcaaga    2340
ataaggttcc tgcagagctt accaaggcaa tatgcggcaa agaagacgtg tgtgagctta    2400
acattaccgg tttattgttg aaagatatta gtgctaagaa attggaggag tgtaggaaga    2460
agaatgcatc tagtggtact ccatctggtg gtacaccttc taatgttcca gaggagtgtg    2520
tgattaaaag caacttacag acggttatga agaaggatgt tactacaact ttgaaatcgg    2580
atgatgtcag caattacagt gttgtatcca ttcactttta cattgataac gtgttcagac    2640
ataatactgc ttttggcaga attaagattg gcaaccttga tctaccagca ttttccattg    2700
ggtttatcca ctcgatcttc gtcgagaggg ttctcatggg tgacaagagc cttgccagtg    2760
```

-continued

```
ttggcattat aactaactac ggtccaagtg gagactatga gttgttgaga tacatgcaag   2820

ttgaggaagg gaagaattat ttcaaactcg tacaggggcc agaaataaca gctgattata   2880

ttggatctgg gttgactaaa cacaagaggc tgaccatgaa tggcgcctcc accggttcaa   2940

ttggatttga aaccaactac aaggaatcga tactcttcaa tgagtttatg cgtccaacca   3000

acaagatagt caccctcttc tatacggata gtgaaactgt caatcttatc aagctgcact   3060

cattggagaa tgtaaagcat ggtgttactt attcaattta cggtgccttc ccaattgaag   3120

aatcatctcc tgaaagttca t                                             3141
```